United States Patent
Stanley et al.

(10) Patent No.: US 12,005,265 B2
(45) Date of Patent: *Jun. 11, 2024

(54) COMPOSITIONS AND METHODS TO MODULATE CELL ACTIVITY

(71) Applicants: THE ROCKEFELLER UNIVERSITY, New York, NY (US); RENSSELAER POLYTECHNIC INSTITUTE, Troy, NY (US)

(72) Inventors: Sarah Stanley, Berkeley, CA (US); Jeffrey Friedman, New York, NY (US); Jonathan S. Dordick, Schenectady, NY (US); Jeremy Sauer, Princeton, NJ (US)

(73) Assignees: THE ROCKEFELLER UNIVERSITY, New York, NY (US); RENSSELAER POLYTECHNIC INSTITUTE, Troy, NY (US)

( * ) Notice: Subject to any disclaimer, the term of this patent is extended or adjusted under 35 U.S.C. 154(b) by 679 days.

This patent is subject to a terminal disclaimer.

(21) Appl. No.: 16/986,482

(22) Filed: Aug. 6, 2020

(65) Prior Publication Data

US 2021/0052909 A1    Feb. 25, 2021

Related U.S. Application Data

(63) Continuation of application No. 15/464,748, filed on Mar. 21, 2017, now Pat. No. 10,765,878, which is a continuation of application No. PCT/US2015/051457, filed on Sep. 22, 2015.

(60) Provisional application No. 62/053,602, filed on Sep. 22, 2014.

(51) Int. Cl.
| | | |
|---|---|---|
| *A61N 2/00* | (2006.01) | |
| *A61K 48/00* | (2006.01) | |
| *A61N 2/06* | (2006.01) | |
| *C07K 14/705* | (2006.01) | |
| *C12N 15/62* | (2006.01) | |
| *C12N 15/86* | (2006.01) | |
| *A61K 9/51* | (2006.01) | |
| *A61K 47/69* | (2017.01) | |
| *A61P 3/08* | (2006.01) | |

(52) U.S. Cl.
CPC .............. *A61N 2/002* (2013.01); *A61K 48/00* (2013.01); *A61K 48/005* (2013.01); *A61K 48/0075* (2013.01); *A61N 2/00* (2013.01); *A61N 2/004* (2013.01); *A61N 2/06* (2013.01); *C12N 15/62* (2013.01); *C12N 15/86* (2013.01); *A61K 9/51* (2013.01); *A61K 47/6929* (2017.08); *A61P 3/08* (2018.01); *C07K 14/705* (2013.01); *C07K 2319/00* (2013.01); *C12N 2710/10343* (2013.01); *G01N 2800/042* (2013.01)

(58) Field of Classification Search
CPC .......... A61N 2/002; A61N 2/00; A61N 2/004; A61N 2/06; A61K 48/00; A61K 48/005; A61K 48/0075; C12N 15/62; C12N 15/86
USPC ................. 600/9; 435/320.1, 325, 368, 400; 424/93.21

See application file for complete search history.

(56) References Cited

U.S. PATENT DOCUMENTS

| | | | |
|---|---|---|---|
| 8,435,762 B2 | 5/2013 | Sternson et al. | |
| 8,957,036 B2 | 2/2015 | Goss et al. | |
| 9,399,063 B2 * | 7/2016 | Friedman | C07K 16/18 |
| 10,765,878 B2 * | 9/2020 | Stanley | C12N 15/86 |
| 2004/0023203 A1 | 2/2004 | Miesenbock et al. | |
| 2011/0034753 A1 | 2/2011 | Dobson et al. | |
| 2017/0226179 A1 | 8/2017 | Liu et al. | |

FOREIGN PATENT DOCUMENTS

| | | | |
|---|---|---|---|
| CN | 103228793 A | 7/2013 | |
| CN | 103249878 A | 8/2013 | |
| WO | 2013029025 A1 | 2/2013 | |
| WO | WO 2013/029025 | * | 2/2013 |

OTHER PUBLICATIONS

"Administer" entry in Medical Dictionary of the Free Dictionary, https://medical-dictionary.thefreedictionary.com/administer (2022).*
Piacentini et al. (2008) J. Cell Physiol., vol. 215, 129-139.*
Stanley et al., (2012) Science, vol. 336, 604-608.*
Pingbo et al. (2011) "A surprising stretch: Mechanosensitive gating of CFTR chloride channel in simple epithelial cells". Mechanobiology Institute, Singapore, seminar notice/abstract (Sep. 8, 2011) [http://mbi.nus.edu.sg/seminartext/a-surprising-stretch-mechanosensitive-gating-of-cftr-chloride-channel-in-simp.*
Hughes et al. (2008) J. R. Soc. Interface, vol. 5, 855-863.*
Caterina, et al., "The capsaicin receptor: a heat-activated ion channel in the pain pathway", Nature, vol. 389, Oct. 23, 1997, 816-824.
Cheng, et al., "Suppression of Neuronal Hyperexcitability and Associated Delayed Neuronal Death by Adenoviral Expression of GABAc Receptors", The Journal of Neuroscience, vol. 21(10), May 15, 2001, 3419-3428.

(Continued)

Primary Examiner — Anne Marie S Wehbe
(74) Attorney, Agent, or Firm — Edgar W. Harlan; Carolyn S. Elmore; Elmore Patent Law Group, P.C.

(57) ABSTRACT

The present invention provides methods and compositions for the remote control of cell function based on the use of a magnetic field to excite paramagnetic nanoparticles targeted to specific cell types. The cell type of interest expresses an ion channel wherein excitation of the paramagnetic nanoparticles results in a physical change that is transduced into a cellular response. Such cellular responses may include, for example, increases in gene expression resulting in production of one or more physiologically active proteins. The expression of such proteins can be used to treat a variety of different inherited or acquired diseases or disorders in a subject.

5 Claims, 47 Drawing Sheets

Specification includes a Sequence Listing.

(56) References Cited

OTHER PUBLICATIONS

Cooper, "Host Cell-Specific Folding and Assembly of the Neuronal Nicotinic Acetylcholine Receptor .alpha.7 Subunit", J. Neurochem., 68(5), 1997, 2140-2151.

Ehrengruber, et al., "Activation of heteromeric G protein-gated inward rectifier K+ channels overexpressed by adenovirus gene transfer inhibits the excitability of hippocampal neurons", Proc. Natl. Acad. Sci. USA, vol. 94, Jun. 1997, 7070-7075.

Huang, et al., "Remote control of ion channels and neurons through magnetic-field heating of nanoparticles", Nature Nanotechnology, 5(8), 2010, 602-606.

Hughes, Steven et al., "Selective activation of mechanosensitive ion channels using magnetic particles", Journal of the Royal Society Interface, vol. 5, (2008), 2008, 855-863.

Johns, et al., "Inducible Genetic Suppression of Neuronal Excitability", The Journal of Neuroscience, vol. 19, Issue 5, Mar. 1, 1999, 1691-1697.

Khakh, et al., "Activation-dependent changes in receptor distribution and dendritic morphology in hippocampal neurons expressing P2X2—green fluorescent protein receptors", Proc. Natl. Acad. Sci. USA, vol. 98, Apr. 24. 2001, 5288-5293.

Kuhn, F. J. et al., "The Transmembrane Segment S6 Determines Cation versus . . . ", Journal of Biological Chemistry, vol. 282, No. 38, Sep. 21, 2007, 27598-27609.

Kupper, et al., "Recombinant Kv1.3 potassium channels stabilize tonic firing of cultured rat hippocampal nuerons, Pflugers Archiv.", Eur. J. Physiol., vol. 443, Feb. 2002, 541-547.

Lerchner, et al., "Reversible Silencing of Neuronal Excitability in Behaving Mice by a Genetically Targeted, Ivermectin-Gated Cl-Channel", Neuron, vol. 54, Issue 1, Apr. 5, 2007., 35-49.

McKemy, et al., "Identification of a cold receptor reveals a general role for TRP channels in thermosensation", Nature, vol. 416, Mar. 7, 2002, 52-58.

Nadeau, et al., "ROMK1 (Kir1.1) Causes Apoptosis and Chronic Silencing of Hippocampal Neurons", J. Neurophysiol., vol. 84(2), Aug. 2000, 1062-1075.

Nitabach, et al., "Electrical Silencing of *Drosophila* Pacemaker Neurons Stops the Free-Running Circadian Clock", Cell, vol. 109, Issue 4, May 17, 2002, 485-495.

Okada, et al., "Functional Correlation of GABA(a) Receptor alpha Subunits Expression with the Properties of IPSCs in the Developing Thalamus", J. Neurosci., vol. 20(6), Mar. 15, 2000, 2202-2208.

Piacentini, R. et al., "Extremly Low-Frequency Electronmagnetic Fileds Promote in viro Neurogenesis Via Upregulation of Cav1-Channel Activity", J Cell Physiol., 215, 2008, 129-39.

Pingbo, et al., "A surprising stretch: Mechanosensitive gating of CFTR chloride channel in simple epithelial cells", Mechanobiology Inst, Singapore, seminar notice/abstract (Sep. 8, 2011), URL: http://mbi.nus.edu.sg/seminartext/a-surprising-stretch-mechanosensitive-gating-of-cftr-chloride-channel-in-simple-epithelial-cells/], abst. [Retrieved from the internet on Feb. 1, 2016].

Slimko, et al., "Selective Electrical Silencing of Mammalian Neurons In Vitro by the Use of Invertebrate Ligand-Gated Chloride Channels", J. Neurosci., vol. 22(17), Sep. 1, 2002, 7373-7379.

Stanley, S. A. et al., "Radio-Wave Heating of Iron Oxide Nanoparticles Can Regulate Plasma Glucose in Mice", Science, American Association for the Advancement of Science, vol. 336, No. 6081, May 4, 2012, 604-608.

Stanley, S. A. et al., "Remote regulation of glucose homeostasis in mice using genetically encoded nanoparticles", Nature Medicine, vol. 21, No. 1, Dec. 15, 2014, 92-98.

Susankova, et al., "Contribution of the Putative Inner-Pore Region to the Gating of the Transient Receptor Potential Vanilloid Subtype 1 Channel (TRPV1)", The Journal of Neuroscience, vol. 27, No. 28, 2008, 7578-7585.

Tobin, et al., "Combinatorial Expression of TRPV Channel Proteins Defines Their Sensory Functions and Subcellular Localization in C. elegans Neurons", Neuron, vol. 35, Jul. 18, 2002, 307-318.

White, et al., "Molecular genetic approaches to the targeted suppression of neuronal activity", Current Biology, vol. 11 (24), Dec. 11, 2001, R1041-R1053.

Winter, et al., "Functionally important amino acid residues in the transient receptor potential vanilloid 1 (TRPV1) ion channel ? an overview of the current mutational data", Mol. Pain., vol. 9, No. 30, 2013, 1-30.

Day, et al. "Nanoparticles for Thermal Cancer Therapy," Journal of Biomechanical Engineering, vol. 131, pp. 074001 1-5, Jul. 2009.

* cited by examiner

```
         10         20         30         40         50
MEQRASLDSE ESESPPQENS CLDPPDRDPN CKPPPVKPHI FTTRSRTRLF
         60         70         80         90        100
GKGDSEEASP LDCPYEEGGL ASCPIITVSS VLTIQRPGDG PASVRPSSQD
        110        120        130        140        150
SVSAGEKPPR LYDRRSIFDA VAQSNCQELE SLLPFLQRSK KRLTDSEFKD
        160        170        180        190        200
PETGKTCLLK AMLNLHNGQN DTIALLLDVA RKTDSLKQFV NASYTDSYYK
        210        220        230        240        250
GQTALHIAIE RRNMTLVTLL VENGADVQAA ANGDFFKKTK GRPGFYFGEL
        260        270        280        290        300
PLSLAACTNQ LAIVKFLLQN SWQPADISAR DSVGNTVLHA LVEVADNTVD
        310        320        330        340        350
NTKFVTSMYN EILILGAKLH PTLKLEEITN RKGLTPLALA ASSGKIGVLA
        360        370        380        390        400
YILQREIHEP ECRHLSRKFT EWAYGPVHSS LYDLSCIDTC EKNSVLEVIA
        410        420        430        440        450
YSSSETPNRH DMLLVEPLNR LLQDKWDRFV KRIFYFNFFV YCLYMIIFTA
        460        470        480        490        500
AAYYRPVEGL PPYKLKNTVG DYFRVTGEIL SVSGGVYFFF RGIQYFLQRR
        510        520        530        540        550
PSLKSLFVDS YSEILFFVQS LFMLVSVVLY FSQRKEYVAS MVFSLAMGWT
        560        570        580        590        600
NMLYYTRGFQ QMGIYAVMIE KMILRDLCRF MFVYLVFLFG FSTAVVTLIE
        610        620        630        640        650
DGKNNSLPME STPHKCRGSA CKPGNSYNSL YSTCLELFKF TIGMGDLEFT
        660        670        680        690        700
ENYDFKAVFI ILLLAYVILT YILLLNMLKA LMGETVNKIA QESKNIWKLQ
        710        720        730        740        750
RAITILDTEK SFLKCMRKAF RSGKLLQVGF TPDGKDDYRW CFRVDEVNWT
        760        770        780        790        800
TWNTNVGIIN EDPGNCEGVK RTLSFSLRSG RVSGRNWKNF ALVPLLRDAS
        810        820        830
TRDRHATQQE EVQLKHYTGS LKPEDAEVFK DSMVPGEK
```

Fig. 18 ial application of U.S. application Ser. No. 15/464,748, filed on Mar. 21, 2017 which is a continuation of International Application No. PCT/US2015/051457, which designated the United States and was filed on Sep. 22, 2015, published in English, which claims the benefit of U.S. Provisional Application No. 62/053,602, filed on Sep. 22, 2014. The entire teachings of the above applications are incorporated herein by reference.

COMPOSITIONS AND METHODS TO MODULATE CELL ACTIVITY

RELATED APPLICATIONS

This application is a continuation application of U.S. application Ser. No. 15/464,748, filed on Mar. 21, 2017 which is a continuation of International Application No. PCT/US2015/051457, which designated the United States and was filed on Sep. 22, 2015, published in English, which claims the benefit of U.S. Provisional Application No. 62/053,602, filed on Sep. 22, 2014. The entire teachings of the above applications are incorporated herein by reference.

GOVERNMENT SUPPORT

This invention was made with government support under NIH Grant No. R01 GM095654 awarded by the National Institutes of Health. The government has certain rights in the invention.

FIELD OF THE INVENTION

The present invention provides methods and compositions for the remote control of cell function based on the use of radiofrequency waves or a magnetic field to excite endogenous paramagnetic nanoparticles produced by specific cell types. The cells express a set of DNA constructs that direct the expression of a temperature sensitive and/or mechanosensitive channel wherein excitation of the paramagnetic metal nanoparticles results in a physical change that is transduced into a cellular response by induction of the influx of ions including cations such as $Ca^{2+}$ or $Na^+$ or anions such as Cl. Co-expression of the endogenous nanoparticles with other channels could also enable modulation of other signal transduction pathways. Such inducible cellular responses may include, for example, increases in gene expression resulting in production of one or more physiologically active proteins. The expression of such proteins can be used to treat a variety of different inherited or acquired diseases or disorders in a human or animal subject. The method can also be used to activate or inhibit endogenous cells whose activity can be modulated by the flux of ions. Thus, the system can also be used to modulate the activity of neurons, endocrine cells, secretory cells, contractile cells and any other cell type in which a change in ion flow changes cellular activity.

BACKGROUND OF THE INVENTION

The tools for dissecting the contribution of specific cells to physiological functions and particular behavior have evolved over recent years. Initial studies used electrical and chemical lesions to ablate both neurons and fibers in defined regions. Later investigations made use of direct stimulation through implanted electrodes; however, these studies were hampered by variable activation, the need for permanent implants, and tissue damage. As an alternative to these approaches, recent techniques make use of drug inducible systems to alter gene expression or ion channels to modulate cell activity (Lerchner et al., Neuron 2007, 54:35-49). By allowing the selective passage of cations or anions, families of ion channels regulate intracellular ion concentrations, which in turn modulate intracellular functions according to the cell type. The use of ion channels has many advantages; their structure and function are relatively well described, they have a rapid time course of activation, and a broad range of channels exist in mammalian and non-mammalian cells, which may be exploited in the search for the optimum means of modifying cellular activity. This approach was first validated by transgenic expression of a drug-gated channel to modify behavior; however, the time course of effects was relatively slow (hours to days). Recently, the non-mammalian channelrhodopsin (ChR2) gene, which encodes a light activated cation channel, has been employed to rapidly activate molecularly defined neurons when exposed to blue light (Boyden, E S et al. 2005 Nat Neurosci 8:1263-1268). This system gives anatomical specificity and temporal control but also has limitations. For example, activation in vivo requires fiber optic light delivery via implanted devices that are invasive and can interfere with behavior. The requirement for an implanted device also limits the number of anatomic sites than can be simultaneously regulated.

The present invention provides methods and compositions for the remote control of cell function based on the use of radiofrequency waves or a magnetic field to excite or inhibit cells expressing endogenous nanoparticles. The invention uses Nanoparticle Induced Cellular Regulation (NICR) to, for example, regulate ion channels as a means for stimulating or inhibiting the activity of specific cells remotely and non-invasively and at one or at multiple sites.

SUMMARY OF THE INVENTION

The invention described herein utilizes Nanoparticle Induced Cellular Regulation (NICR), which encompasses compositions and methods that have been developed for modulating cell activity, such as either increasing or decreasing the activity of specific cells remotely and non-invasively. The present invention provides methods and compositions based on the use of radiofrequency waves or a magnetic field to exert a mechanical force on endogenous paramagnetic nanoparticles produced within specific cell types. The cell type of interest expresses an ion channel tethered to a metal binding protein associated with paramagnetic nanoparticles, wherein exposure of the paramagnetic nanoparticles to an electromagnetic or magnetic field results in a physical change that is transduced into a cellular response via changes in ion flow across a cell membrane. The excitation of the paramagnetic nanoparticles results in a localized temperature increase and/or mechanical force using radio-waves or a mechanical force using a magnet that is transduced into a cellular response such as, for example, an increase in expression of one or more target genes or the regulation of neural activity. Such increases in gene expression can result in production of one or more physiologically active proteins. The expression of such proteins can be used to treat a variety of different inherited or acquired diseases or disorders in a subject. Methods of the invention can further be used to regulate neural activity and thereby treat a variety of neural diseases that result from dysfunction of specific neural circuits.

Other activities of the cell that may be stimulated include, for example, cellular responses such as cell proliferation and/or differentiation, apoptosis, activation of signal transduction pathways, neuronal activation or inhibition, or development of long term potentiation and/or regulation of gene expression.

In one embodiment, the invention provides a genetic construct comprising a nucleotide sequence, such as a DNA sequence, which encodes a metal binding protein, such as ferritin or a ferritin variant fused to a first polypeptide and a nucleotide sequence which encodes an ion channel fused to a second polypeptide. The first polypeptide is a binding partner of the second polypeptide. The genetic construct preferably further comprises one or more promoters operably linked to one or both encoding nucleotide sequences. Preferably the nucleotide sequences are DNA sequences; more preferably the sequences are double stranded DNA.

In another embodiment, the invention provides a vector which comprises a genetic construct of the invention.

In another embodiment, the invention provides a recombinant cell such as a stem cell or other cell type, or a population of recombinant cells, such as stem cells or other cell types, which comprise the genetic construct of the invention and express or can be induced to express the proteins encoded by the genetic construct. In one embodiment the recombinant cell further comprises a genetic construct comprising a nucleotide sequence which encodes a protein, peptide or nucleotide of interest operably linked to a promoter which is induced by activation of the ion channel, such as a promoter which is dependent on the ion gated by the channel. In one embodiment, the channel is a calcium channel and the recombinant gene for the protein of interest is operably linked to a $Ca^{2+}$ inducible promoter.

In another embodiment, the recombinant cells are produced by a method comprising the step of introducing a genetic construct of the invention into a population of cells. The genetic construct can be introduced directly, for example, via electroporation or LIPOFECTAMINE 2000™ mediated transfection. Preferably, the genetic construct is introduced by contacting the cells with a vector comprising a genetic construct of the invention. Optionally, the method can further include introducing into the cells a nucleotide sequence which encodes a protein, peptide or nucleotide and further includes a promoter operatively linked to the encoding sequence, where the promoter is induced by activation of the ion channel, such as a promoter which is dependent on the ion gated by the channel. This nucleic acid sequence can be introduced directly or by contacting the cells with a vector comprising the nucleotide sequence, which encodes a protein, peptide or nucleotide of interest operably linked to a promoter which is induced by activation of the ion channel, such as a promoter which is dependent on the ion gated by the channel. In one embodiment, the genetic construct and the nucleotide sequence which encodes the protein, peptide or nucleotide of interest are present in the same vector. In another embodiment, the genetic construct and the nucleotide sequence which encodes the protein, peptide or nucleotide of interest are provided in separate vectors.

In another embodiment, the invention provides pharmaceutical compositions comprising a vector of the invention, in combination with a pharmaceutically acceptable carrier.

In another embodiment, the invention provides pharmaceutical compositions comprising recombinant cells of the invention, in combination with a pharmaceutically acceptable carrier.

In one embodiment, the invention provides a method of modulating an activity of a cell or a population of cells, comprising the steps of (1) providing a recombinant cell or a population of recombinant cells which comprise the genetic construct of the invention and (2) exposing the cell or cells to radiofrequency radiation or to a magnetic field, thereby modulating the activity of the cell or cells. In certain embodiments, the method either increases or decreases the activity of the cells such as for normalizing the activity of neural circuits whose activity has been altered either by the loss of a key cell type such as in Parkinson's Disease or by abnormal activity of neural circuits such as in chronic pain, tremor, seizures and others.

In one embodiment, the invention provides a method of producing a protein, peptide or nucleotide comprising the steps of (1) providing a population of recombinant cells which comprise a genetic construct of the invention; (2) exposing the cells to radiofrequency radiation or to a magnetic field, thereby activating the ion channel encoded by the genetic construct and inducing the cells to produce the protein, peptide or nucleic acid; and (3) isolating the protein or peptide. The protein, peptide or nucleic acid can be encoded by an endogenous gene or by a recombinant gene. In one embodiment, the recombinant cells further comprise a recombinant gene encoding the protein, peptide or nucleic acid, operably linked to a regulatory nucleic acid sequence which is induced by activation of the ion channel encoded by the genetic construct.

In another embodiment, the invention provides a method of administering a protein, peptide or nucleic acid having therapeutic or prophylactic activity to a subject in need thereof. In one embodiment, the method comprises the steps of (1) administering to the subject an effective amount of a pharmaceutical composition of the invention; and (2) exposing the subject to radiofrequency radiation or a magnetic field, thereby inducing expression of the protein, peptide or nucleic acid.

In one embodiment, the pharmaceutical composition comprises recombinant cells. Preferably, the recombinant cells are autologous cells. In one embodiment, the recombinant autologous cells are produced by a method comprising the steps of (1) removing cells from the subject; (2) transfecting the cells with a genetic construct of the invention and, optionally, a nucleotide sequence which encodes the therapeutic protein, peptide or nucleic acid operably linked to a promoter which is induced by activation of the ion channel encoded by the genetic construct.

In another embodiment, the pharmaceutical composition comprises a vector of the invention in combination with a pharmaceutically acceptable carrier. Suitable vectors include, but are not limited to, viruses, such as Adeno Associated Virus, and other means for delivering the constructs as are known in the art. In certain embodiments, the pharmaceutical composition comprising a vector is administered by injection such as localized injection or transdermal delivery for example, for peripheral nerves, at or near the site of the target cells.

In the methods of the invention for producing a protein, peptide or nucleic acid, the protein, peptide or nucleic acid of interest is encoded by a gene which is activated upon activation of the channel. The gene encoding the protein or peptide of interest can be, for example, an endogenous gene which is dependent upon the ion gated by the ion channel or a recombinant gene operably linked to a regulatory sequence which is activated by the ion gated by the ion channel. For example, when the ion channel is a calcium channel, the protein or peptide of interest can be encoded by a $Ca^{2+}$-dependent endogenous gene or a recombinant gene which is operably linked to a $Ca^{2+}$ dependent promoter.

In another embodiment, the invention provides a method of modulating the activity of target cells in a subject. The method comprises the steps of (1) administering to the subject a pharmaceutical composition of the invention and (2) exposing the subject to radiofrequency radiation or a magnetic field, thereby modulating the activity of the target cells.

In certain embodiments, the subject suffers from a disorder for which modulation of the target cell activity provides a therapeutic or prophylactic effect.

In one embodiment, the pharmaceutical composition comprises recombinant cells of the invention, and these recombinant cells are the target cells.

In another embodiment the pharmaceutical composition comprises a vector of the invention and the target cells are endogenous cells.

In one embodiment, the subject suffers from a neurological disorder, the pharmaceutical composition comprises a vector of the invention and the target cells are endogenous neurons.

In the preceding embodiments, the ion channel encoded by the genetic construct is selected such that activation of the ion channel leads to desired modulation of the target. In one embodiment, the cells are neurons and the ion channel is a chloride channel. In another embodiment, the cells are neurons and the channel is a cation channel, such as a calcium channel.

The present invention can be used in a variety of different clinical settings. For example, the technology can be used to control the expression of physiologically active proteins for use in treatment of various inherited or acquired disorders or diseases. For example, in one embodiment, induced pluripotent stem cells (iPSC) or autologous mesenchymal stem cells engineered to express the genetic constructs of the invention serve as autografts enabling external control of cell function. NICR dependent calcium entry can then be used to regulate functions including hormone release, muscle contraction, or neural activity and others. Regulated hormone expression and release can facilitate the treatment of several endocrine conditions such as diabetes. Neuronal stimulation can be used therapeutically in debilitating conditions such as Parkinson's disease (subthalamic stimulation) and stroke (transcranial direct current stimulation), as well as for pain relief and gastroparesis (Benabid, A L et al., 2009 Lancet Neurol 8, 67-81; Schlaug G. et al. 2008 Arch Neurol 65:1571-1576; Nnoaham K E, Kumbang J, 2008 Cochrane Database Syst Rev CD 003222; Marank, J; Parkman H P, 2007 Curr Gastroenterol Rep 9:286-294). These applications and approaches can be applied in human and nonhuman subjects using the NICR techniques.

In one embodiment, the invention provides a mutant ion channel which results from mutation of one or more amino acid residues of a calcium channel. Preferably, the mutant channel is a chloride channel. Preferably the mutant channel results from a point mutation. In one embodiment, the mutant channel results from substitution of Ile679, Ile680, or a corresponding Ile residue, of calcium channel TRPV1 with Lys (hereinafter "TRPV1$^{Mutant}$"). This single amino acid substitution results in a mutant channel that gates chloride rather than calcium. Thus, the genetic construct of the invention can encode TRPV1$^{Mutant}$ in embodiments in which a chloride channel is desired to inhibit cellular activity in cells such as neurons. Further, the invention provides TRPV1$^{Mutant}$ proteins, nucleotide sequences, preferably DNA sequences, which encode the mutant proteins, vectors comprising these nucleotide sequences optionally operably linked to a promoter sequence, and recombinant cells comprising such nucleotide sequences. In preferred embodiments, TRPV1$^{Mutant}$ results from mutation of native TRPV1 from a human or a nonhuman animal, preferably mammalian TRPV1, and more preferably human TRPV1. In one embodiment, the mutant TRPV1 channel is a mutant rat TRPV1 channel comprising the amino acid sequence set forth in FIG. 18 (SEQ ID NO: 1), also referred to herein as rat I679K-TRPV1, or an isoform thereof. It is to be understood that in certain mammalian TRPV1 channels, the native Ile residue substituted with Lys corresponds to that of Ile679 in the rat sequence, although it may not be at position 679 in the mammalian sequence. For example, the corresponding mutant human TRPV1 is human I680K-TRPV1, for example, based on wildtype sequence UniProt accession number Q8NER1 or an isoform thereof, and the corresponding mutant mouse TRPV1 is mouse I680K-TRPV1, for example, based on wildtype sequence UniProt accession number Q704Y3 or an isoform thereof. The TRPV1$^{Mutant}$ channel described in the working examples and figures herein is rat 679K-TRPV1.

Further, the methods and compositions of the invention provide a means for dissecting the contributions of defined cell populations to physiology. The present invention makes it possible to express ferritin cores in different cell types. The invention provides for selective modification of cellular function non-invasively both in vitro and in vivo. Such a technique allows one to study the roles of cell populations in physiological processes, in particular those functions that are, or would be, perturbed by invasive methods.

Further, the invention provides non-human transgenic animals containing different cell types that can be activated remotely via radiofrequency radiation or a magnetic field through the targeting of endogenous paramagnetic nanoparticles in said cells. The transgenic animals provide an in vivo means for studying the contributions of defined populations of cells or defined populations of peptides to physiology. Further, the transgenic animals of the invention may be used as animal model systems for the screening, identification and testing of useful therapeutic compounds.

In certain embodiments, the invention described herein provides, for example, methods to remotely modulate cell function in vertebrates and apply NICR to (i) modify glucose metabolism (ii) activate dopaminergic neurons in the midbrain that control reward and (iii) use a combinatorial activation scheme to regulate feeding behavior.

Data were analyzed by 2 way Anova with with Sidak's multiple comparisons. * or # indicates P<0.05,  or ## indicates P<0.01, * or ### indicates P<0.001, **** or #### indicates P<0.0001 between treated and untreated groups.

Figure 11A:
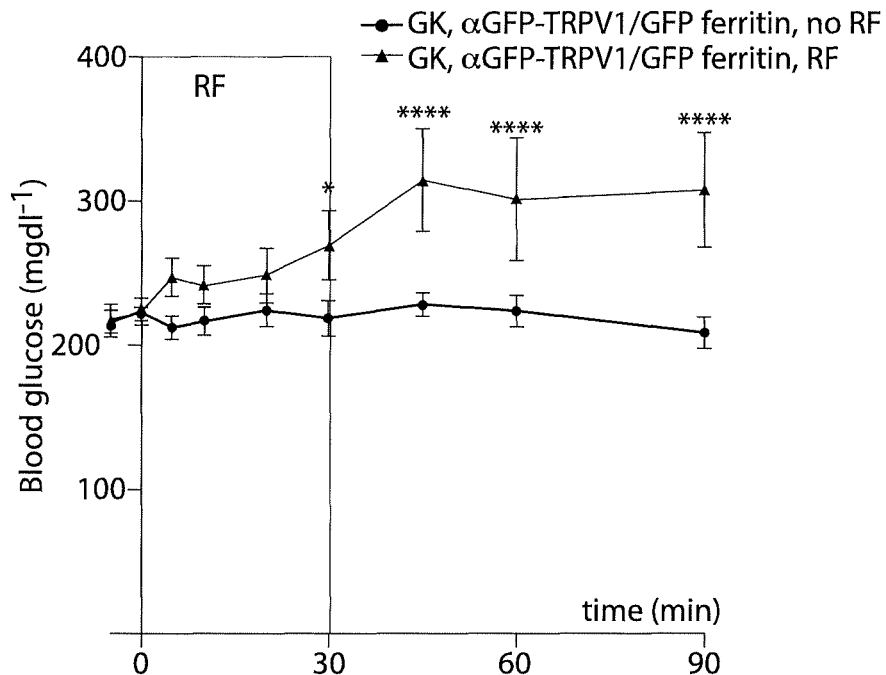

FIG. 11A is a graph showing that RF treatment of glucokinase-cre (GK-cre) mice expressing αGFP-TRPV1/GFP-ferritin in the ventromedial hypothalamus (VMH) significantly increases blood glucose compared to no RF treatment (n=13). Data points indicate mean and error bars indicate SEM. Data were analyzed by 2 way Anova with Sidak's multiple comparisons. * indicates P<0.05,  indicates P<0.01, * indicates P<0.001, **** indicates P<0.0001 between treated and untreated groups.

Figure 11B:
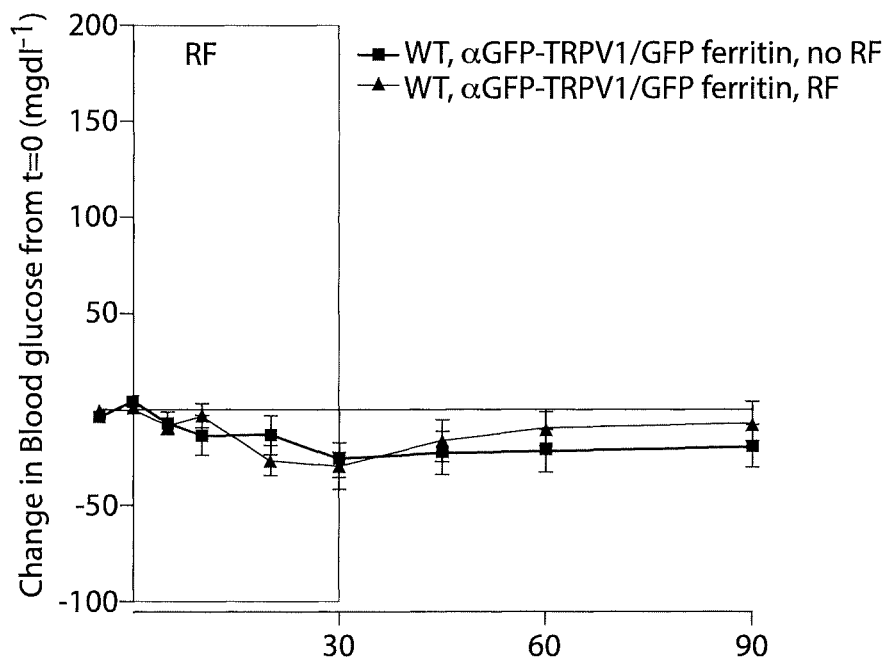

FIG. 11B is a graph showing the effects of RF treatment of wild type mice injected with αGFP-TRPV1/GFP-ferritin in the ventromedial hypothalamus (VMH) on changes in blood glucose with time (n=10). Data points indicate mean and error bars indicate SEM. Data were analyzed by 2 way Anova with Sidak's multiple comparisons.

Figure 11C:
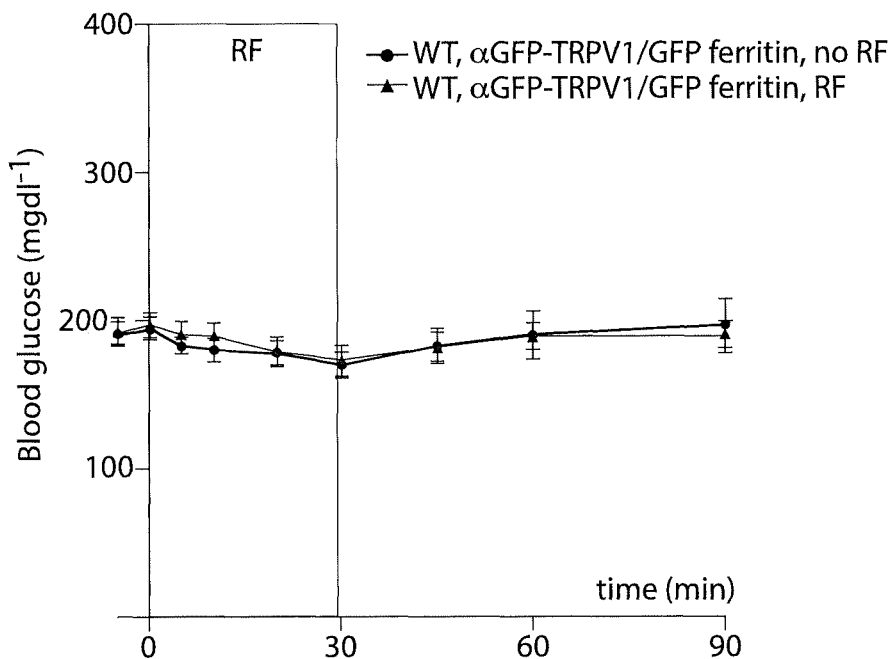

FIG. 11C is a graph showing the effects of RF treatment of wild type mice injected with αGFP-TRPV1/GFP-ferritin in the ventromedial hypothalamus (VMH) on blood glucose with time (n=10). Data points indicate mean and error bars indicate SEM. Data were analyzed by 2 way Anova with Sidak's multiple comparisons.

Figure 11D:
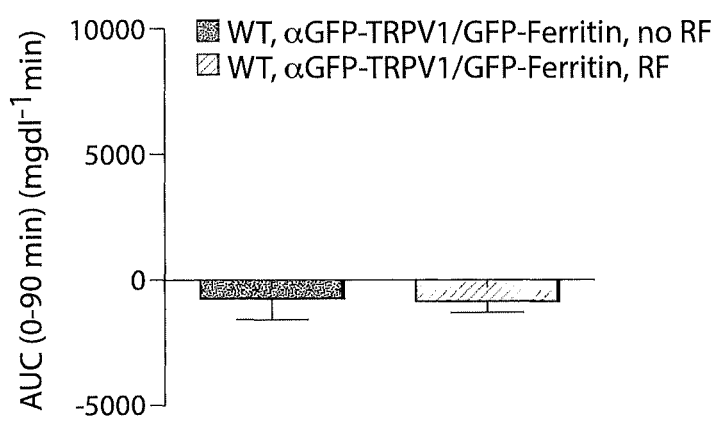

FIG. 11D is a graph showing the effect of RF treatment on blood glucose over the course of the study in WT mice with VMH injection of αGFP-TRPV1/GFP-ferritin (n=10). Columns represent mean and error bars indicate SEM. Data were analyzed by two-tailed, paired Student's t-test.

Figure 12A:
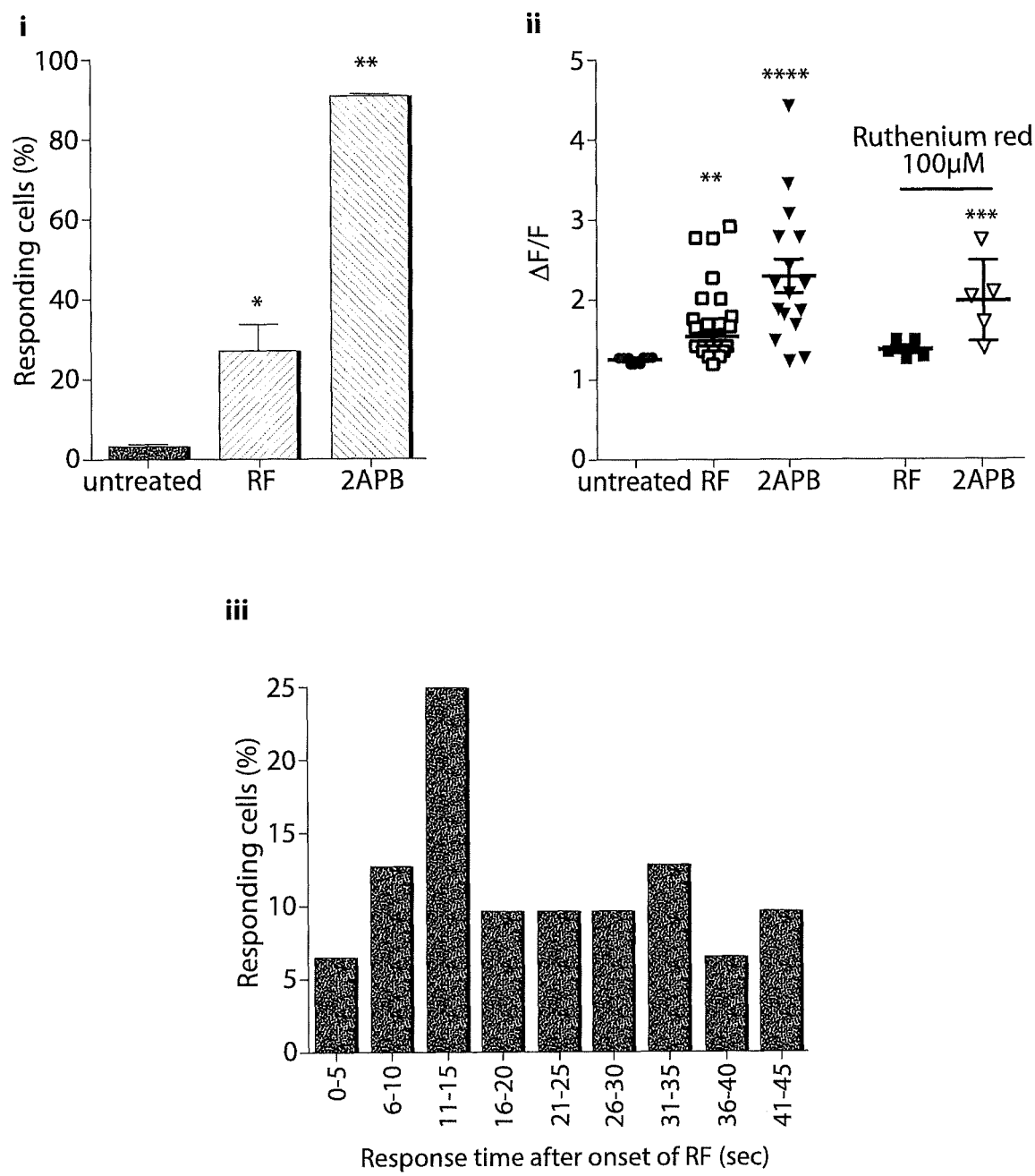

FIG. 12A presents graphs with the results of calcium imaging of RF treated N38 cells expressing αGFP-TRPV1/GFP-ferritin showing i) the percentage of cells responding (>20% increase in fluorescence) to no treatment, RF or 2APB (n=8, 9 or 2 occasions respectively), ii) the increase in fluorescent signal with RF or 2APB treatment that is inhibited by Ruthenium red and iii) the response time (to reach 20% increase in fluorescence) to RF treatment. Data is represented as mean and error bars indicate SEM. Data were analyzed by Kruskal Wallis test with Dunn's multiple comparison test. * indicates P<0.05 vs. untreated,  indicates P<0.01 vs. untreated, * indicates P<0.001 vs. untreated and **** indicates P<0.0001 vs. untreated.

Figure 12B:
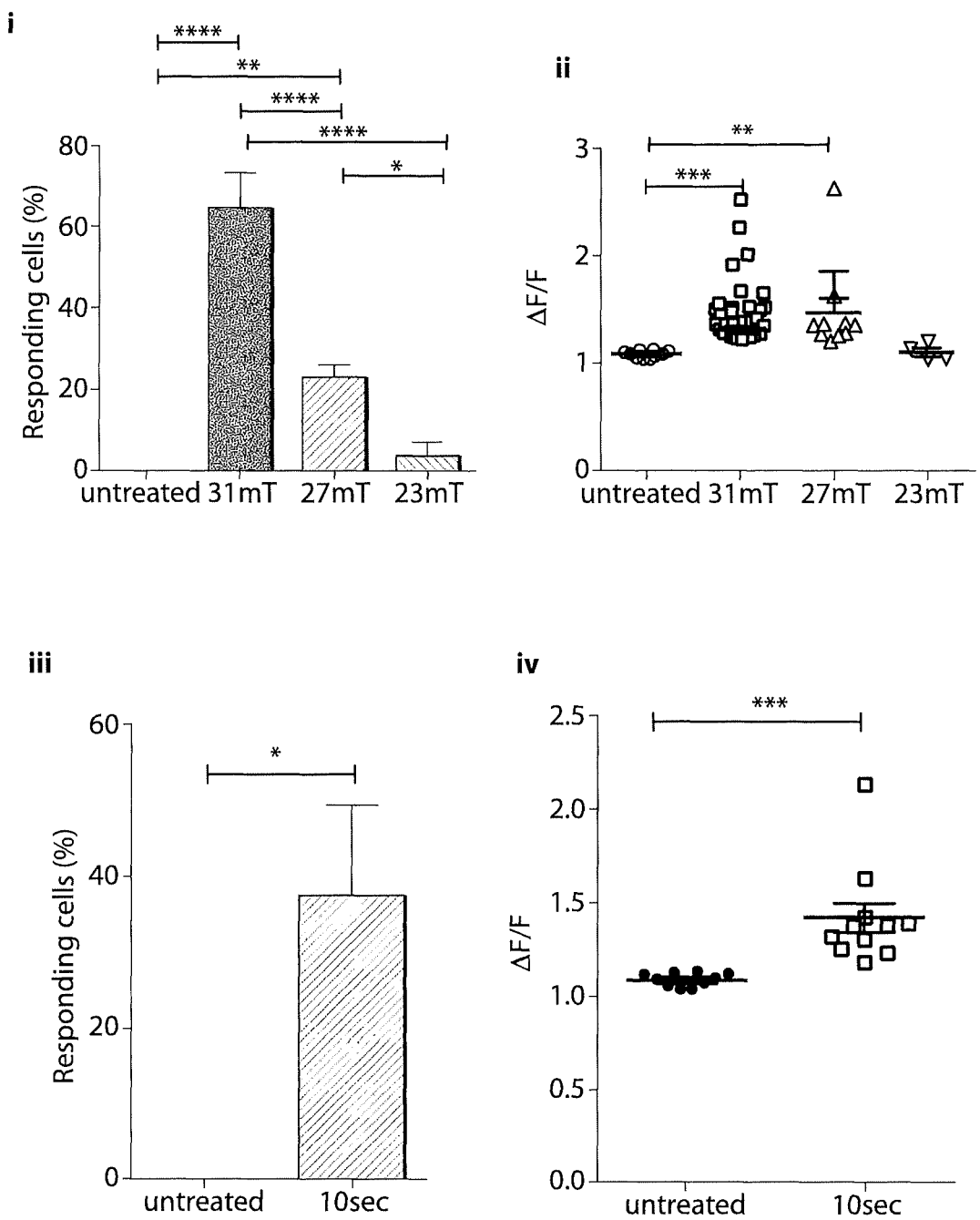

FIG. 12B presents graphs showing that calcium imaging in stably transfected N38 cells expressing αGFP-TRPV1/GFP-ferritin demonstrates a field strength dependent increase in (i) the percentage of responding cells (>20% increase in fluorescence) and (ii) the fluorescent signal in compared to untreated cells. Data points indicate mean and error bars indicate SEM. Data were analyzed by 2 way Anova with Sidak's multiple comparisons. * indicates P<0.05,  indicates P<0.01, * indicates P<0.001**** indicates P<0.0001 between treated and untreated groups. RF treatment of stably transfected N38 cells expressing αGFP-TRPV1/GFP-ferritin for 10 s significantly increases (iii) the percentage of responding cells and (iv) the fluorescent signal compared to untreated cells. Data points indicate mean and error bars indicate SEM. Data were analyzed by unpaired Student's t-test. * indicates P<0.05, *** indicates P<0.001 between treated and untreated groups.

Figure 12C:
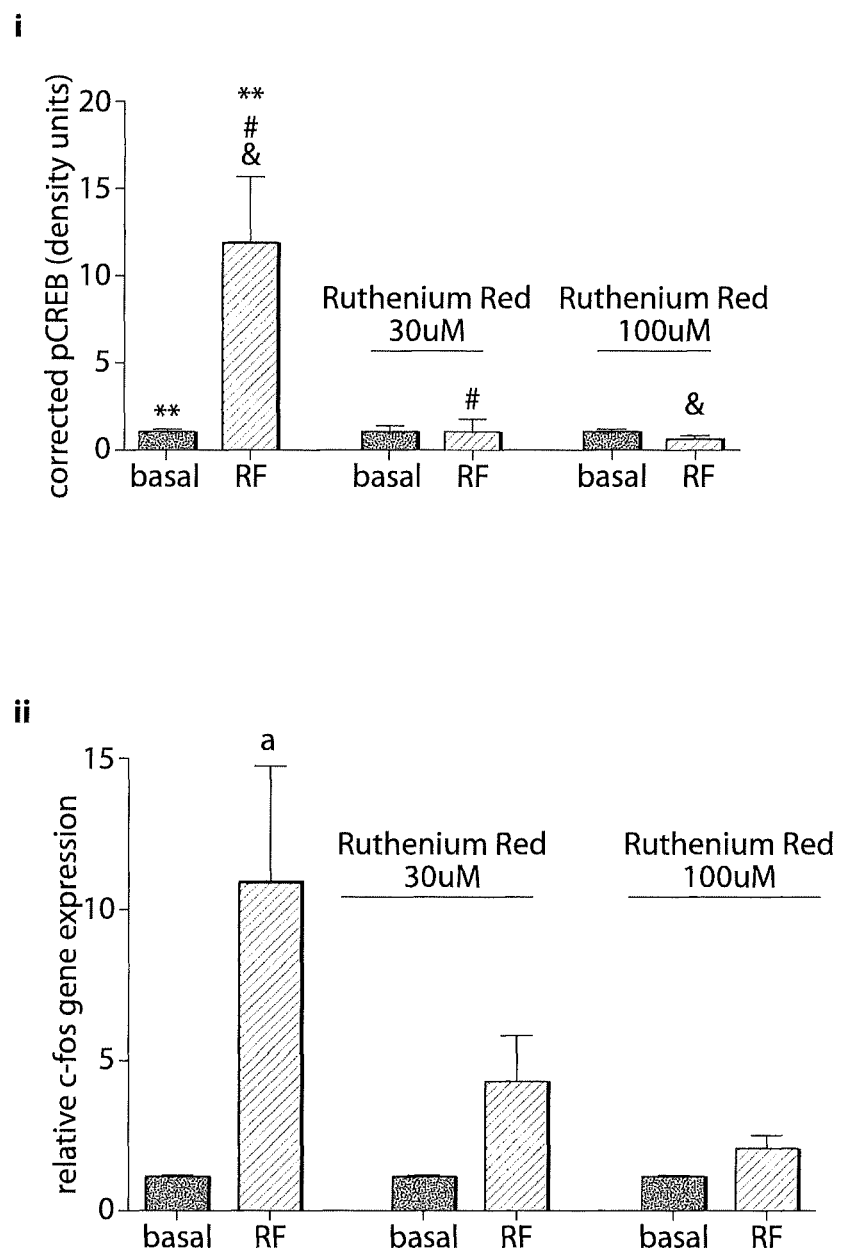

FIG. 12C presents graphs showing that RF treatment of N38 cells expressing αGFP-TRPV1/GFP-ferritin significantly increases (i) phosphoCREB levels and (ii) relative c-fos gene expression (measured by quantitative PCR) and these increases are blocked by Ruthenium red (30 and 100 μM). In all cases, columns represent mean and error bars indicate SEM. Data were analyzed by one way ANOVA with post-hoc Tukey's analysis test. Columns marked with **, #, a or & indicate P<0.01. Each study was repeated on 3 occasions each with 4 replicates.

Figure 12D:
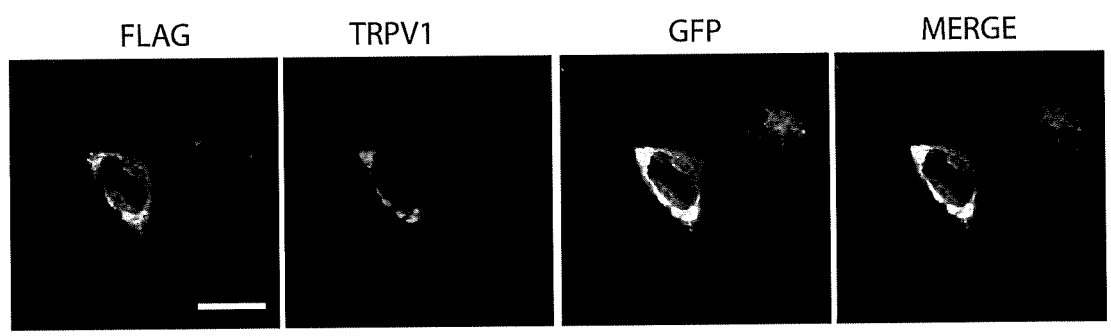

FIG. 12D presents immunohistochemistry for TRPV1 (blue), GFP (green) and FLAG-tagged ferritin chimera (red) in N38 cells infected with adenovirus expressing αGFP-TRPV1/GFP-ferritin. Scale bar represents 20 m.

Figure 12E:
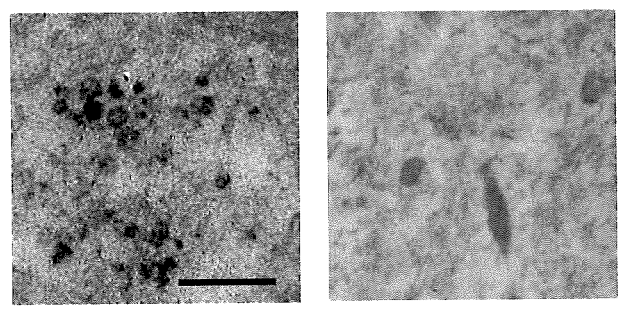

FIG. 12E presents immunoelectron microscopy images from hypothalamic sections taken from GK-cre mice with unilateral expression of αGFP-TRPV1/GFP-ferritin showing GFP tagged ferritin (left) from the injected side which are absent on the uninjected side (right). Scale bar represents 250 nm.

Figure 13A:
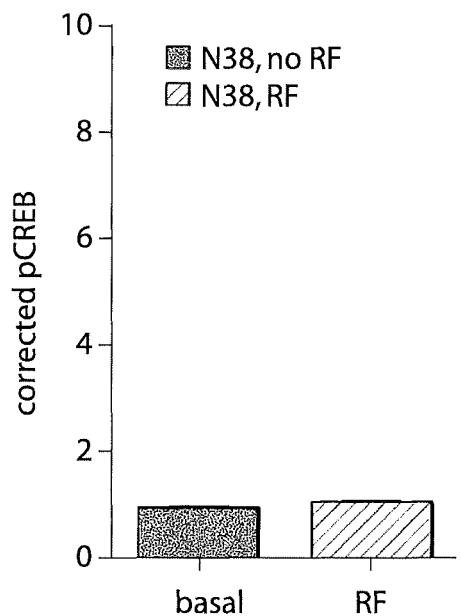

FIG. 13A is a graph showing that RF treatment of N38 cells does not alter phosphoCREB levels. In all cases, columns represent mean and error bars indicate SEM. Each study was repeated on 3 occasions each with 4 replicates.

Figure 13B:
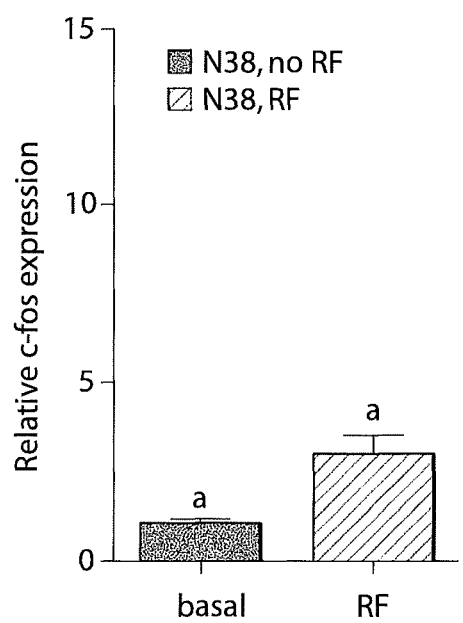

FIG. 13B is a graph showing that RF treatment significantly increases relative c-fos gene expression. In all cases, columns represent mean and error bars indicate SEM. Data were analyzed by two-tailed, unpaired Student's t-test. Columns marked with * indicate P<0.05. Each study was repeated on 3 occasions each with 4 replicates.

Figure 14A:
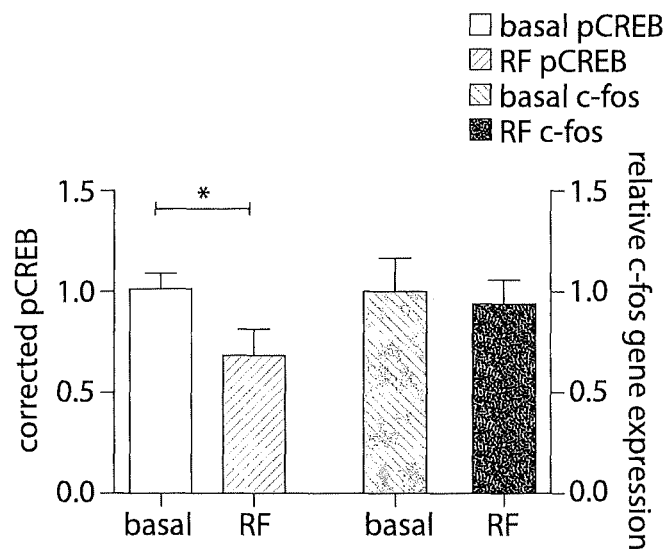

FIG. 14A is a graph showing the effect of RF treatment of N38 cells expressing αGFP-TRPV1$^{Mutant}$/GFP-ferritin on pCREB levels and c-Fos expression. In all cases, columns represent mean and error bars indicate SEM. Data were analyzed by two-tailed Mann-Whitney test.* indicates P<0.05. Each study was repeated on 3 occasions each with 4 replicates.

Figure 14B:
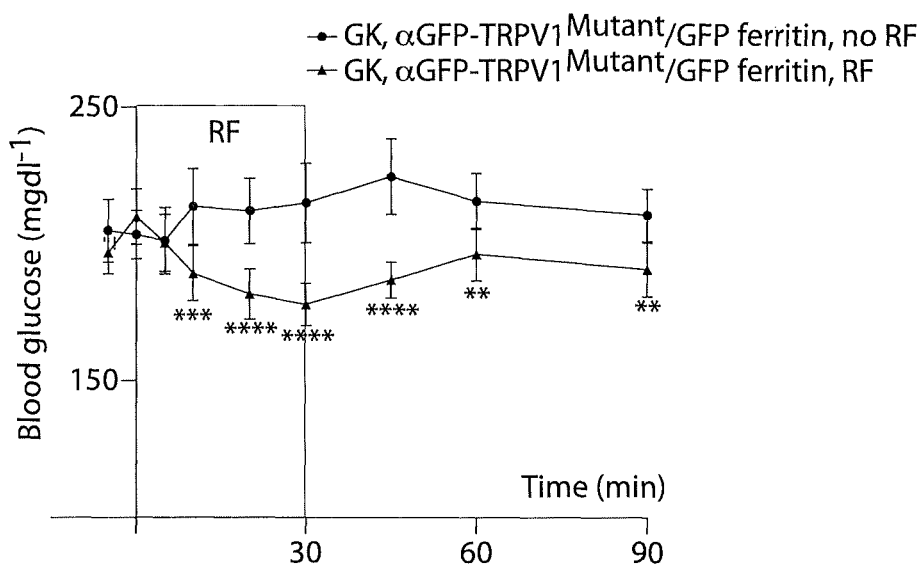

FIG. 14B is a graph showing that RF treatment of glucokinase-cre (GK-cre) mice expressing αGFP-TRPV1$^{Mutant}$/GFP-ferritin in the ventromedial hypothalamus (VMH) significantly decreases blood glucose compared to no RF treatment (n=13). Data points indicate mean and error bars indicate SEM. Data were analyzed by 2 way Anova with Sidak's multiple comparisons. * indicates P<0.05,  indicates P<0.01, * indicates P<0.001, **** indicates P<0.0001 between treated and untreated groups.

Figure 14C:
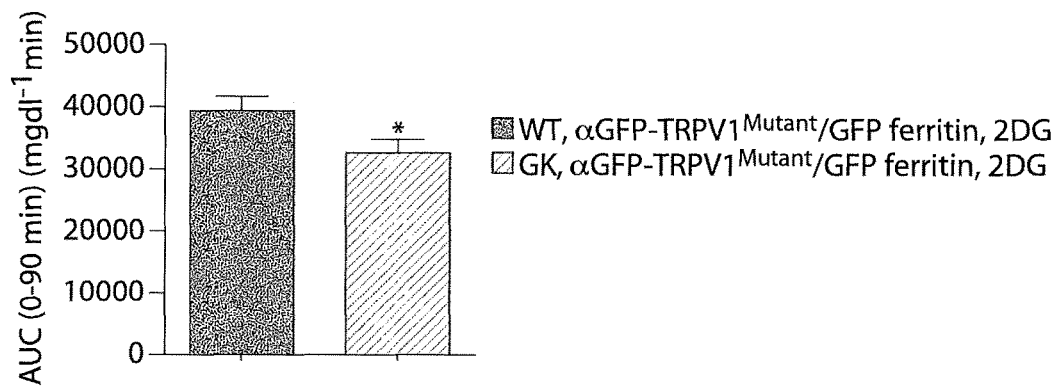

FIG. 14C is a graph showing that RF treatment significantly decreases cumulative changes in blood glucose over the course of the study in GK-cre mice with VMH expression of αGFP-TRPV1$^{Mutant}$/GFP-ferritin (n=6) compared to WT mice with VMH injection of Ad-FLEX-αGFP-TRPV1$^{Mutant}$/GFP-ferritin (n=9) after administration of 2-Deoxyglucose to mimic hypoglycemia. Data is shown as mean and error bars indicate SEM. Data were analyzed by unpaired Student's test. * indicates P<0.05.

Figure 14D:
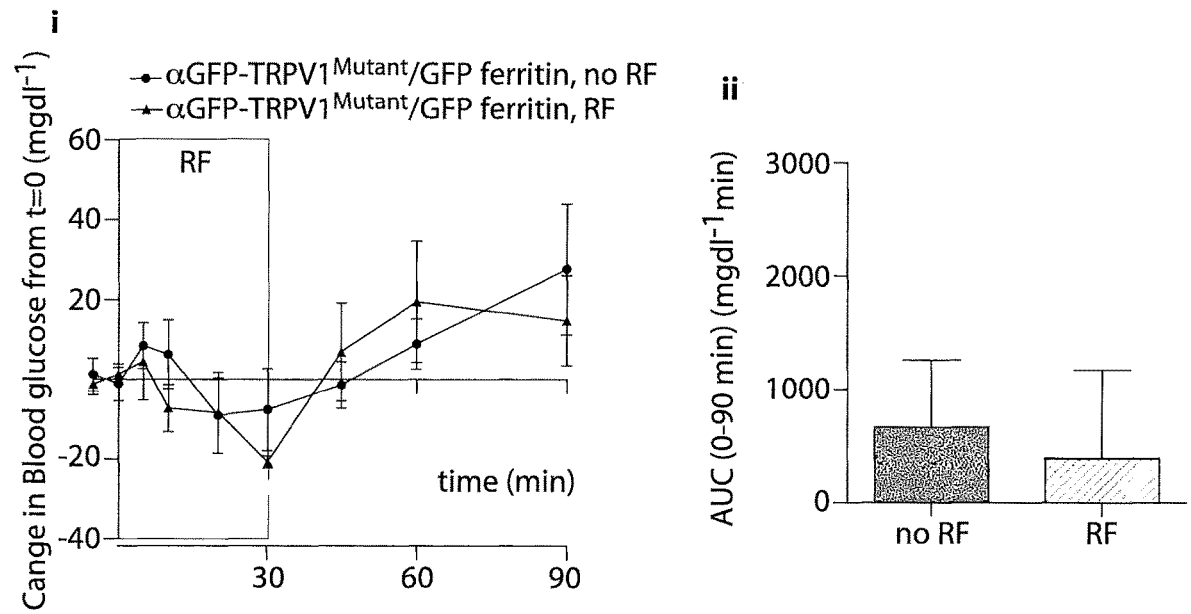
Figure 14D:
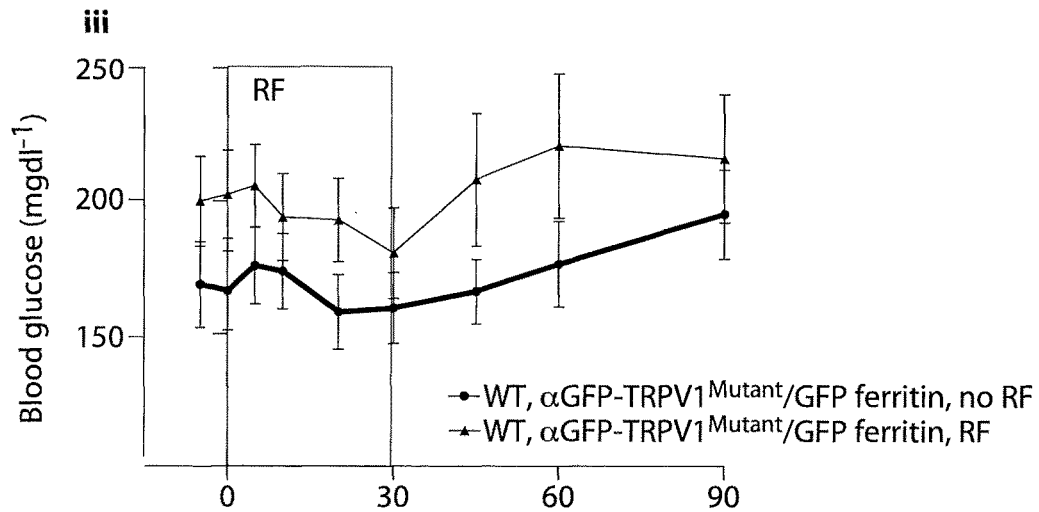

FIG. 14D presents graphs showing i) the effects of RF treatment of wild type mice injected with αGFP-TRPV1$^{Mutant}$/GFP-ferritin in the ventromedial hypothalamus (VMH) on changes in blood glucose with time (n=8). Data points indicate mean and error bars indicate SEM. Data were analyzed by 2 way Anova with Sidak's multiple comparisons. ii) Effects of RF treatment of wild type mice injected with αGFP-TRPV1$^{Mutant}$/GFP-ferritin in the ventromedial hypothalamus (VMH) on cumulative changes in blood glucose with time (n=8). Data points indicate mean and error bars indicate SEM. Data were analyzed by 2 way Anova with Sidak's multiple comparisons. iii) Effect of RF treatment on blood glucose over the course of the study in WT mice with VMH injection of αGFP-TRPV1/GFP-ferritin (n=8). Columns represent mean and error bars indicate SEM. Data were analyzed by 2 way Anova with Sidak's multiple comparisons.

Figure 15A:
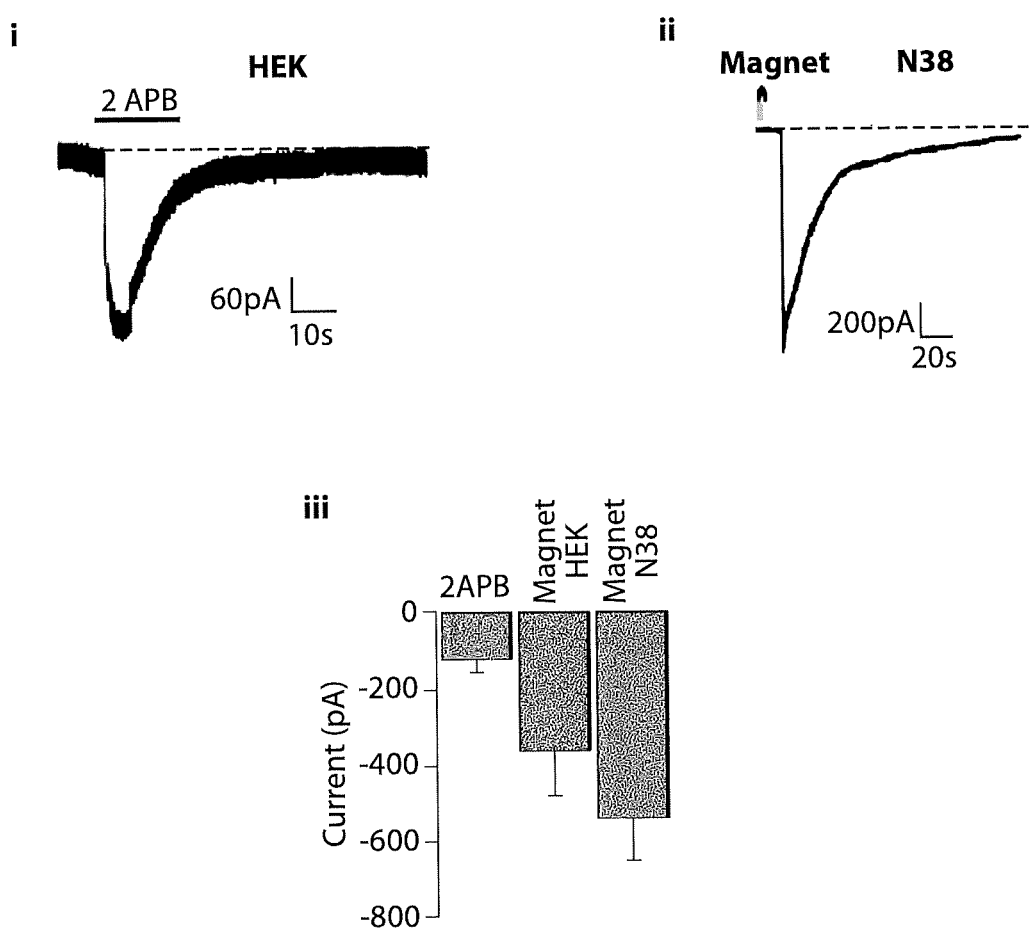

FIG. 15A presents electrophysiological recordings of cultured cells. (i) Current trace from a whole-cell voltage-clamp recording (−60 mV) showing the inward current induced with TRPV1 agonist (2APB 200 μM) in HEK cell expressing αGFP-TRPV1/GFP-ferritin. (ii) Current trace from a whole-cell voltage-clamp recording (−60 mV) induced with magnet (5s) showing the inward current in stably transfected N38 cells expressing αGFP-TRPV1/GFP-ferritin. (iii) Bar chart summary of mean peak current induced by TRPV1 agonist 2APB (200 nM) and magnet activation in cultured cells expressing αGFP-TRPV1/GFP-ferritin.

Figure 15B:
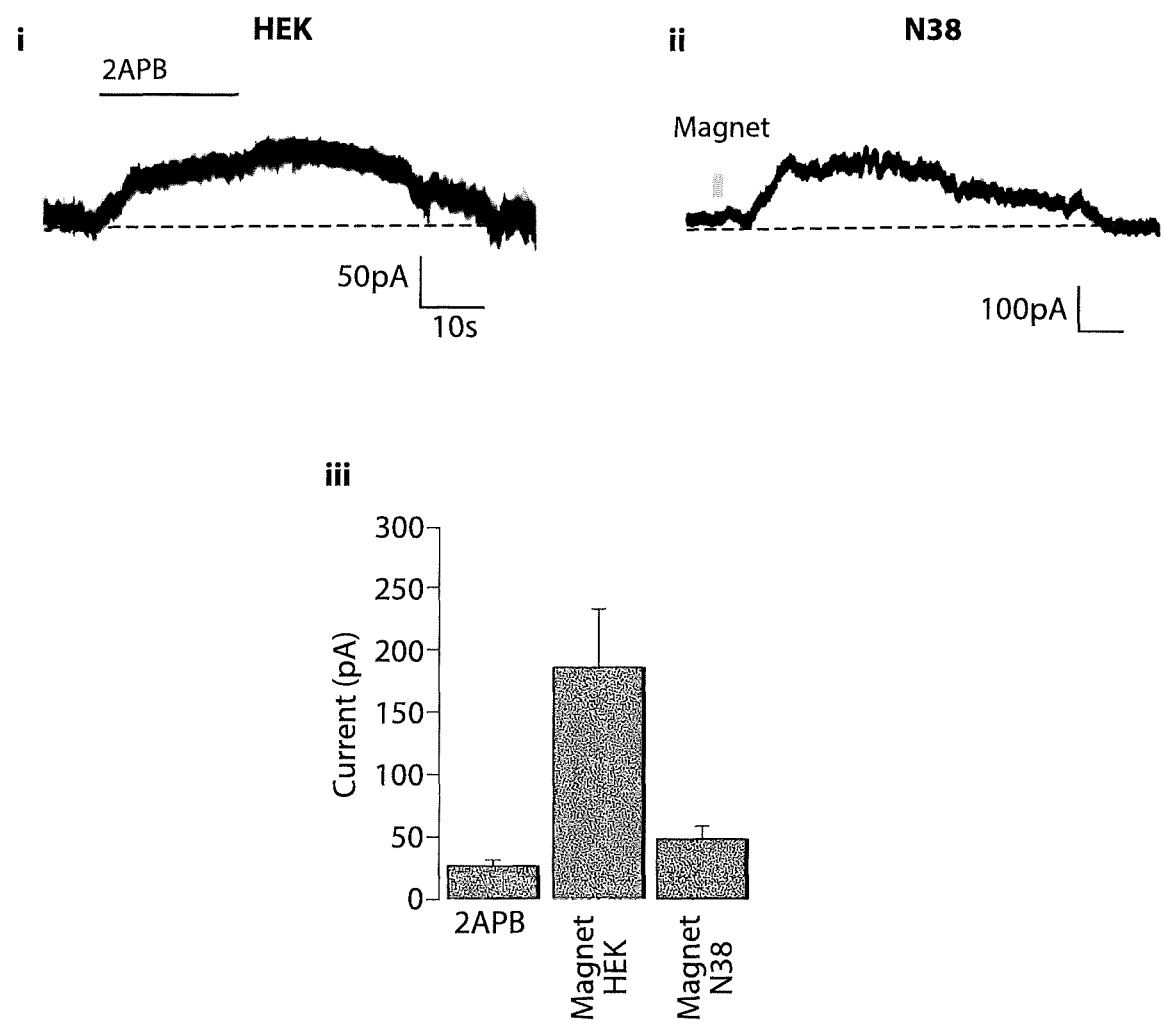

FIG. 15B presents electrophysiological recordings of cultured cells (i) Current trace from a whole-cell voltage-clamp recording (−60 mV) showing the outward current induced with TRPV1 agonist (2APB 200 μM) in HEK cell expressing αGFP-TRPV1$^{Mutant}$/GFP-ferritin. (ii) Current trace from a whole-cell voltage-clamp recording (−60 mV) induced with magnet (5s) showing the outward current stably transfected N38 cells expressing αGFP-TRPV1$^{Mutant}$/GFP-ferritin. (iii) Bar chart summary of mean peak current induced by TRPV1 agonist 2APB (200 nM) and magnet activation in cultured cells expressing αGFP-TRPV1$^{Mutant}$/GFP-ferritin.

Figure 15C:
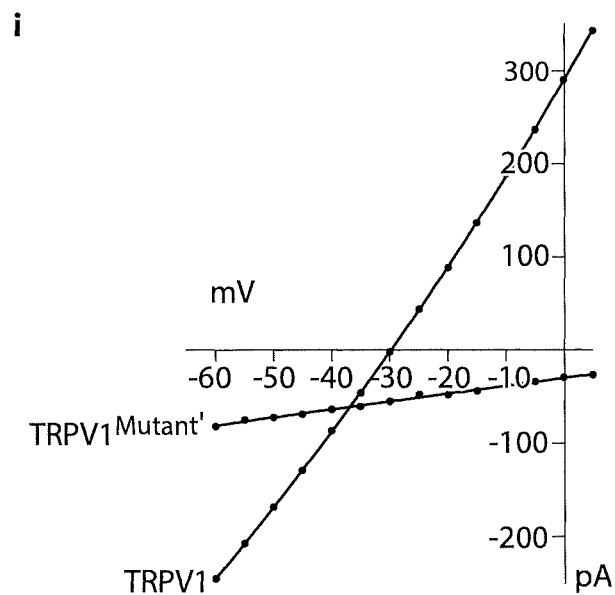
Figure 15C:
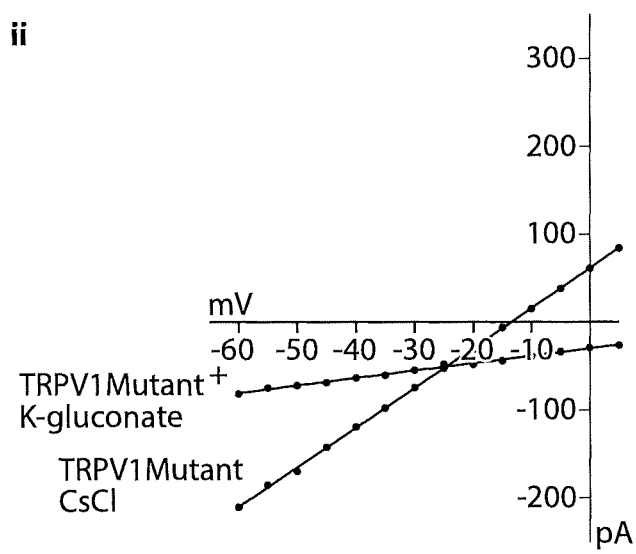

FIG. 15C presents graphs showing that Current-Voltage relationship of 2APB-activated TRPV1$^{Mutant}$ channels shows limited cation permeability and increased chloride permeability. (i) Limited conductance of TRPV1$^{Mutant}$ channels compared to wildtype when the predominant internal ions are K and gluconate. (ii) Conductance is increased for αGFP-TRPV1$^{Mutant}$ channels when the predominant internal ions are Cs and Cl (isometrical chloride).

Figure 15D:
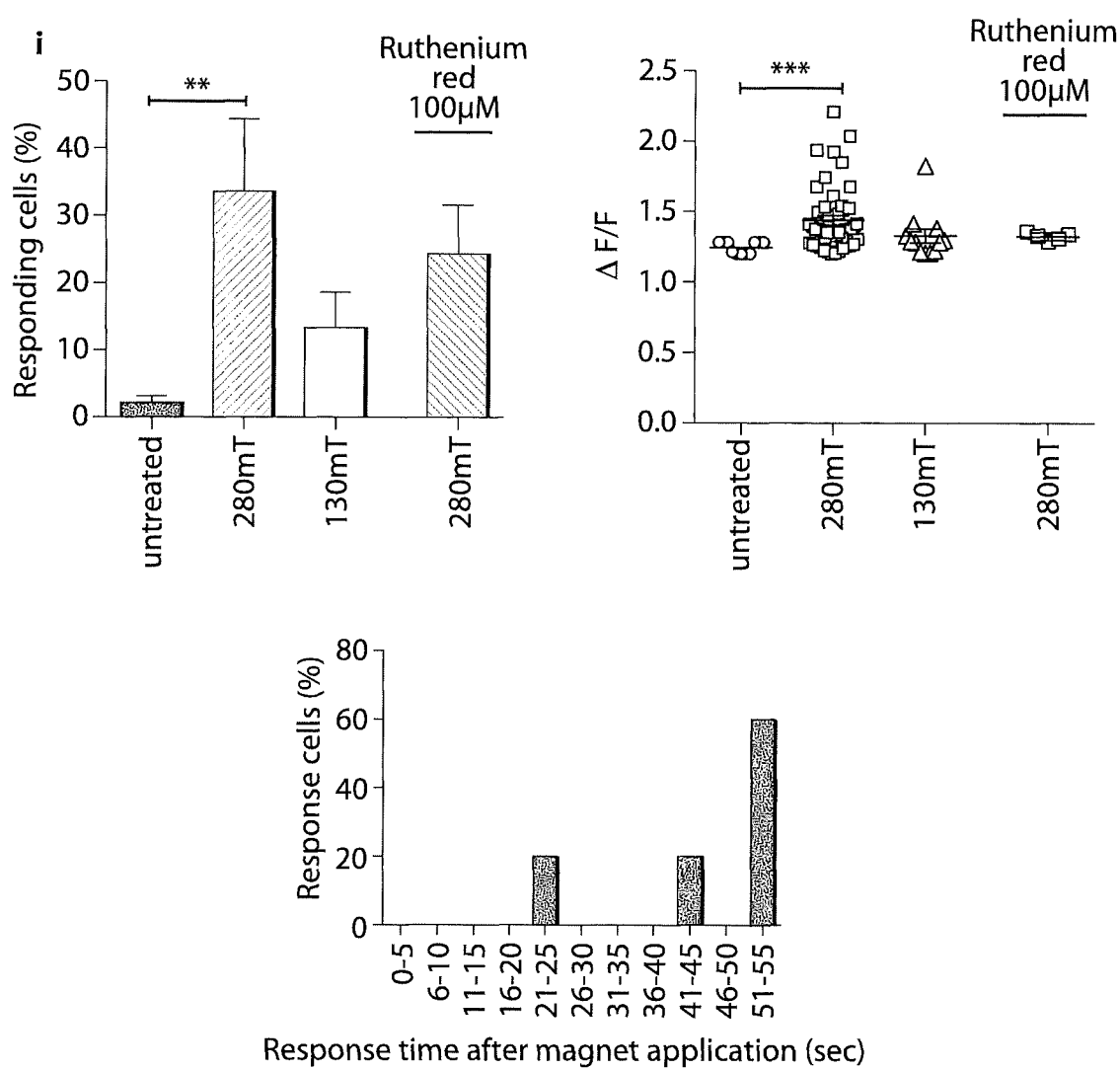

FIG. 15D presents the results of calcium imaging in stably transfected N38 cells expressing αGFP-TRPV1/GFP-ferritin demonstrates a magnetic field strength dependent increase in (i) the percentage of responding cells (>20% increase in fluorescence) and (ii) the fluorescent signal compared to untreated cells. The effects of magnet stimulation were blocked by Ruthenium red. Data points indicate mean and error bars indicate SEM. Data were analyzed by 2 way Anova with Sidak's multiple comparisons. * indicates P<0.05,  indicates P<0.01, * indicates P<0.001**** indicates P<0.0001 between treated and untreated groups. (iii) Histogram representing the response time (to reach 20% increase in fluorescence) in magnet treated N38 cells expressing αGFP-TRPV1/GFP-ferritin.

Figure 15E:
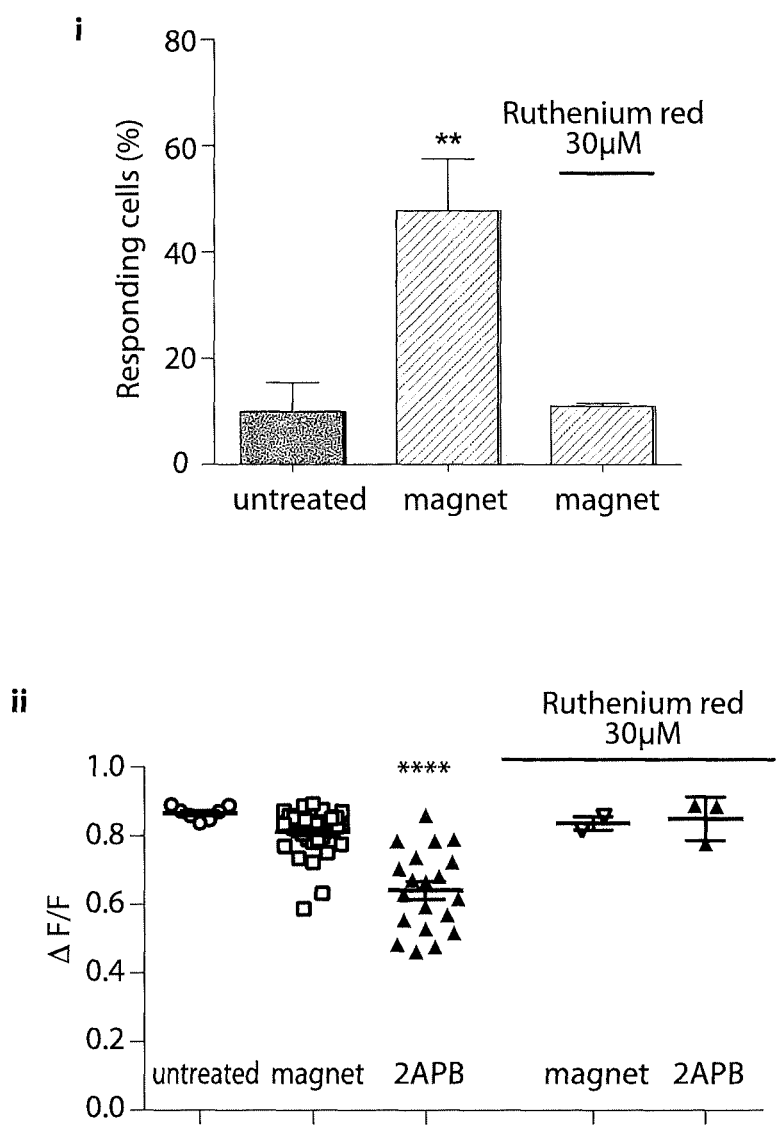

FIG. 15E presents graphs showing that treatment of N38 cells expressing αGFP-TRPV1$^{Mutant}$/GFP-ferritin with magnet (n=6 occasions) significantly increased i) the percentage of responding cells (>10% decrease in chloride indicator, MQAE, fluorescence) compared to untreated cells (n=4 occasions) and ii) the reduction in MQAE signal. Ruthenium red reduced both the percentage of responding cells and the magnitude of the response (n=2 occasions). In all cases, columns represent mean and error bars indicate SEM. Data were analyzed by Kruskal Wallis test with Dunn's multiple comparison test. Columns marked with  indicate P<0.01 vs. untreated, columns marked with ** indicate P<0.001 vs. untreated.

Figure 16A:
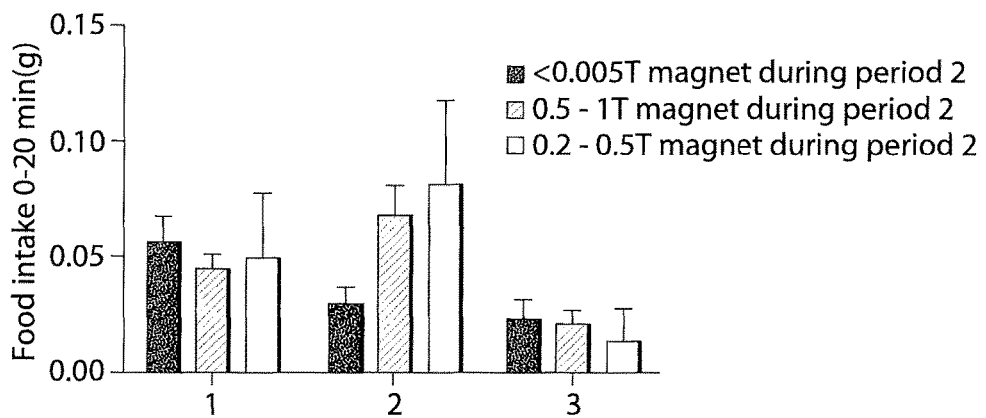

FIG. 16A is a graph showing the effect of moderate (0.2-0.5 T) magnetic field strength on food intake in GK-cre mice expressing αGFP-TRPV1/GFP-ferritin in the VMH.

Figure 16B:
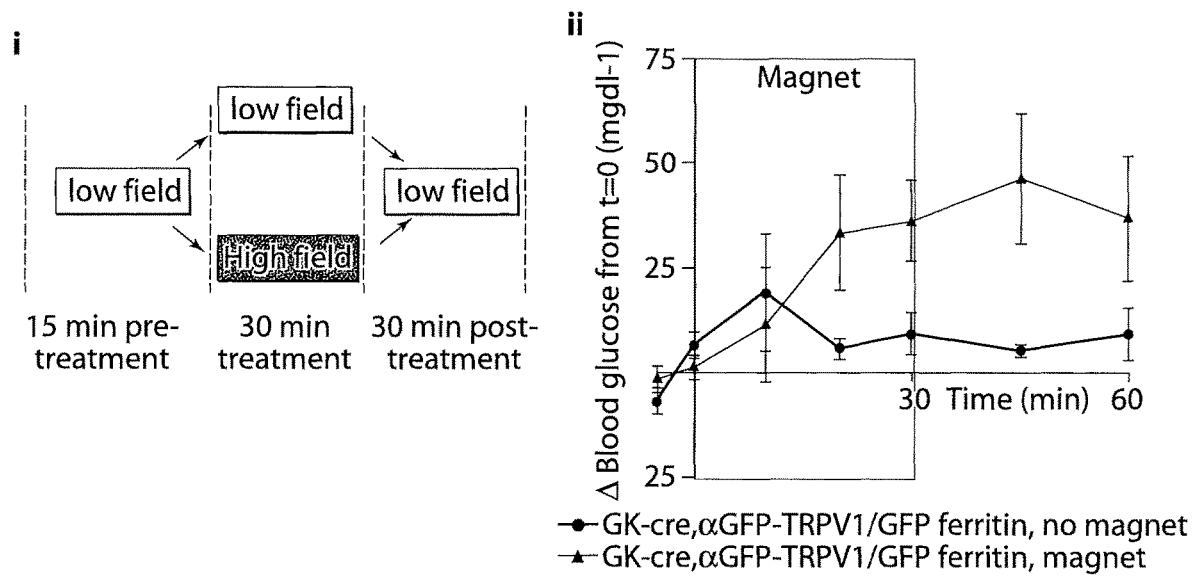

FIG. 16B shows (i) a schema of the cross-over protocol used to examine the effect of neural activation with a static magnetic field on blood glucose. ii) Magnetic field treatment of glucokinase-cre (GK-cre) mice expressing αGFP-TRPV1/GFP-ferritin in the ventromedial hypothalamus (VMH) significantly increases blood glucose compared to no magnet treatment (n=6). Data points indicate mean and error bars indicate SEM. Data were analyzed by 2 way Anova with Sidak's multiple comparisons. iii) Magnet treatment significantly increases cumulative change in blood glucose over the course of the study in GK-cre mice with VMH expression of αGFP-TRPV1/GFP-ferritin (n=6) compared to the same mice without magnet treatment. In all cases, columns represent mean and error bars indicate SEM. Data were analyzed by Wilcoxon matched pairs signed rank test. * indicates P<0.05.

Figure 16C:
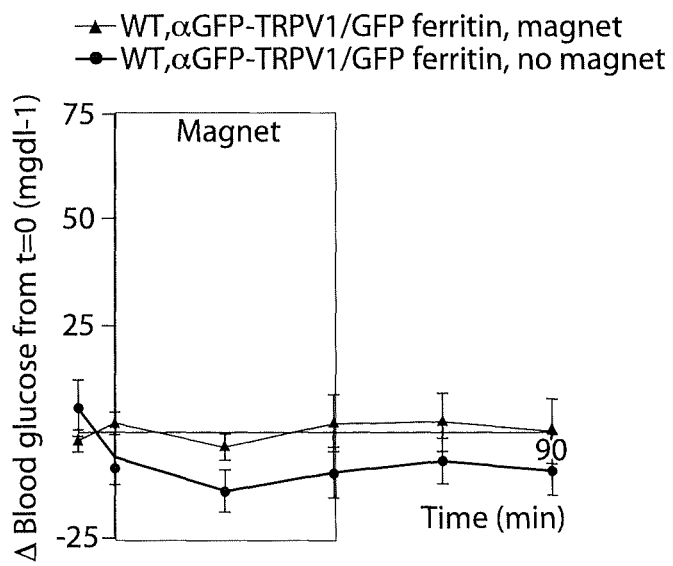
Figure 16C:
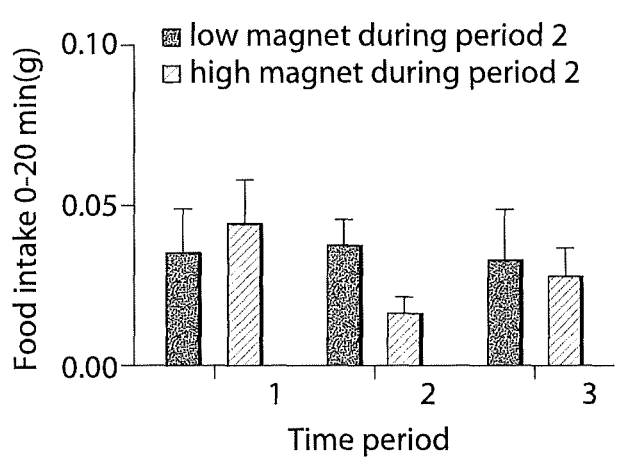

FIG. 16C presents graphs showing (i) Effects of static magnetic field treatment of wild type mice injected with αGFP-TRPV1/GFP-ferritin in the ventromedial hypothalamus (VMH) on changes in blood glucose with time (n=6). Data points indicate mean and error bars indicate SEM. Data were analyzed by 2 way Anova with Sidak's multiple comparisons. (ii) Effects of static magnetic field treatment of wild type mice injected with αGFP-TRPV1/GFP-ferritin in the ventromedial hypothalamus (VMH) on food intake (n=6). Data points indicate mean and error bars indicate SEM. Data were analyzed by 2 way Anova with Sidak's multiple comparisons.

Figure 17A:
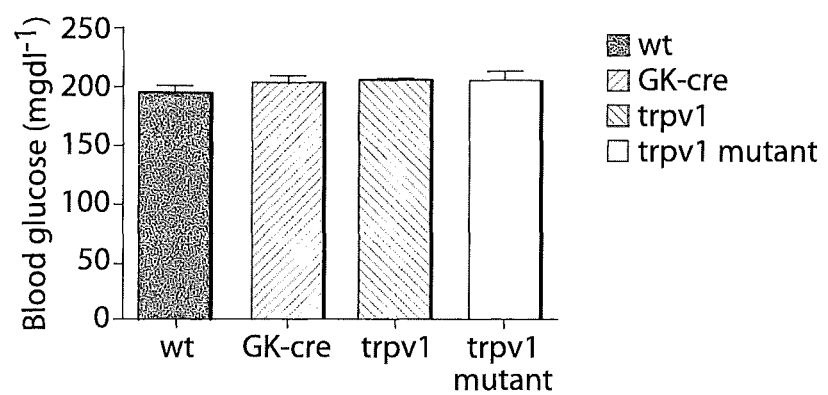

FIG. 17A is a graph showing that non-fasting blood glucose did not differ significantly between WT, GK-cre, GK-cre mice injected with αGFP-TRPV1/GFP-ferritin or αGFP-TRPV1$^{Mutant}$/GFP-ferritin.

Figure 17B:
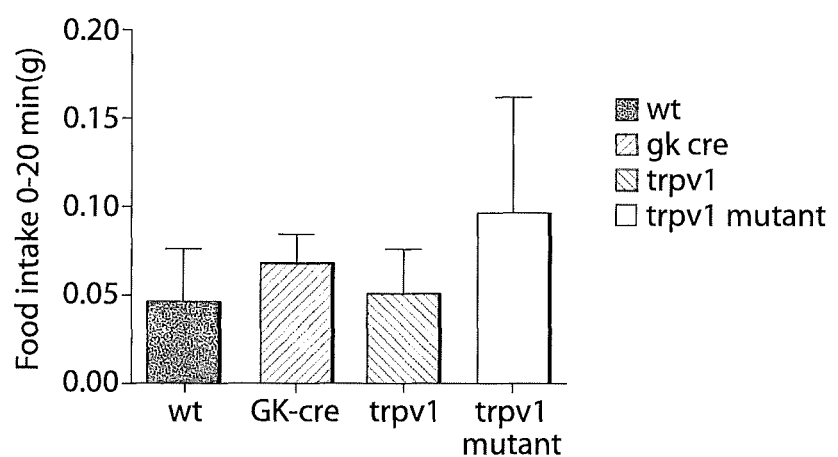

FIG. 17B is a graph showing that food intake following a 4 hour fast did not differ significantly between WT, GK-cre, GK-cre mice injected with αGFP-TRPV1/GFP-ferritin or αGFP-TRPV1$^{Mutant}$/GFP-ferritin.

FIG. 18 shows the amino acid sequence of rat I679K-TRPV1 (SEQ ID NO:1).

DETAILED DESCRIPTION OF THE INVENTION

The present invention provides methods and compositions for the remote control of cell function based on the use of radiofrequency waves or a magnetic field to excite paramagnetic nanoparticles expressed in specific cell types. The cell type of interest expresses an ion channel tethered to a metal binding protein that forms paramagnetic nanoparticles, wherein excitation of the paramagnetic nanoparticles results in a physical change, such as a localized temperature increase or mechanical force that activates the ion channel and is thereby transduced into a cellular response. Such cellular responses include, for example, modulation of cell proliferation, cell differentiation, apoptosis, gene expression, activation or inhibition of one or more cellular processes and/or activation or inhibition of one or more signal transduction pathways. In certain embodiments the cells of interest are neurons.

In a specific embodiment of the invention, the cellular response is an increase in gene expression resulting in production of one or more physiologically active proteins. The expression of such proteins may be used to treat various inherited or acquired disorders including for example, cardiovascular disorders, neurological disorders, including disorders of the peripheral and central nervous systems, autoimmune diseases, oncological diseases, hormonal disorders, metabolic diseases, blood disorders or immune disorders. Additionally, the proteins may be expressed to treat various infectious diseases including, for example, viral, bacterial, parasitic, and fungal infections. The cellular response resulting from nanoparticle excitation may also be designed to result in an increase in gene expression resulting in production of one or more nucleic acid molecules of interest. Such nucleic acid molecules include those molecules capable of regulating protein expression, such as antisense and siRNA molecules.

The compositions and methods of the invention utilize a metal binding protein. As used herein, the term "metal binding protein" is a protein which is associated with paramagnetic metal containing nanoparticles. Metal binding proteins can, for example, form such nanoparticles following expression in cells. Suitable metal binding proteins include ferritin, ferritin variants, bacterial magnetic particles, such as MagA and Mms, bacterioferritin, DNA binding protein from starved cells (Prozorov, et al., *Adv. Funct. Mater.* 2007, 17:951-957; Zeth, K., *Biochem J.* 2012, 445: 297-311) and others known in the art. Preferably the metal binding protein is ferritin, such as a mammalian, particularly human, ferritin, or a ferritin variant. Ferritin is a heteromultimeric protein comprising light and heavy chains, which creates a 5 to 12 nm iron oxide core with a complex crystalline and magnetic structure.

The genetic constructs of the invention comprise a nucleotide sequence which encodes the metal binding protein, such as ferritin or a ferritin variant, fused to a first polypeptide. The genetic construct further comprises a nucleotide sequence which encodes an ion channel fused to a second polypeptide. Preferably, the first polypeptide is a binding partner of the second polypeptide. In one embodiment, the nucleotide sequences are DNA sequences, preferably double stranded DNA sequences, which encode the fusion proteins.

In one embodiment, the second polypeptide comprises an epitope, and the first polypeptide is an antibody which binds the epitope. In a preferred embodiment, the first polypeptide comprises an epitope, and the second peptide or protein is an antibody which binds the epitope.

The polypeptide comprising the epitope can be limited to the epitope itself or a polypeptide which comprises the epitope. The epitope can be a linear or nonlinear epitope, but is preferably a linear epitope.

The antibody can be a human, murine or other mammalian antibody, or a humanized antibody. The antibody can be multimeric or monomeric, such as a single chain antibody. In a preferred embodiment, the antibody is a camelid antibody or a single domain antibody produced from a camelid heavy chain antibody.

The first and second polypeptides can comprise any suitable epitope/antibody pair. In certain embodiments, the epitope/antibody pair is selected from, but not limited to, green fluorescent protein (GFP)/anti-GFP antibody; enhanced green fluorescent protein (EGFP)/anti-GFP antibody; FLAG/anti-FLAG antibody; polyHis/anti polyHis antibody; Myc/antiMyc antibody; hemaglutinin/antihemaglutinin antibody and others as are known in the art. Preferred genetic constructs of the invention include up to about 5 kilobases.

The vector of the invention comprises the genetic construct of the invention in a form which is suitable for transfection of cells in vitro or in vivo. Suitable vectors include plasmids, including circular and linear plasmids, liposomes, viral vectors, such as adenovirus, preferably replication deficient adenovirus, and adeno-associated virus (AAV), and others as are known in the art.

The expression system of the present invention can be used with virtually any type of biological cell population, including bacterial cells, insect cells, mammalian cells, particularly human cells. The specific cell type used will typically vary depending upon the type of cellular response that is sought to be regulated. For example, animal cells and specifically, human cells or non-human mammalian cells are typically preferred for increased expression of a physiological protein for use as a therapeutic.

In an embodiment of the invention the cell type of interest is a stem cell, preferably a mammalian stem cell. For example, stem cells engineered to express a construct of the invention can act as autografts to enable external control of cell function. As used herein, "stem cell" refers to any cell having the potential to differentiate into one or more different cell types, including pluripotent stem cells. Such cells include, but are not limited to, stem cells derived from a variety of different sources including, for example, bone marrow, embryonic blastocysts or yolk sac, spleen, blood, including peripheral blood and umbilical cord blood, adipose tissue and other tissues and organs. Such stem cells include, but are not limited to, hematopoietic stem cells, mesenchymal stem cells, endothelial progenitor cells or embryonic stem cells.

In a specific embodiment of the invention, the ion channel is a temperature sensitive ion channel, and exposing the paramagnetic nanoparticles to radiofrequency radiation results in a localized temperature increase that is transduced into a cellular response via the ion channel. Such temperature sensitive ion channels include, but are not limited to, the TRPV1, TRPV2, TRPV3, TRPM8, TRPV4, TRPVA1, chimeric TRP channels, TREK-2 and tandem pore domain potassium channels, such as TREK1, TREK2, and TASK. For example, when the channel is TRPV1, the localized temperature increase mediated by the excitation of the paramagnetic nanoparticles leads to an activation of the channel resulting in gating of $Ca^{2+}$ entry. The ion channels can be derived from any animal or plant species, but are preferably of mammalian and more preferably of human origin.

In one embodiment, the temperature sensitive ion channel is a cation channel, such as a calcium or sodium channel.

In another embodiment, the temperature sensitive ion channel is an anion channel, such as a chloride channel. In one embodiment, the ion channel is $TRPV1^{Mutant}$. Mutation of Ile 679 of the rat calcium channel TRPV1, or the corresponding Ile residue in another mammalian TRPV1, to Lys results in a mutant channel that gates chloride rather than calcium. Thus, the genetic construct of the invention can encode $TRPV1^{Mutant}$ in embodiments in which a chloride channel is desired. Further, the invention provides $TRPV1^{Mutant}$ protein, nucleotide sequences which encode this mutant protein, vectors comprising these nucleotide sequences, optionally operably linked to a promoter sequence, and recombinant cells comprising such nucleotide sequence.

In another embodiment of the invention, the ion channel is a mechanosensitive ion channel, and exposing the paramagnetic nanoparticles to a magnetic field results in motion of the nanoparticles than is transduced into a cellular response via activation of the ion channel. Such mechanosensitive ion channels include, but are not limited to TRPC1, TRPC3, TRPC6, TRPM4, TRPM7, TRPN1, TRPA1, TRPY1, TRPP1, TRPP2, TRPV1, 1679K-TRPV1, TRPV2, TRPV4, TREK, TRAAK, Piezo, ASIC1,2,3, MEC-4/MEC-10, MscL, MscS and others as are known in the art. The localized nanoparticle motion increase leads to an activation of the channel resulting in modulation of cell activity. For example, when the channel is TRPV1, the movement of the paramagnetic nanoparticles leads to an activation of the channel resulting in gating of $Ca^{2+}$. Conversely, when the channel is the I679K version of TRPV1, the movement of the paramagnetic nanoparticles leads to an activation of the channel resulting in gating of $Cl^-$.

The ion channel encoded by the genetic constructs of the invention can be derived from any animal or plant species, but is preferably of mammalian and more preferably of human origin.

In an embodiment, the invention provides a method of producing a protein, peptide or nucleic acid comprising the steps of (1) providing a population of recombinant cells which comprise a genetic construct of the invention and further comprise a nucleotide, such as a DNA sequence, encoding the protein, peptide or nucleic acid of interest operably linked to a promoter which is induced by activation of the ion channel; (2) exposing the cells to radiofrequency radiation or to a magnetic field, thereby inducing the cells to produce the protein, peptide or nucleic acid of interest; and (3) isolating the protein, peptide or nucleic acid of interest.

In certain embodiments of the methods of the invention, the method of producing the recombinant cells ex vivo or transducing host cells in vivo further comprises the step of providing a source of iron to the cells. For example, in certain embodiments, the target cells are in the central nervous system and a source of iron ions is administered to the central nervous system, for example to the cerebrospinal fluid. The iron source can be any physiologically acceptable source of iron ions as are known in the art, such as an Fe(II) or Fe(III) salt.

In certain embodiments, the recombinant cells are used to establish a cell bank which can produce the desired product on an industrial scale. In one embodiment, the recombinant cells are grown in cell culture. In an embodiment, the cells are maintained in a bioreactor under suitable conditions for growth of the cells. Preferably, the radiofrequency radiation or the magnetic field is administered at specified points in the growth cycle of the cells to optimize protein production.

In one embodiment, the present invention provides methods of administering a protein, peptide or nucleic acid having therapeutic or prophylactic activity to a subject in need thereof. In one embodiment, the method comprises the steps of (1) administering to the subject an effective amount of the recombinant cells of the invention, wherein said cells can be induced to express the therapeutic protein, peptide or nucleic acid upon exposure to radiofrequency radiation or a magnetic field; and (2) exposing the subject to radiofrequency radiation or a magnetic field under conditions which induce expression of the protein, peptide or nucleic acid, thereby administering the protein, peptide or nucleic acid to the subject.

In another embodiment, the method comprises the steps of (1) administering to the subject a vector of the invention, wherein said vector comprises a genetic construct of the invention and (2) exposing the subject to radiofrequency radiation or a magnetic field under conditions which induce expression of the protein, peptide or nucleic acid, thereby administering the protein, peptide or nucleic acid to the subject.

In the methods of the invention for producing or administering a protein, peptide or nucleic acid, the protein, peptide or nucleic acid of interest is encoded by a gene which is activated upon activation of the channel. The gene encoding the protein or peptide of interest can be, for example, an endogenous gene the expression of which is dependent upon the ion gated by the ion channel or a recombinant gene operably linked to a regulatory sequence which is activated by the ion gated by the ion channel. For example, when the ion channel is a calcium channel, the protein or peptide of interest can be encoded by a $Ca^{2+}$-dependent endogenous gene or a recombinant gene which is operably linked to a $Ca^{2+}$ dependent promoter.

In certain embodiments, methods of the invention include the treatment of a subject having a disease which can be treated with the protein, peptide or nucleotide having therapeutic or prophylactic activity.

In one embodiment, the invention provides a method of treating a disease or disorder characterized by a deficiency in the production of an active protein or peptide. For example, the method can be used to treat diseases which are characterized by a deficiency of peptide hormone or an enzyme, such as a lysosomal storage disorder. Examples include, but are not limited to, the following diseases where the therapeutic protein or peptide for the disease follows in parentheses: type 1 and type II diabetes (insulin/proinsulin); anemia (erythropoietin); G-CSF (neutropenia); Pompe disease (alpha-glucosidase), Gaucher's disease (glucocerebrosidase), Fabry disease (alpha-galactosidase A), mucopolysaccharidoses (alpha-L-iduronidase, iduronate sulfatase, heparan sulfamidase, N-acetylglucosamidase, heparan-alpha-glucosamidine 6-sulfatase, galactose-6-sulfate sulfatase, beta-galactosidase, N-acetylgalactosamine-4-sulfatase, beta-glucoronidase, hyaluronidase), hemophilia A (Factor XIII), hemophilia B (Factor IX), Rett syndrome (mythyl-CpG-binding protein 2, MeCP2), retinal neovascularization (anti-VEGF), rheumatoid arthritis (anti-TNF), inflammatory bowel disease (anti-TNF).

In one embodiment, activation of the ion channel induces expression or increased expression of an endogenous gene encoding a protein or peptide of interest. For example, expression of the gene can be induced or increased by an ion gated by the ion channel. When the channel is a calcium channel, for example, the gene can be any endogenous gene regulated by a calcium sensing pathway, such as serum response element, cAMP response element, or NFAT response element. Endogenous calcium dependent genes include genes encoding c-fos, BDNF, Arc, Cpgl5, Homer la, class I MHC molecules. In addition, signaling pathways dependent on cell depolarization can also be activated in this way.

In another embodiment of the invention, activation of the ion channel induces expression or increased expression of a recombinant gene encoding a protein, peptide or nucleic acid of interest. In this embodiment, the recombinant cells further comprise a genetic construct comprising a nucleotide, preferably DNA, sequence which encodes at least one physiologically active protein, peptide or nucleotide of interest, such as a protein providing a therapeutic benefit. The cells are genetically engineered in such a way that expression of the protein of interest is induced in the cell upon activation of the ion channel. Alternatively, the cells may be engineered to express a non-encoding nucleic acid molecule of interest such as an antisense or siRNA molecule. In an embodiment of the invention, a recombinant expression vector designed to express the protein or peptide of interest or a nucleic acid molecule of interest, such as antisense or RNAi molecules, is introduced into the cells of choice to inhibit a specific activity.

In embodiments of the invention in which the protein, peptide or nucleic acid to be produced is encoded by a recombinant gene, the gene is present in an expression vector which, in addition to containing a nucleic acid encoding the protein or nucleic acid of interest, contains at least one transcriptional regulatory sequence that is induced upon activation of the ion channel, resulting in expression of the protein, peptide or nucleic acid molecule of interest. Such transcriptional regulatory sequences, include, but are not limited to, promoter and/or enhancer sequences that induce gene expression in response to ion channel activation. Such regulatory sequences include, but are not limited to the calcium response elements, referred to herein as SRE, CRE and NFAT RE.

The protein or peptide of interest can be any protein or peptide, and is preferably a protein or peptide having therapeutic or prophylactic activity. Such proteins are known in the art and include proteins that may block Alzheimer's plaque formation, proteins in current use or under investigation for use as therapeutic agents, antibodies. Suitable proteins and peptides include, but are not limited to insulin, proinsulin, alpha-gluconidase, glucocerebrosidase, alpha-galactosidase A, alpha-L-iduronidase, iduronate sulfatase, heparan sulfamidase, N-acetylglucosamidase, heparin-alpha-glucosamidine 6-sulfatase, galactose-6-sulfate sulfatase, beta-galatosidase, N-acetylgalactosamine-4-sulfatase, beta-glucoronidase and hyaluronidase. Other proteins of interest include peptide hormones, erythropoietin, thrombopoietin, G-CSF, Factor VIII, Factor IX, methyl-CpG-binding protein 2, MeCP2 and therapeutic antibodies, such as anti-VEGF, anti-EGF, anti-TNF and anti-HER2.

In another embodiment, the invention provides a method of modulating the activity of a cell, for example increasing or inhibiting one or more cellular activities. The method comprises the steps of exposing a recombinant cell of the invention to radiofrequency radiation or a magnetic field, thereby modulating the activity of the cell. In this embodiment, the ion channel is selected such that the ion gated by the channel modulates cell activity.

For example, the cell can be a neural cell, such as a neuron, and the ion channel can be a chloride channel. Activation of the ion channel results in an influx of chloride ions into the cell, thereby inactivating the cell. In another embodiment, the chloride channel is a mutant channel, such as a $TRPV1^{Mutant}$ channel as disclosed herein, including rat I679K-TRPV1, human I680K-TRPV1 or mouse I680K-TRPV1.

The invention further provides methods of modulating the activity of target cells in a subject. The method comprises the steps of (1) administering a pharmaceutical composition of the invention to the subject and (2) exposing the subject to radiofrequency radiation or a magnetic field, thereby modulating the activity of the target cells. In this embodiment, the ion channel is selected such that the ion gated by the channel modulates cell activity.

In a preferred embodiment of the method of modulating cell activity of target cells, the pharmaceutical composition comprises a vector of the invention, the target cells are endogenous cells and the method results in inhibition of the activity of the cells. In this embodiment, the ion channel is selected such that the ion gated by the channel decreases cell activity. For example, the target cells can be neural cells, such as neurons, and the ion channel can be a chloride channel. Activation of the ion channel results in an influx of chloride ions into the cell, thereby reducing the activity of the cell. In one embodiment, the chloride channel is a mutant channel, such as $TRPV1^{Mutant}$.

The methods of the invention allow noninvasive modulation of cell activity, and can be used in the treatment of diseases and disorders. For example, targeting of neurons at different sites with activating or inactivating genetic constructs of the invention can be used to regulate neural activity at one or more sites simultaneously and provide therapy in neurological disorders, including Parkinson's disease, anorexia nervosa, tremors, epilepsy, among others. In this embodiment, neurons at selected sites can be targeted by administering the vector of the invention at or adjacent to the anatomic site of the target cells. Using the method of the invention, neurons at two or more sites can be inactivated or activated. Alternatively, neurons at one or more selected sites can be inactivated, while neurons at one or more additional sites can be activated. Neural sites which can be activated and/or inactivated to produce therapeutic effects in a neurological disorder are known through studies utilizing invasive techniques as described above.

Other cell types can also be activated or inactivated using the methods of the invention. In preferred embodiments, activating or inactivating cells using the methods of the invention results in a therapeutic, palliative or prophylactic effect in the subject. For example, in an embodiment, the target cells are myocytes and the ion channel is a calcium channel. In this embodiment, the myocytes are activated by activation of the ion channel. In another embodiment, the target cells are immune cells and the ion channel is a calcium channel. In this embodiment, the resulting recombinant immune cells can be administered to a subject in need of treatment for cancer or another condition. Exposing the subject to radiofrequency radiation or a magnetic field results in activation of the transplanted immune cells.

In another embodiment, the target cells are lung epithelial cells and the ion channel is a chloride channel, such as $TRPV1^{Mutant}$. In this embodiment, the subject is in need of treatment for cystic fibrosis. Activation of the recombinant lung epithelial cells results in increased chloride ion flux in the recombinant cells, thereby ameliorating one or more symptoms of cystic fibrosis.

As discussed above, in certain embodiments, the therapeutic methods of the invention comprise ex vivo transfection of cells with a genetic construct of the invention and optionally, a recombinant gene encoding a protein, peptide or nucleic acid of interest. The cells can be of any type or a combination of different cell types. In one embodiment, the cells are autologous cells. In another embodiment, the cells are heterologous cells. The cells are preferably stem cells.

The cells can be genetically engineered using techniques well known in the art. Such techniques include, for example, in vitro recombinant DNA techniques, synthetic techniques, and in vivo genetic recombination. (See, for example, the techniques described in Sambrook J et al. 2000. Molecular Cloning: A Laboratory Manual (Third Edition), and Ausubel et al (1996) Current Protocols in Molecular Biology John Wiley and Sons Inc., USA). Any of the methods available in the art for gene delivery into a host cell can be used according to the present invention to deliver genes into the target cell population. Such methods include electroporation, lipofection, calcium phosphate mediated transfection, or viral infection. In a specific embodiment, a viral vector that contains a nucleic acid encoding the protein or nucleic acid of interest and a transcriptional regulatory sequence that can be induced upon excitation of the paramagnetic particles can be used. Such viral vectors include for example, retroviral, adenoviral or adeno-associated viral vectors. (See, Kozarsky and Wilson, 1993, Current Opinion in Genetics and Development 3:499-503 for a review of adenovirus-based gene delivery).

For general reviews of the methods of gene delivery see Strauss, M. and Barranger, J. A., 1997, Concepts in Gene Therapy, by Walter de Gruyter & Co., Berlin; Goldspiel et al., 1993, Clinical Pharmacy 12:488-505; Wu and Wu, 1991, Biotherapy 3:87-95; Tolstoshev, 1993, Ann. Rev. Pharmacol. Toxicol. 33:573-596; Mulligan, 1993, Science 260:926-932; and Morgan and Anderson, 1993, Ann. Rev. Biochem. 62:191-217; 1993, TIBTECH 11(5):155-215.

In another embodiment, the therapeutic methods of the invention comprise administering to the subject a vector of the invention. In this embodiment, the vector of the invention comprises the genetic construct of the invention and optionally, a recombinant gene encoding a protein, peptide or nucleic acid of interest, in a form which is suitable for transfection of cells ex vivo or in vivo. Suitable vectors include plasmids, including circular and linear plasmids, and viral vectors, such as adenovirus, preferably replication deficient adenovirus, and adeno-associated virus (AAV), liposomes and others as are known in the art. Preferably, the vector is a viral vector. More preferably the vector is adeno-associated virus. In one embodiment, the vector is administered locally at the site of the target cells. For example, a viral vector can be administered by injection at or adjacent to the anatomical site of the target cells.

In preferred embodiments of the invention for treating a neurological disorder, the vector of the invention, such as a viral vector, is administered to the subject at the site of the cells which are to be activated or inactivated. The treatment of certain neurological disorders by inactivation or activation of defined nodes in a neural circuit using invasive devices is known in the art. The knowledge derived from these studies can guide the selection of central or peripheral nervous system sites for neuronal activation of inactivation.

In order to access different organs non-invasively, it is necessary to have an electromagnetic field that is capable of passing through tissue as part of a system that allows some cells to be activated while the majority are not. Accordingly, radiofrequency (RF) electromagnetic fields are used for this purpose. RF signals at low and medium frequencies penetrate tissues freely and without significant energy absorption making it now possible to adapt this system for in vivo use (Jokela International Union of Radio Science 2008). In contrast to tissues, metallic/metal oxide nanoparticles placed in an alternating RF field absorb energy and heat in a controlled manner depending on the strength of the field, a process known as induction heating (Fortin et al., J. Am, Chem. Soc. 129:2628-2635). The heating capacity depends on nanoparticle composition, size, shape, and the frequency and power of the RF field and, as such, it is possible to regulate the heat generated within the physiological temperature range.

In vitro, the temperature response achieved is fast and decays quickly (inverse of the square of the distance) thus providing a rapid, functional "on-off" switch. The nanoparticles employed, for example, magnetic iron oxide and gold spheres, are easily prepared, have little or no intrinsic cell toxicity and can readily be adapted to target cells by incorporating streptavidin, antibodies, or pharmacological agents (Samanta, B. et al., J Mater Chem 18:1204-1208; Wang A Z et al. 2008 Expert Opin Biol Ther 8:1063-1070). Therefore, they are well suited for inducing localized temperature changes that can be transduced into cellular responses in vitro and in vivo.

The magnetic field applied to cells or the subject is a static or oscillating magnetic field. In one embodiment, the magnetic field is static. In certain embodiments, the magnetic field is not a component of electromagnetic radiation. Preferably, the cells or the subject is subjected to the magnetic field by being in proximity to the magnet. The magnetic field can be continuous over a period of time or applied at intervals. For example, an interval schedule can be used, such as a repeating 5 seconds on 2 minutes off, which allows for channel activation, but then removes the stimulus to prevent mechanical desensitization of the channel. Such intervals can range from 1 Hz. The optimal magnetic treatment schedule will depend on the specific channel used and the local cellular environment and can be determined by one of skill in the art. In one embodiment, the magnet is a high flux permanent magnet, for example a NIB magnet with surface flux of 5 kG.

In a preferred embodiment of the invention the recombinant cells are stem cells. Also within the scope of the invention are cells that have been genetically engineered to express a desired protein, or nucleic acid of interest. For example, in certain embodiments, the recombinant cells of the invention are engineered to express one or more proteins capable of providing a therapeutic benefit.

In one embodiment, the recombinant cells administered to the subject are autologous cells.

Preferably, the recombinant autologous cells are produced by a method comprising the steps of (1) removing cells from the subject; (2) transfecting the cells with a genetic construct of the invention and, optionally, a gene which encodes the protein, peptide or nucleic acid of interest operably linked to a regulatory sequence which is induced by activation of the ion channel.

Various delivery systems are known and can be used to deliver the recombinant cells to the subject. Such compositions can be formulated in any conventional manner using one or more physiologically acceptable carriers optionally comprising excipients and auxiliaries. Proper formulation is dependent upon the route of administration chosen.

The methods of the invention comprise administration of the recombinant cells and/or vectors of the invention to a subject in a pharmaceutically acceptable carrier, for treatment of various disorders or diseases. "Administering" means delivering in a manner which is effected or performed using any of the various methods and delivery systems known to those skilled in the art. Administering can be performed, for example, pericardially, intracardially, subepicardially, transendocardially, via implant, via catheter, intracoronarily, intravenously, intramuscularly, subcutaneously, parenterally, topically, orally, transmucosally, transdermally, intradermally, intraperitoneally, intrathecally, intralymphatically, intralesionally, epidurally, or by in vivo electroporation. Administering can also be performed, for example, once, a plurality of times, and/or over one or more extended periods.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. The composition can be formulated as a suppository, with traditional binders and carriers such as triglycerides. Oral formulation can include standard carvers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic compound, preferably in purified form, together with a suitable amount of carrier so as to provide the form for proper administration to the patient. The formulation should suit the mode of administration.

The appropriate concentration of the compositions of the invention which will be effective in the treatment of a particular disorder or disease will depend on the nature of the disorder or disease, and can be determined by one of skill in the art using standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose response curves derived from in vitro or animal model test systems. Additionally, the administration of the compound could be combined with other known efficacious drugs if the in vitro and in vivo studies indicate a synergistic or additive therapeutic effect when administered in combination.

Additionally, the progress of the patient receiving the treatment may be determined using assays that are designed to detect the physiologically active protein expressed by the recombinant cells.

The present invention further relates to transgenic non-human animals that may be engineered to produce cells that respond to excitation of paramagnetic nanoparticle by radiofrequency radiation or a magnetic field in a desired fashion. For example, the transgenic animals may be engineered to express the ferritin and ion channel fusion proteins of the invention. Said target cells may either naturally, or through genetic engineering, express a protein or nucleic acid molecule of interest upon paramagnetic nanoparticle excitation. Such transgenic animals provide in vivo model systems for studying normal physiological processes as well as disease processes. The transgenic animals of the invention may further be useful as in vivo model systems for use in identification and testing of novel therapeutic compounds of interest.

The present invention provides methods and compositions for studying the role of different cell types in a complex organism. The definitive test of cell function is to selectively turn on or off the activity of a single cell type in a living animal and examine the effect on physiological function. The present invention provides for the use of nanoparticles to activate defined cell populations remotely with radiowaves or a magnetic field. In certain embodiments, these cells are engineered to also express TRPV1, a single component, temperature-sensitive ion channel that can undergo conformational change in response to a temperature increase or molecular motion to allow graded calcium entry. Exposing these cells to a radiofrequency radiation or a magnetic field activates TRPV1 channels, resulting in a $Ca^{2+}$ current and cell activation. Data is provided below that confirms the efficacy of this method in vitro and in vivo. The technology can be used to modulate functions such as hormone release and neural activity.

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Various publications are cited herein, the contents of which are hereby incorporated, by reference, in their entireties.

EXEMPLIFICATION

Example 1 Remote Regulation of Glucose Homeostasis in Mice Using Genetically Encoded Nanoparticles Methods
Radiofrequency Field A 465 kHz sinusoidal signal was provided by a signal generator and applied through an amplifier (both Ultraflex, Ronkonkoma, NY) to a 2-turn solenoid coil with a radius of 2.5 cm to produce a magnetic field strength of 5 mT or more. Samples were placed within the solenoid.

Application of Static Magnetic Force

A solenoid magnetic microneedle was fabricated by winding a 24G copper wire around a ¼" Permalloy-80 rod 1200 times and the tip lathed to hemisphere with a diameter of 100 um. Current through the coil was controlled by a Beckman 3A/30V adjustable power supply. The needle tip was placed ~30 um from the cells being pulled, and the magnetic force was produced by a 1.8 A current.

Force Calibration

It has been estimated that the force to mechanically open an ion channel is approximately 0.2-0.4 $pN^{31}$. Therefore, we measured the force from magnetic treatment on the cells using a method described by Kim et al. Briefly, iron loaded, ferritin expressing cells were fixed in paraformaldehyde then added to aqueous buffer and subjected to a static magnetic field. The cells accelerate towards the magnet and their velocity is proportional to the magnitude of the magnetic force. This is modeled as a creeping flow around a sphere, where the drag of the fluid on the particle is equal to the magnetic force on the $cell^{32}$. With U being the cell velocity, being the kinematic viscosity of the buffer, and $D_{cell}$ being the cell diameter, this linear relationship is:

$$F_{drag}=F_{magnetic}=3\pi U\mu D_{cell}$$

HEK cells were loaded with transferrin for 3 days then transfected and collected 24 hours later. After fixation, the cells were added to buffer and subjected to magnetic field. The movement of the cells was recorded for 5 seconds in duplicate. From these two image stacks, the position of 3 cells were tracked over 10 frames for a total of ~60 cell velocities recorded. For all cells expressing ferritin, the magnetic force was over 10 pN. Cells loaded with iron but not expressing ferritin showed magnetic forces less than 1 pN possibly due to random Brownian motion of the fixed cells in the liquid. As 10 pN is greater than the force required to open an ion channel, this experiment shows that the magnetic treatment is applying sufficient force to observe channel openings.

Plasmids

TRPV1 (in pcDNA3.1) was a kind gift of Wolfgang Liedkte (Duke University, NC) and cloned into pEGFPN1 (Clontech, Mountainview, CA). A GFP binding nanobody sequence was synthesized by Integrated DNA Technologies (Coralville, IA) and fused to the N-terminal of TRPV1 to create αGFP-TRPV1. pCR2.1 with EF1alpha-ferritin chimera was modified by cloning a myristoylation signal to the N-terminal of ferritin light chain to create MyrFerritin or addition of GFP sequence from Pegfp-n1 to the N-terminal of ferritin light chain to create GFP-ferritin. TRPV1 followed by a 2 A sequence and ferritin or MyrFerritin or αGFP-TRPV1 followed by a 2 A sequence and GFP-Ferritin were cloned into MSCV-hygro plasmid and calcium responsive furin insulin was cloned into MSCV-puro plasmid (Clontech,) for retrovirus production using Phoenix packaging cells. These sequences were also cloned into pVQ Ad CMV KNpA for generation of replication deficient adenovirus. The fidelity of PCR products and cloning was confirmed by DNA sequencing.

Cell Culture and In Vitro Studies

Human embryonic kidney cells (HEK 293 T) were cultured in Dulbecco's modified eagle medium with 10% fetal bovine serum (Gibco, Carlsbad, CA) at 37° C. and 5% $CO_2$. Phoenix ecotropic packaging cells (Stanford University) were grown in Dulbecco's modified eagle medium with 10% fetal bovine serum (Gibco) at 37° C. and 5% $CO_2$. Murine mesenchymal stem cells (Gibco) were grown in DMEM/F12 medium with 10% fetal bovine serum at 37° C. and 5% $CO_2$. Stable cell lines were produced by retroviral infection of MSC using the Phoenix system. Briefly, Phoenix eco cells ($2\times10^6$ cells per 6-cm dish) were transfected with MSCV-puro or hygro plasmids as described above. After 24 hours, the medium was replaced and the cells placed at 32° C. Medium was aspirated after a further 24 h and spun to remove cell debris. The Phoenix cell supernatant was added to MSC (plated at $1\times10^6$ cells per 6-cm dish) using a 1:2 dilution in RPMI medium/10% FBS with polybrene (4 µg/ml, Sigma-Aldrich, St Louis, MO). Cells were incubated at 32° C. for a further 24 h before replacing the medium with DMEM/F12 medium/10% FBS. Selection medium was added 48 h after infection. Stably transfected MSC were seeded onto 5×5×5 mm gelatin sponge scaffolds (Gelfoam) that had been preincubated in PBS by addition of $2\times10^6$ cells resuspended in 60 µl of medium directly to the scaffold.

Cells were maintained at 37° C. for 4 hours before addition of 450 µl DMEM/F12 medium/10% FBS. Cell scaffold constructs were then maintained at 37° C. for 5 days before implantation. For immunocytochemistry and RF studies, cells were cultured on 12-mm cover glass (Fisher Scientific, Pittsburgh, PA) coated with collagen (BD biosciences, Bedford, MA) and poly-D-lysine (Millipore, Billerica, MA). Cells were transfected 24 h after plating using lipofectamine 2000 (Invitrogen, Carlsbad, CA).

Culture medium was replaced 18 h after transfection and holotransferrin (2 mg/ml, Sigma) was added to the cells. Cells were studied 72 h-96 hrs after transfection or subculture.

RF dependent release of calcium dependent human insulin: 24 h prior to the study, cells were placed in 1% FBS medium at 32° C. to ensure minimal activation of TRPV1 and calcium dependent pathways. On the day of study, cells were preincubated for 30 min in 500 µl PBS. Cells were incubated in 300 µof calcium imaging buffer at room temperature (control) or in a RF field at room temperature. The supernatant was removed after 60 min, spun to remove cell debris and frozen at −80° C. until assay. For gene expression analysis, cells from the supernatant and cover glass were lysed and the lysate stored at 80° C. until RNA purification.

Magnet dependent release of calcium dependent human insulin: Cells were prepared as described above. Cells were incubated in 300 µl of calcium imaging buffer at room temperature (control) or treated with a static magnetic field for 5 seconds every 2 minutes for 1 hour at room temperature. To produce a constant magnetic field, a neodymium-iron-boron permanent magnet was used (K&J magnetics Pipersville, PA). This was able to produce a strong magnetic flux density of around 5 kiloGauss near the cell surface. The supernatant was removed after 60 min, spun to remove cell debris and frozen at −80° C. until assay. For gene expression analysis, cells from the supernatant and cover glass were lysed and the lysate stored at 80° C. until RNA purification.

Calcium Imaging

Transfected cells were washed three times in PBS then loaded with Fluo-4 3 µM (Invitrogen) in the presence of sulfinpyrazone 500 µM (Sigma) for 60 min at room temperature. Cells were washed again in PBS then incubated for 30 min in sulfinpyrazone in PBS. Cells were washed and then imaged in calcium imaging buffer. Imaging was performed using a Deltavision personal DV imaging system (Applied Precision, Issawaq, WA) equipped with a custom-made ceramic lens. Cells were imaged before and during RF treatment, before or during magnet treatment or before and after treatment with 200 µM 2-aminoethoxydiphenyl borate (2-APB).

Immunocytochemistry and Immunohistochemistry

Immunocytochemistry (ICC) and immunohistochemistry (IHC) were used to detect expression of TRPV1, GFP and HA tagged ferritin and to quantify apoptotic cells in cells and tissue. Cells were washed twice in PBS and then fixed for 15 min in 2% paraformaldehyde (Electron Microscopy Services, Hatfield, PA.). Tissue was fixed in 10% formalin (Sigma) at 4° C. overnight then placed in 30% sucrose in PBS at 4° C. for a further 24 h. Tissue was embedded in OCT and frozen before 20 µm cryosections were cut and placed directly on glass slides. Slides were placed at 55 degrees for 1 h then stored at −80° C. before staining. Cells or tissue sections were washed and fixed as above then incubated for 1 h in blocking buffer (3% BSA (Sigma) and 2% goat serum (Sigma) in PBS with 0.1% Triton-X (Sigma)). Cells were then incubated in primary antibody (rabbit anti-TRPV1 1:500, mouse anti-Ha 1:1000 (Cell signaling), chicken anti-GFP 1:1000 (Abcam), rabbit anti-activated caspase 3 1:250 (Promega)) diluted in blocking buffer overnight at 4 degrees. Cells or tissue were washed three times in PBS before incubation in secondary antibody (goat anti-rabbit 594 or goat anti-rabbit 488, goat anti-chicken 488, goat anti mouse 360, all 1:1000) diluted in blocking buffer for 2 h. The cells or tissue were washed a further three times in PBS before mounting using Fluoromount (Southern Biotech, Birmingham, AL).

Images were acquired using a Zeiss Axioplane microscope and captured digitally with separate bandpass filters using the multichannel module of the AxioVision Zeiss software. Additional images were acquired using confocal microscopy (LSM 510 laser scanning confocal microscope; Carl Zeiss MicroImaging, Inc.). Quantification of active caspase-3 immunostaining was performed by an investigator blinded to the treatment group.

Animals and In Vivo Studies

Male athymic NCr-nu/nu mice (NCI-Frederick, 6-8 weeks old), an outbred strain, or male C57B16 mice were used and housed under controlled light conditions (12 h light/12 h dark) and temperature (22° C.), single-caged, and fed ad libitum on standard mouse chow. Animal care and experimental procedures were performed with the approval of the Animal Care and Use Committee of Rockefeller University (protocol 11421) under established guidelines.

Study 1: Nude mice were treated for 5 days with low dose streptozotocin. Two days later, MSC seeded onto gelatin scaffolds prepared as described above were implanted into the flank of anesthetized nude mice bilaterally. Radiofrequency studies were performed 4 weeks later. Mice received two doses of intraperitoneal iron dextran (50 µl of 100 mg/ml) 5 and 3 days before the study. Mice were fasted overnight before all studies. On the study day, mice with MSC implants (calcium dependent insulin alone (control), TRPV1/myrferritin with calcium dependent insulin or αGFP-TRPV1/GFP-ferritin with calcium dependent insulin, n=6-8/group) were anesthetized with inhaled isoflurane. After 30 min, mice were treated with an RF magnetic field for 60 min by placing in a solenoid connected to the RF generator. Tail vein samples were taken at −30 and 0 min before RF magnetic field treatment and at 15, 30, 45, 60, 75, 90 and 120 min after the onset of RF treatment. Retro-orbital blood was taken using EDTA coated capillary tubes at −30 and 60 min for plasma insulin measurement. After 120 min, half the mice in each group were sacrificed and the implants removed. Each tumor was divided in two and one half snap frozen in liquid nitrogen for RNA extraction and the one half placed in 10% formalin for immunohistochemistry. Tissue was harvested from the remaining mice 24 hours later after identical anesthesia but no RF treatment.

Study 2: C57B16 mice were treated for 5 days with low dose streptozotocin. Two days later, replication deficient adenoviruses expressing Lac Z, TRPV1/myrferritin with calcium dependent insulin or αGFP-TRPV1/GFP-ferritin with calcium dependent insulin (n=6-8/group) were injected into the jugular vein of anesthetized C57B16 mice. Iron supplementation was given as above. After 4 weeks, mice were studied using an identical protocol to study 1.

Study 3: C57B16 mice were prepared as above but without the TRPV1/myrferritin group. Mice received two doses of intraperitoneal iron dextran (50 µl of 100 mg/ml) 5 and 3 days before the first study and then 3 days before each subsequent study. The first RF study was performed 2 weeks after virus injection and weekly thereafter until 6 weeks. The study protocol was as described for study 1 on each occasion.

Study 4: C57BL6 mice were prepared as for study 2 but without the TRPV1/myrferritin group. Iron supplementation was given as above and after 4 weeks, mice were studied using magnet stimulation using an identical protocol to study 1 but with a static magnetic field for 5 seconds every 2 minutes for 1 hour as above.

Assays

Proinsulin was measured in cell supernatants by ELISA (Alpco, Salem, NH) according to manufacturer's protocol. Blood glucose was determined using a Breeze 2 glucometer (Bayer; Leverkusen, Germany). Blood was spun for 10 min and plasma was collected. Plasma levels of human insulin were determined in mouse plasma by human specific ELISA (Alpco).

Real-Time PCR

Total RNA was isolated by homogenizing tissue in TRIzol reagent (Invitrogen) or cells in buffer RLT and purifying the RNA using QIAGEN RNA prep kit. Complimentary DNA was synthesized using QIAGEN omniscript RT kit. Real-time PCR was performed using the TaqMan system (Applied Biosystems; Foster City, CA) according to the manufacturer's protocol.

Statistics

All data were analyzed for statistical significance using the Student's t test. P values are as indicated.

In vitro optimization of gene expression and protein release with genetically encoded nanoparticles.

Figure 1A:
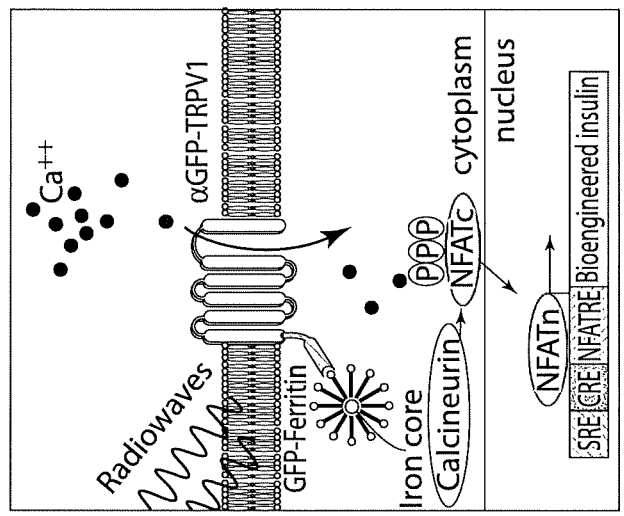
FIG. 1A is a schema of systems testing three alternate locations of genetically encoded ferritin to generate iron oxide nanoparticles to open the temperature sensitive channel TRPV1 in response to RF: cytoplasmic ferritin (left panel, TRPV1/ferritin), membrane tethered ferritin achieved by addition of an N-terminal myristoylation signal (middle panel, TRPV1/myrferritin) and channel associated achieved by adding a GFP binding domain to the N-terminal of TRPV1 and GFP to the N-terminal of ferritin (right panel, αGFP-TRPV1/GFP-ferritin).
Figure 1A:
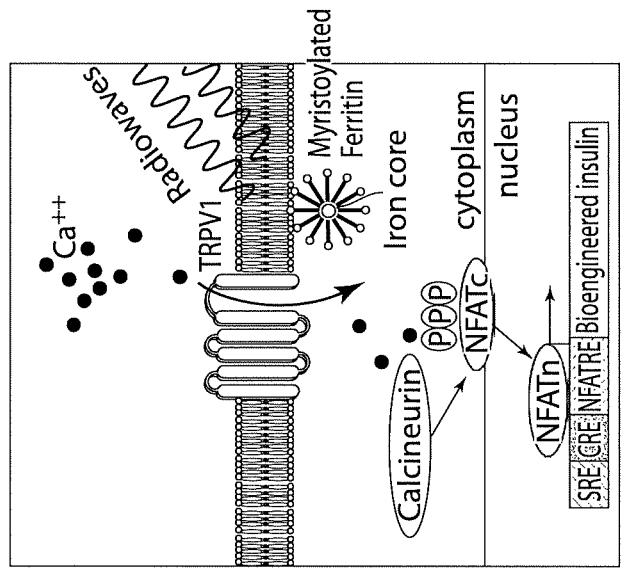
Figure 1A:
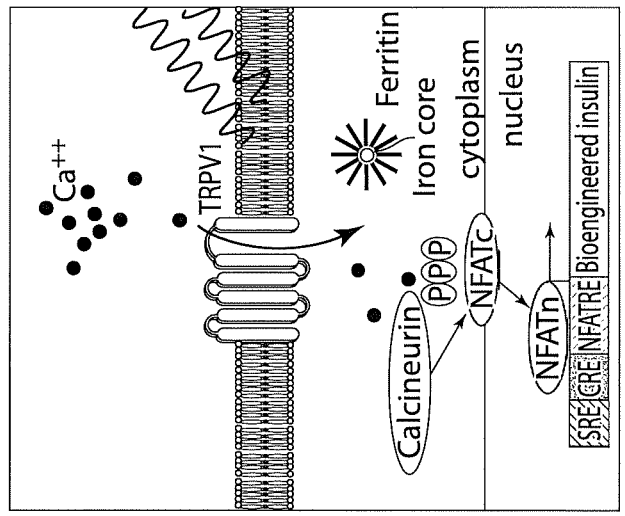
Figure 1B:
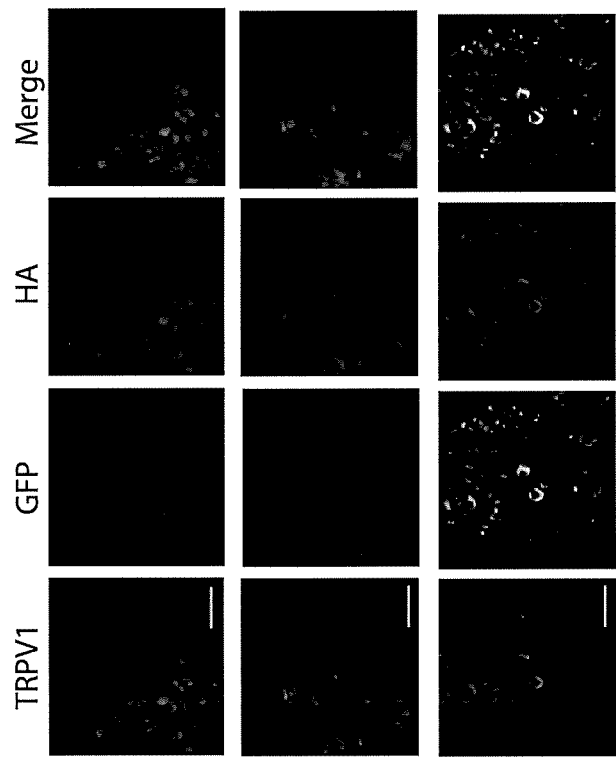
FIG. 1B shows immunohistochemistry for TRPV1, GFP and HA tagged ferritin chimera in HEK 293T cells transfected with TRPV1/ferritin confirmed membrane expression of TPRV1 and cytoplasmic expression of ferritin (upper panels), in cells transfected with TRPV1/myrferritin IC confirmed membrane expression of both TRPV1 and ferritin (middle panels) and in cells transfected with αGFP-TRPV1/GFP-ferritin, IHC confirmed membrane expression of TRPV1, GFP and ferritin (lower panels).
Figure 1B:
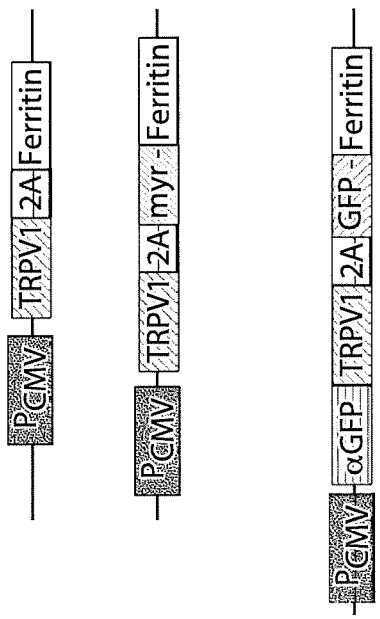
Figure 1C:
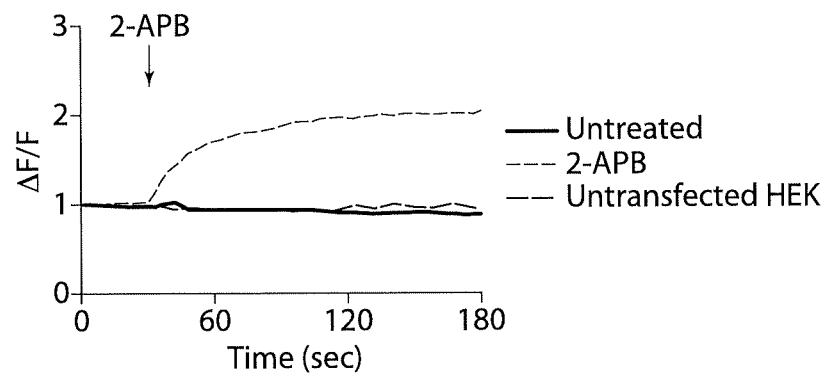
FIG. 1C illustrates representative changes in Fluo-4 fluorescence after application of TRP agonist 2APB to HEK cells transfected with αGFP-TRPV1/GFP-ferritin.
Figure 1D:
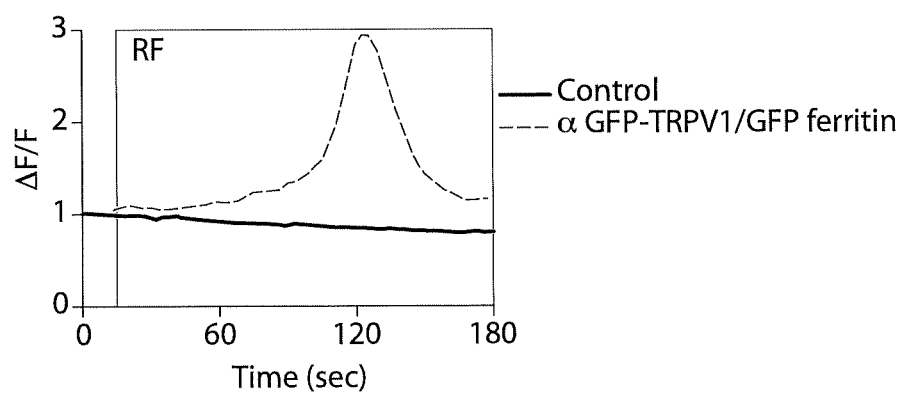
FIG. 1D illustrates representative changes in Fluo-4 fluorescence after application of RF to HEK cells transfected with αGFP-TRPV1/GFP-ferritin.

We first set out to optimize a genetically-encoded gene expression system using RF to regulate gene expression by testing three separate constructs that differ with respect to the proximity of the ferritin nanoparticles to the TRPV1 channel. In the first construct, a wildtype temperature-sensitive transient receptor potential vanilloid 1 (TRPV1) cation channel was co-expressed with a ferritin chimeric protein comprised of ferritin light chain, flexible linker region and ferritin heavy chain[12] expressed in the cytoplasm (TRPV1/ferritin) (FIG. 1A left panel). In the second construct, a wildtype TRPV1 channel was co-expressed with a chimeric ferritin fusion protein with a myristoylation signal directing ferritin to the cell membrane (TRPV1/myrferritin) (FIG. 1A, middle panel). In the third, a modified TRPV1 channel with an N-terminal fusion to a single domain anti-GFP camelid antibody[13] was co-expressed with a chimeric ferritin protein with an N-terminal fusion to GFP. This results in the tethering of GFP-tagged ferritin chimera to the modified TRPV1 so the components are juxtaposed at the cell membrane (αGFP-TRPV1/GFP-ferritin) (FIG. 1A, right panel). Immunohistochemistry for TRPV1, GFP and HA tag (in the flexible linker region of the ferritin chimera) in transfected HEK cells confirmed the predicted location of the expressed components (FIG. 1). N-terminal modification of TRPV1 did not disrupt its ability to respond to the TRP agonist 2APB, as HEK cells transfected with αGFP-TRPV1 showed a significant increase in intracellular calcium with 2APB (2.0-fold vs 0.85-fold change in Fluo-4 fluorescence (FIG. 1C). In addition, treating HEK cells expressing αGFP-TRPV1/GFP-ferritin with RF (465 kHz) resulted in significantly increased intracellular calcium compared to nontransfected controls (2.9-fold vs. 0.8-foldchange in Fluo-4 fluorescence, FIG. 1D).

Figure 1E:
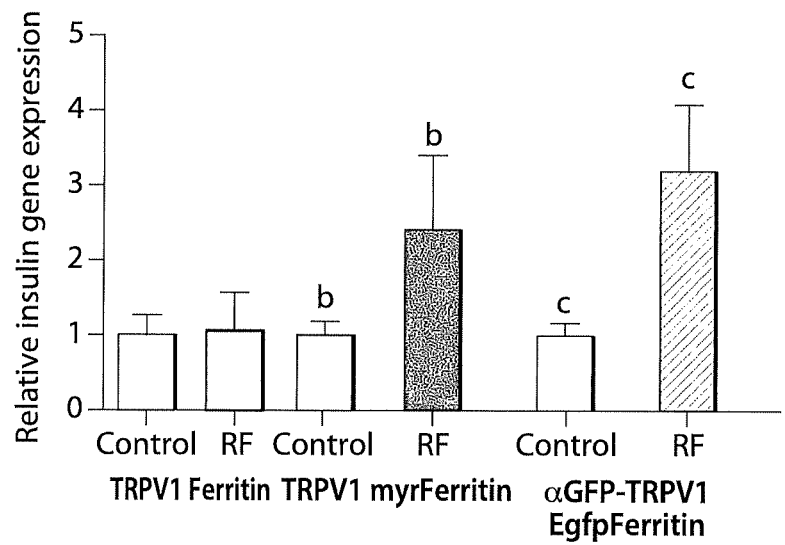
FIG. 1E is a graph showing that RF treatment increases insulin gene expression in HEK cells expressing TRPV1/ferritin, TRPV1/myrFerritin and αGFP-TRPV1/GFP-Ferritin.
Figure 1F:
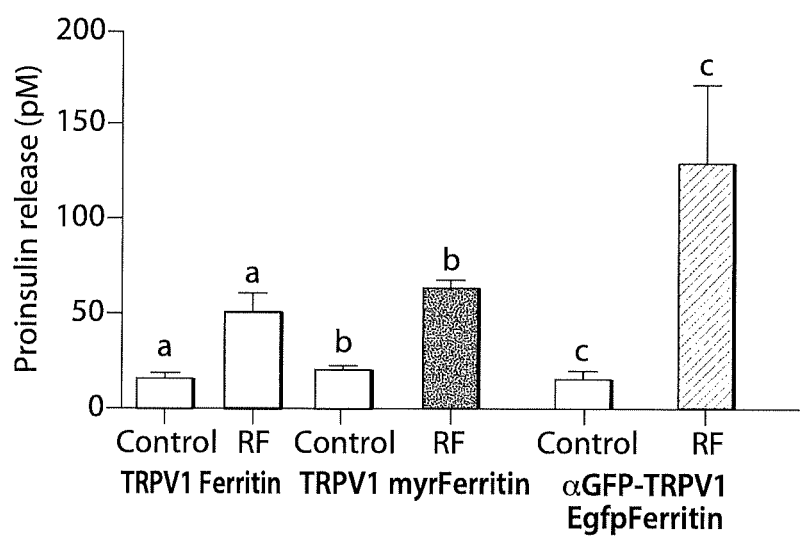
FIG. 1F is a graph showing that RF treatment increases proinsulin release from HEK cells expressing TRPV1/ferritin, TRPV1/myrferritin and αGFP-TRPV1/GFP-ferritin. In all cases, columns marked with the same letter indicate significance, p<0.05. Error bars indicate SEM.

Next, we tested the efficiency of the three constructs in transducing a RF signal into gene expression in vitro using a calcium-responsive reporter gene. As previously reported[9], the promoter is comprised of a 5' regulatory region of three serum response elements (SRE), three cyclic adenosine monophosphate response elements (CRE) and three nuclear factor of activated T cell response elements placed upstream of a minimal promoter, and driving $Ca^{2+}$ dependent expression of a furin modified insulin. Insulin gene expression for each of the three constructs was assayed after RF treatment of transfected HEK cells for one hour. TRPV1/ferritin, TRPV1/myrferritin and αGFP-TRPV1/GFP-ferritin all significantly increased calcium-dependent insulin gene expression with RF treatment (TRPV1/ferritin: RF treated 1.58±0.19 relative insulin gene expression vs. untreated 1.0±0.19; TRPV1/myrferritin: RF treated 2.37±0.83 relative insulin gene expression vs. untreated 1.0±0.2; and αGFP-TRPV1/GFP-ferritin: RF treated 2.40±0.96 relative insulin gene expression vs. untreated 1.0±0.47, all p<0.05) (FIG. 1E). The TRPV1/myrferritin and αGFP-TRPV1/GFP-ferritin showed greater induction of gene expression than TRPV1/ferritin construct that directs the expression of ferritin in the cytoplasm. Similarly, RF treatment significantly increased proinsulin release from transfected HEK cells compared to untreated (TRPV1/ferritin: RF treated 457±102% basal vs. untreated 100±14.9% basal; TRPV1/myrferritin: RF treated 423±55.9% basal vs. untreated 100±13.7% basal; and αGFP-TRPV1/GFP-ferritin: RF treated 743±254% basal vs. untreated 100±6.2% basal, all p<0.05) (FIG. 1F). In this case, the tethering of ferritin to TRPV1 using αGFP-TRPV1/GFP-ferritin construct induced greater proinsulin release compared to the other two constructs. These data suggest that direct tethering of ferritin to TRPV1 is able to transduce the RF signal more efficiently than expression of ferritin in the cytoplasm or plasma membrane.

Figure 2A:
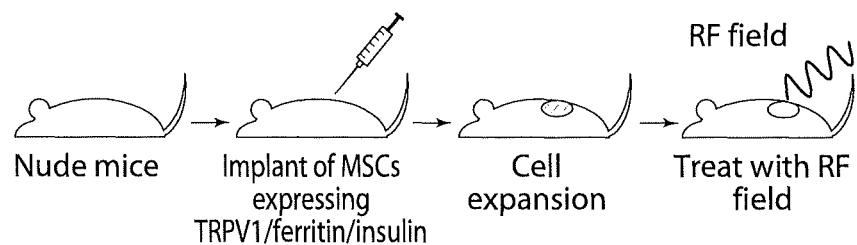
FIG. 2A is a schema for delivery and assessment of effects of RF treatment on blood glucose in mice with implanted mesenchymal stem cells expressing TRPV1/myrferritin or αGFP-TRPV1/GFP-ferritin and calcium dependent human insulin.
Figure 2B:
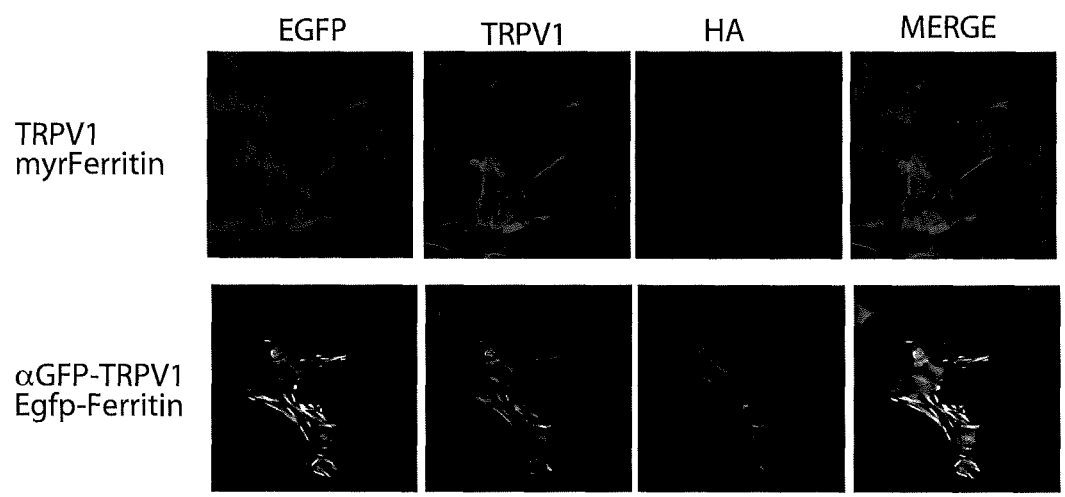
FIG. 2B illustrates immunohistochemistry for TRPV1, EGFP and HA tagged ferritin in sections of gelatin scaffold implants seeded with mesenchymal stem cells stably expressing TRPV1 and myristoylated ferritin (upper panels) or αGFP-TRPV1 and GFP-ferritin fusion (lower panels).
Figure 2C:
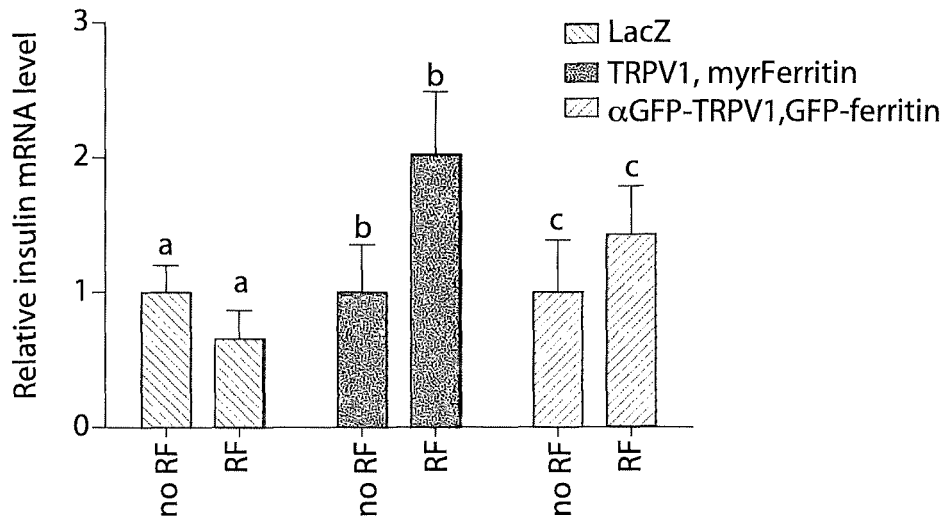
FIG. 2C is a graph illustrating the effects of RF treatment on insulin gene expression in control, TRPV1/myrferritin and αGFP-TRPV1/GFP-Ferritin expressing MSC implants. RF treatment significantly increases insulin gene expression in MSC expressing TRPV1 and genetically encoded nanoparticles. Same letter indicates p<0.05. Error bars indicate SEM.
Figure 2D:
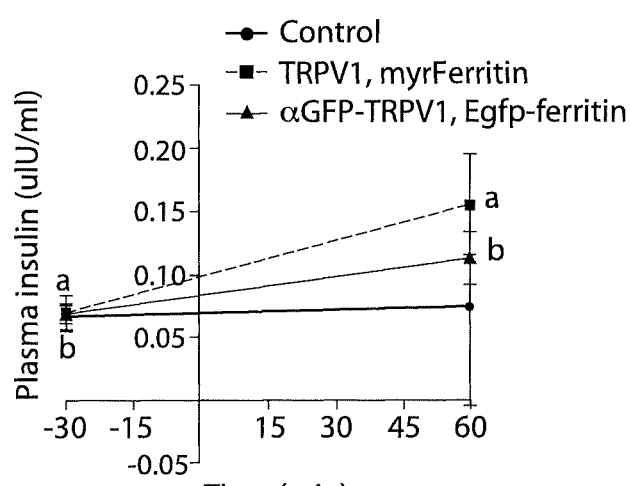
FIG. 2D is a graph showing that plasma insulin was significantly increased by RF treatment in mice implanted with MSC expressing TRPV1/myrferritin or αGFP-TRPV1/GFP-ferritin but not in control mice. Same letter indicates p<0.05. Error bars indicate SEM.
Figure 2E:
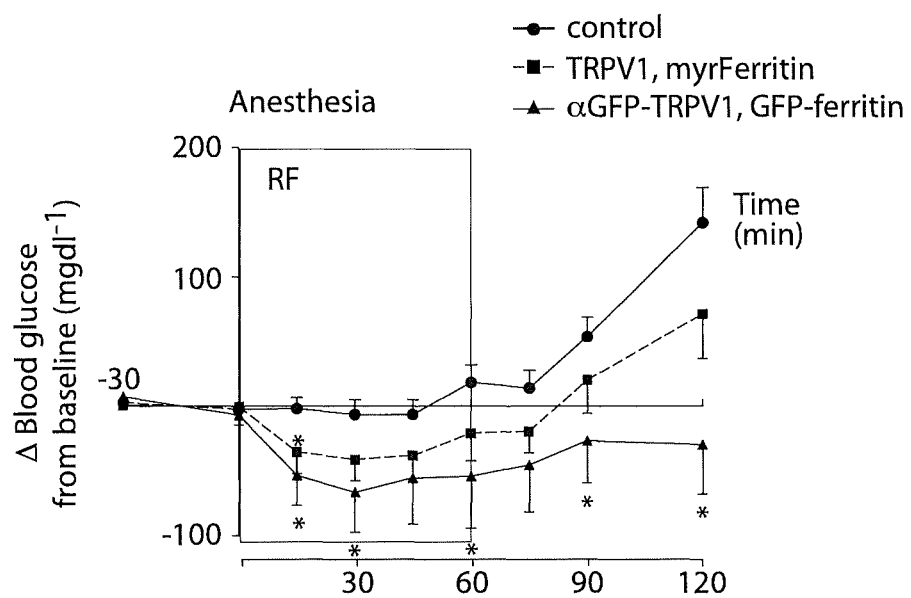
FIG. 2E is a graph showing that RF treatment of mice implanted with MSC expressing αGFP-TRPV1/GFP-ferritin significantly reduces blood glucose compared to control mice. Asterisks indicated p<0.05, error bars indicate SEM.
Figure 2F:
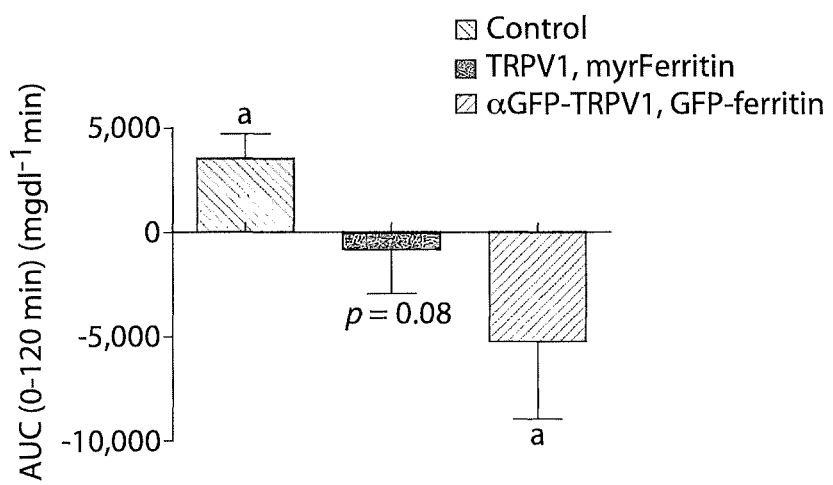
FIG. 2F is a graph showing that RF treatment significantly reduces blood glucose over the course of the study in mice implanted with MSC expressing αGFP-TRPV1/GFP-ferritin compared to RF treatment of mice with control MSC implants. Same letter indicates p<0.05. Error bars indicate SEM.

RF regulated gene expression in vivo using genetically encoded nanoparticles based on these in vitro data, we decided to test the efficiency of the TRPV1/myrferritin and αGFP-TRPV1/GFP-ferritin constructs in vivo by implanting engineered stem cells or by viral delivery of the constructs using a recombinant adenovirus. Murine mesenchymal stem cells (MSCs) were stably transfected with TRPV1/myrferritin or αGFP-TRPV1/GFP-ferritin and the calcium-dependent insulin transgene. RF treatment of stably transfected MSC cells expressing either construct significantly increased insulin gene expression and proinsulin release in vitro (FIGS. 1A and B). Stably transfected MSCs were grown on gelatin scaffolds 14 and then implanted into streptozocin (STZ)-treated nude mice (FIG. 2A). The TRPV1/myrferritin and αGFP-TRPV1/GFP-ferritin expressing MSCs were readily visualized on the gelatin scaffold (FIG. 2B). RF treatment of fasted mice implanted with TRPV1/myrferritin or αGFP-TRPV1/GFP-ferritin-expressing MSCs significantly increased insulin gene expression in the implanted cells expressing TRPV1/ferritin constructs but not in control cells (FIG. 2C) (TRPV1/myrferritin: 1.8±0.3 relative insulin gene expression vs. 1.0±0.1 basal, $p<0.05$ or αGFP-TRPV1/GFP-ferritin: 1.4±0.1 relative insulin gene expression vs. 1.0±0.1 basal, $p<0.05$). Plasma insulin was significantly increased in mice implanted with either of the TRPV1/ferritin constructs after RF treatment (FIG. 2D) (TRPV1/myrferritin: 200±33% basal post-RF vs. 100±21% basal pre-RF, $p<0.05$, or αGFP-TRPV1/GFPferritin: 153±19% basal post-RF vs. 100±10% basal pre-RF, $p<0.05$). Blood glucose levels (FIG. 2E) fell significantly with RF treatment in these mice and the cumulative change in blood glucose was also decreased (area under the curve, AUC(0-120 min)) for mice implanted with TRPV1/myrferritin ($p=0.08$) and significantly decreased for mice implanted with stem cells expressing the αGFP-TRPV1/GFP-ferritin constructs ($p<0.05$)(FIG. 2F). These data show that RF treatment of stem cells engineered to express modified TRPV1 and endogenous iron oxide nanoparticles constructs can regulate gene expression and protein release in vivo suggesting that this system could be used in conjunction with engineered stem cells for regulated protein release in vivo. The data also suggest that tethering the ferritin particles directly to the temperature sensitive channel may improve the sensitivity of the system.

Figure 3A:
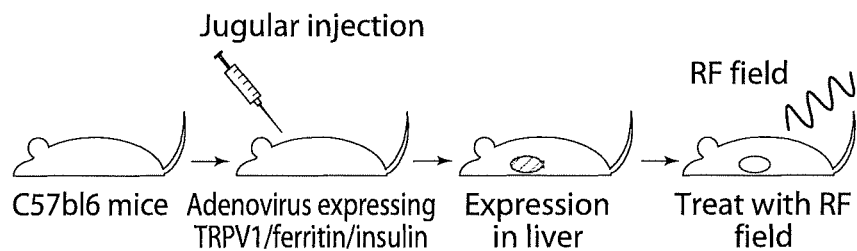
FIG. 3A is a schema for delivery and assessment of effects of RF treatment on blood glucose in C57Bl6 mice injected with replication deficient adenovirus expressing Lac Z, TRPV1/myrferritin or αGFP-TRPV1/GFP-ferritin and calcium dependent human insulin.
Figure 3B:
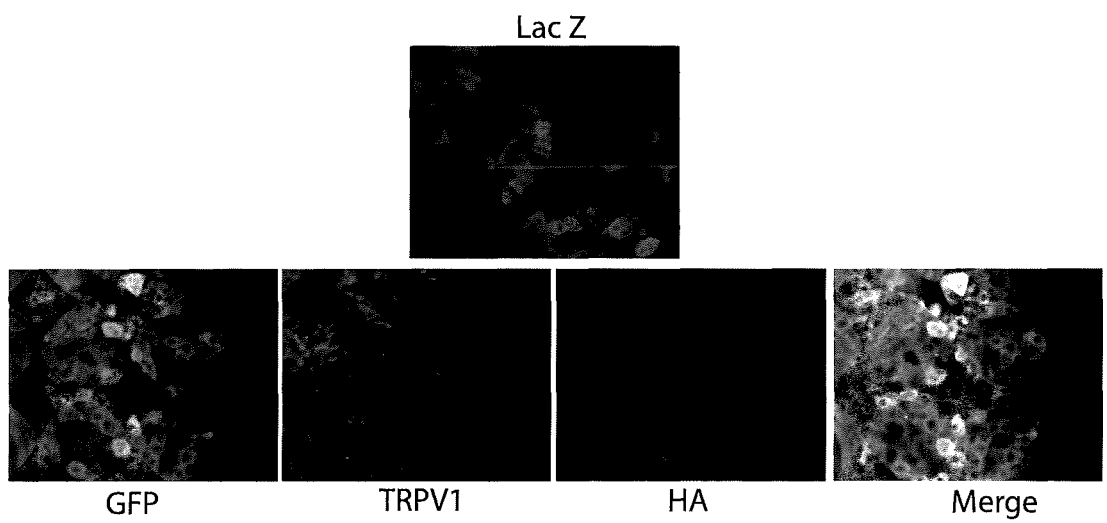
FIG. 3B illustrates immunohistochemistry for TRPV1, EGFP and HA tagged ferritin in hepatic tissue expressing TRPV1 and myristoylated ferritin (upper panels) or αGFP-TRPV1 and GFP-ferritin fusion (lower panels).
Figure 3C:
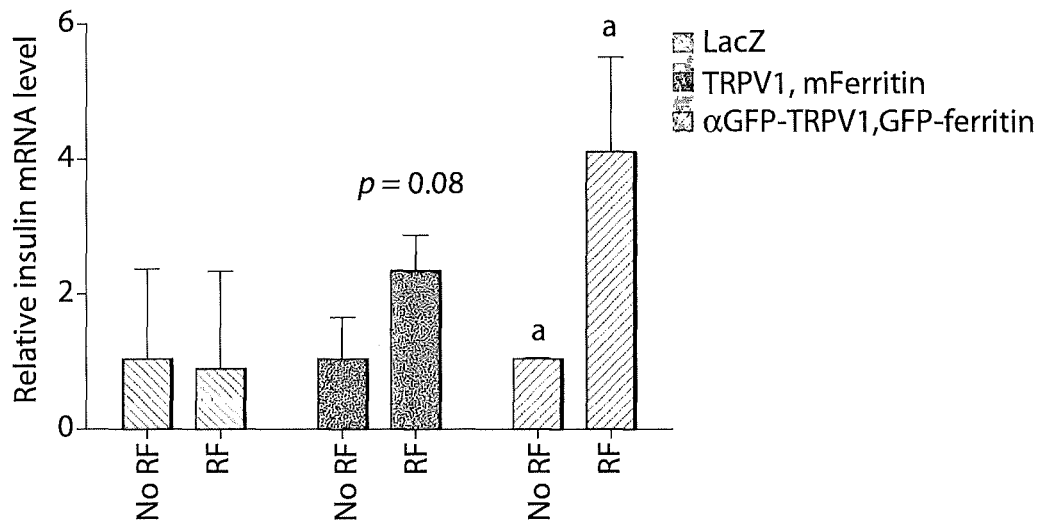
FIG. 3C is a graph showing the effects of RF treatment on hepatic insulin gene expression in mice treated with adenovirus expressing Lac Z, TRPV1/myrferritin or αGFP-TRPV1/GFP-ferritin and calcium dependent human insulin. RF treatment significantly increases insulin gene expression in hepatic tissue expressing αGFP-TRPV1/GFP-ferritin. Same letter indicates p<0.05. Error bars indicate SEM.
Figure 3D:
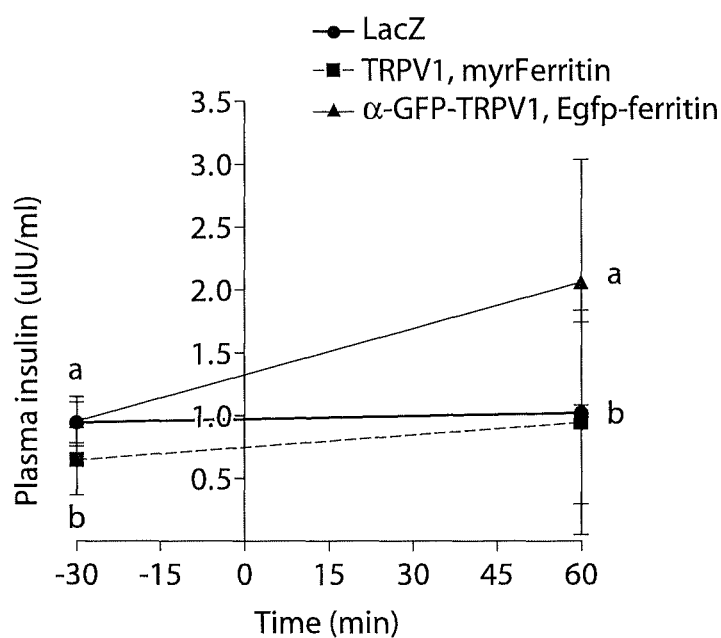
FIG. 3D is a graphing showing that plasma insulin was significantly increased by RF treatment in mice expressing TRPV1/myrferritin or αGFP-TRPV1/GFP-ferritin but not in control mice. Same letter indicates p<0.05. Error bars indicate SEM.
Figure 3E:
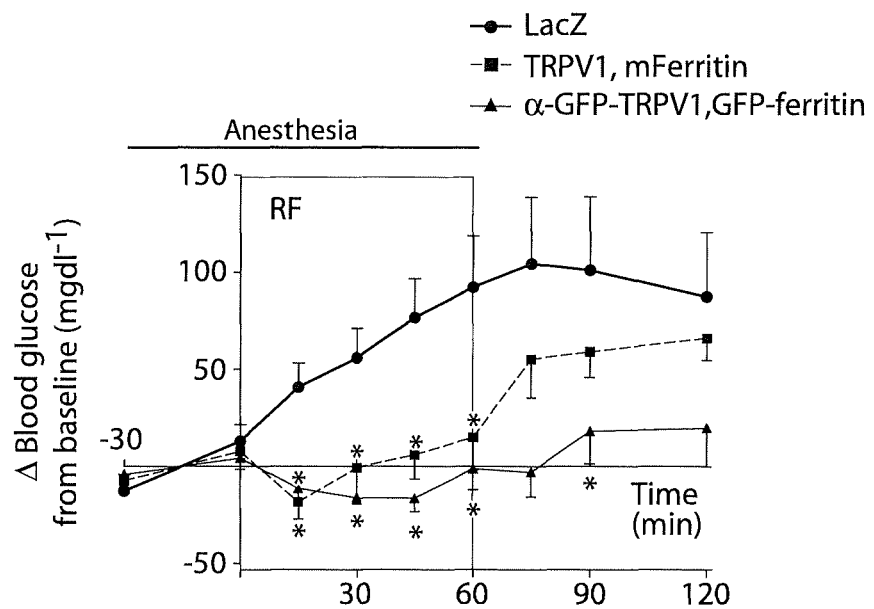
FIG. 3E is a graph showing that RF treatment of mice injected with adenovirus expressing αGFP-TRPV1/GFP-ferritin significantly reduces blood glucose compared to control mice. Asterisks indicated p<0.05, error bars indicated SEM.
Figure 3F:
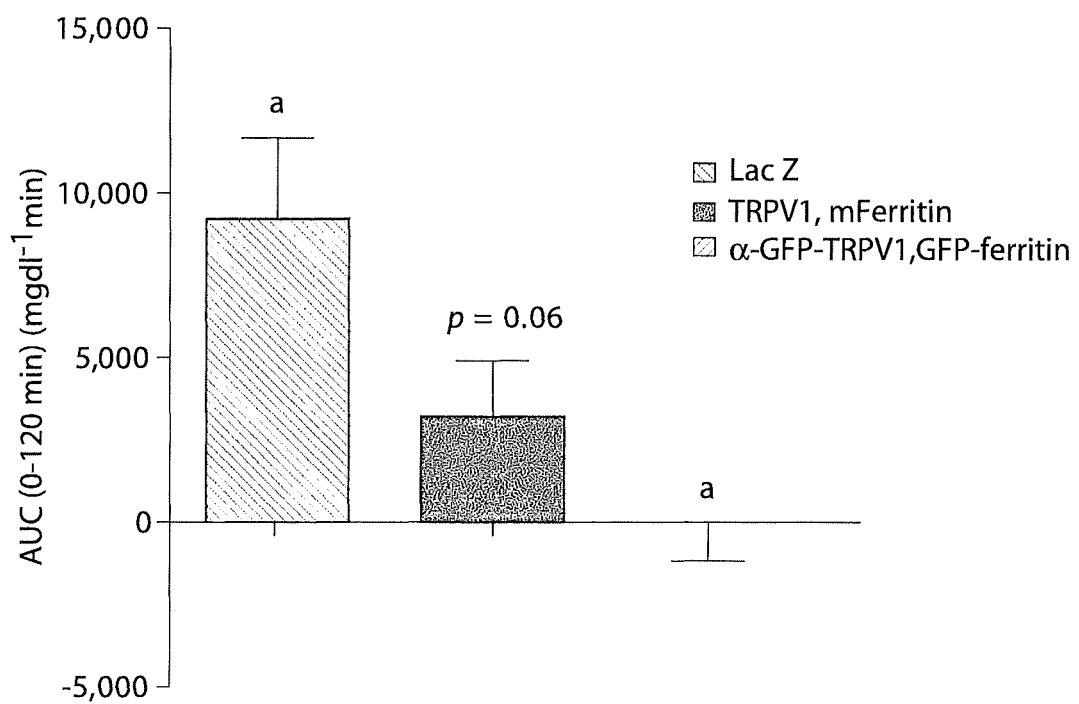
FIG. 3F is a graph showing that RF treatment significantly reduces blood glucose over the course of the study in mice expressing αGFP-TRPV1/GFP-ferritin compared to RF treatment of mice expressing Lac Z. Same letter indicates p<0.05. Error bars indicate SEM.

Next, we generated replication deficient adenovirus strains expressing TRPV1/myrferriti n or αGFP-TRPV1/GFP-ferritin under the control of a cytomegalovirus (CMV) promoter followed by a stop cassette and the calcium-dependent insulin transgene (FIGS. 2A and B). These adenoviruses were injected intravenously into STZ-treated C57B16 mice resulting in hepatic expression of the constructs (FIGS. 3A and B). RF treatment of fasted mice expressing both TRPV1/ferritin constructs significantly increased hepatic insulin gene expression (FIG. 3C) (TRPV1/myrferritin: 2.3±0.4 relative insulin gene expression vs. 1.0±0.4 basal, $p<0.05$ and αGFP-TRPV1/GFP-ferritin: 4.1±0.8 relative insulin gene expression vs. 1.0±0.1 basal, $p<0.05$). Plasma insulin also rose significantly with RF treatment in these mice but not in control mice (FIG. 3D). While the control showed a substantial increase in blood glucose over the course of the study as a result of the well-established effect of anesthesia to elevate plasma glucose15, RF treatment of mice expressing TRPV1/myrferritin or αGFP-TRPV1/GFP-ferritin significantly reduced blood glucose (FIG. 3E) and lowered the cumulative change in blood glucose over the course of the study (FIG. 3F) (AUC (0-120 min). Expression of the apoptotic protein caspase-3 in RF treated livers did not change (FIG. 2C). Therefore, RF treatment of mice with viral mediated expression of TRPV1/ferritin constructs is also effective at modulating gene expression and protein release in vivo. Here again the αGFP-TRPV1/GFPferritin displayed greater sensitivity to RF treatment compared to the TRPV1/myrferritin construct.

Figure 4A:
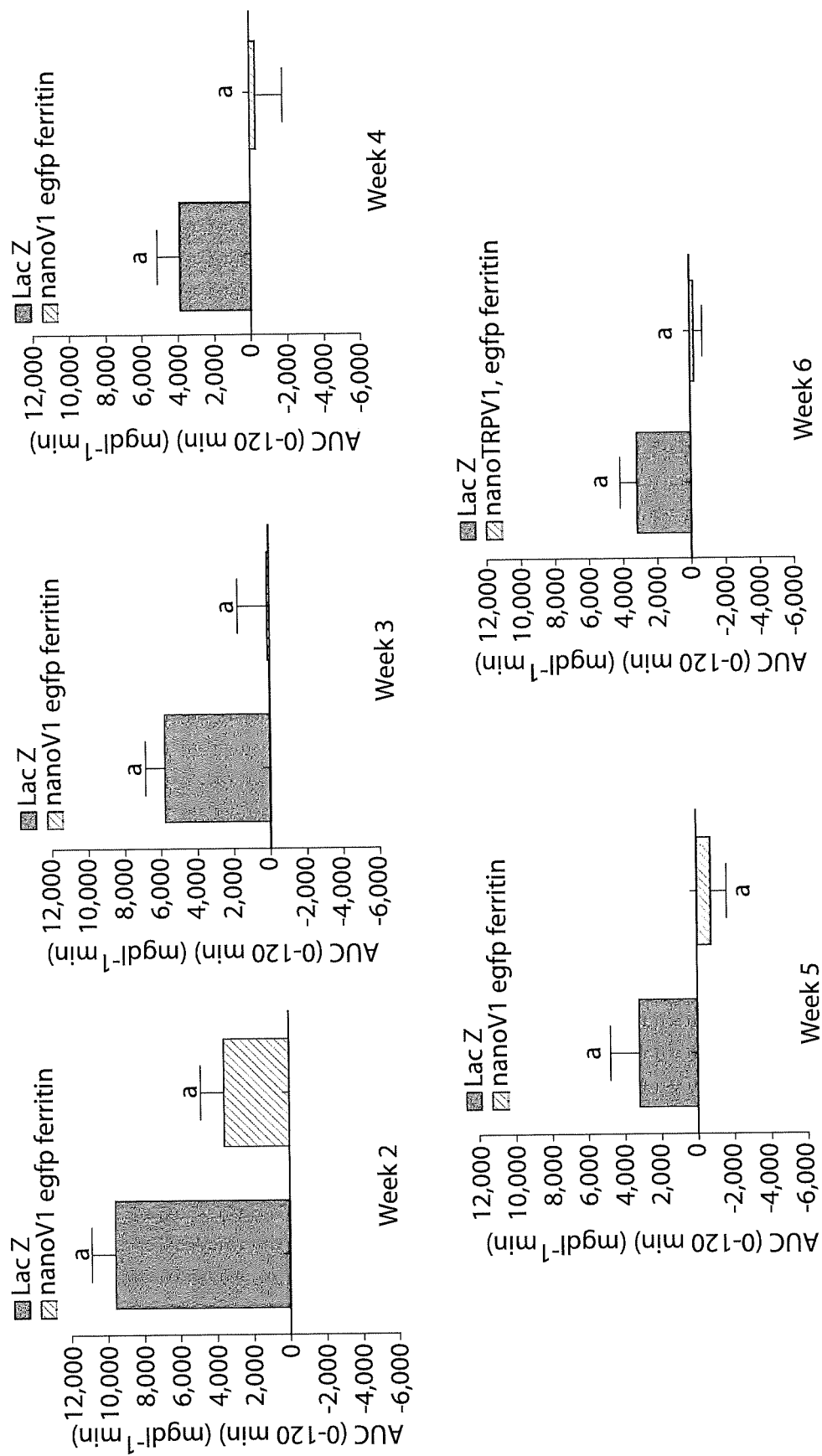
FIG. 4A presents graphs showing the effects of RF treatment at weeks 2, 3, 4, 5 and 6 after virus injection on cumulative blood glucose in C57Bl6 mice injected with control or αGFP-TRPV1/GFP-ferritin expressing adenovirus (labelled "nanoV1 egfp ferritin"). RF treatment significantly reduced cumulative blood glucose in αGFP-TRPV1/GFP-ferritin expressing mice at each assessment.
Figure 4B:
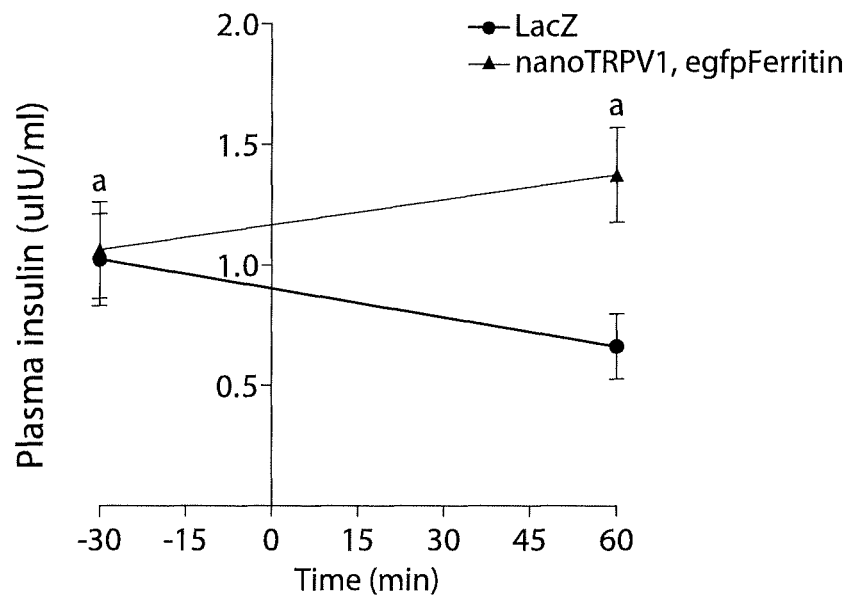
FIG. 4B is a graph showing that plasma insulin was significantly increased by RF treatment in mice expressing αGFP-TRPV1/GFP-ferritin (labelled "nanoTRPV1, egfp-Ferritin") but not in control mice at week 2. Same letter indicates p<0.05. Error bars indicate SEM.
Figure 4C:
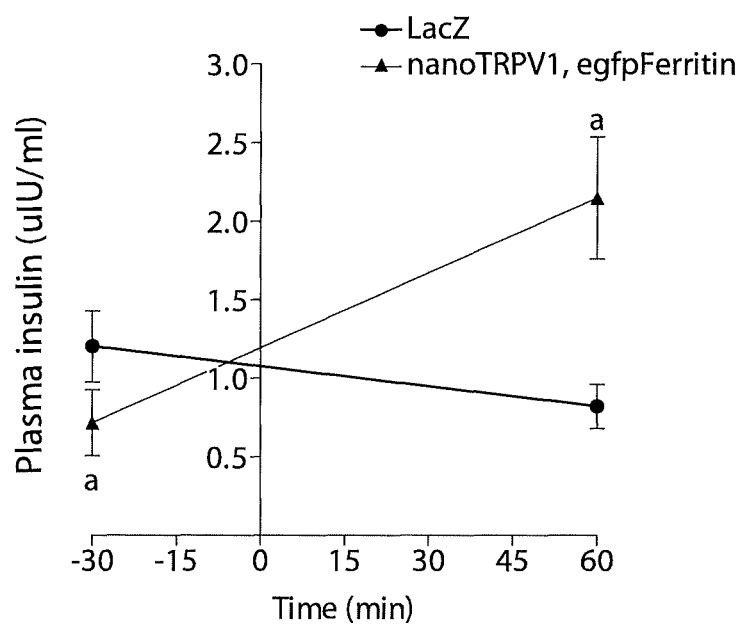
FIG. 4C is a graph showing that plasma insulin was significantly increased by RF treatment in mice expressing αGFP-TRPV1/GFP-ferritin (labelled "nanoTRPV1, egfp-Ferritin") but not in control mice at week 6. Same letter indicates p<0.05. Error bars indicate SEM.

Repeated RF treatment to regulate protein delivery to ensure that the combination of TRPV1 and genetically encoded nanoparticles were effective over time, we assessed the responses of STZ-treated C57B16 mice expressing LacZ or αGFP-TRPV1/GFPferritin and calcium dependent insulin to weekly RF treatment. Mice were injected with adenovirus expressing LacZ or αGFP-TRPV1/GFP-ferritin and calcium dependent insulin and treated with 1 h of RF once a week on weeks 2 to 6 after virus injection. RF treatment significantly reduced blood glucose and the cumulative changes in blood glucose (AUC (0-120 min)) in αGFP-TRPV1/GFP-ferritin expressing mice at all time points (FIGS. 4A and B). In addition, RF induced a significant increase in plasma insulin at both week 2 and week 6 (which were the only time points at which animals were bled and plasma insulin could be measured) (FIGS. 4B and C).

Remote activation of gene expression with a static magnetic field. In principle, exposure of ferritin nanoparticles to RF could gate TRPV1 as a result of particle heating or by increasing Brownian motion providing a mechanical stimulus to the channel[16]. The latter possibility is suggested by the finding that several ion channels in the TRPV family have been implicated in mechanosensing[17] and by calculations suggesting that the heat transfer from nanoparticles appears to be in a similar range to that required to gate the channel[10]. We thus considered the possibility that the tethered ferritin iron oxide nanoparticles, which have superparamagnetic properties[18], could transduce an external magnetic field into a mechanical force as adjacent particles align with the field[19]. We therefore tested whether an external magnetic field could activate αGFP-TRPV1 channels tethered to GFP-ferritin to regulate gene expression and protein synthesis in vitro and in vivo.

Figure 5A:
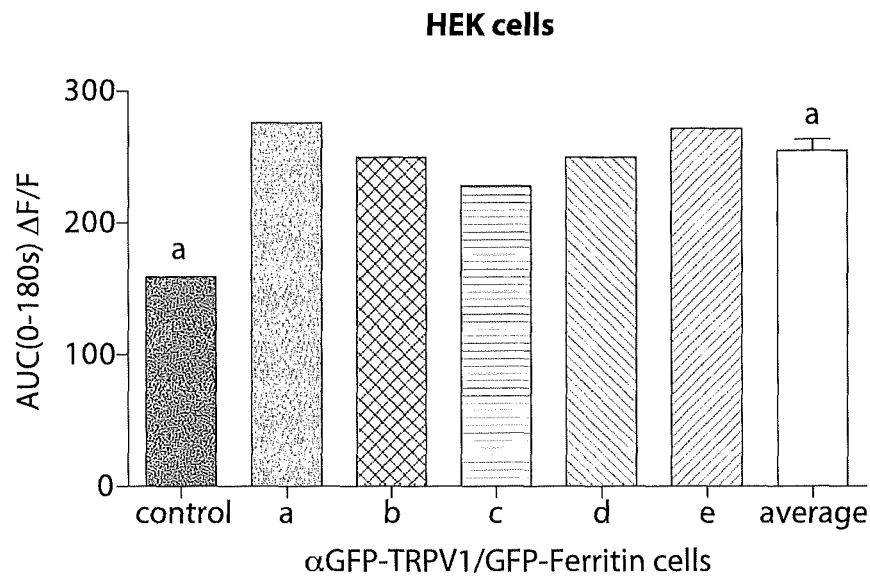
FIG. 5A illustrates the effects of magnetic field on cumulative changes in Fluo-4 fluorescence in HEK cells transfected with αGFP-TRPV1/GFP-ferritin or control cells. Same letter indicates p<0.05. Error bars indicate SEM.
Figure 5B:
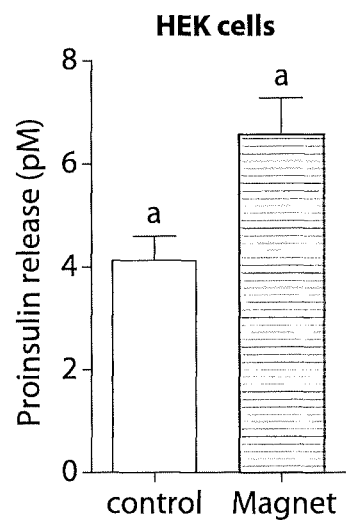
FIG. 5B is a graph showing that magnetic field treatment increases proinsulin release from HEK cells expressing αGFP-TRPV1/GFP-ferritin and calcium dependent human insulin. Same letter indicates p<0.05. Error bars indicate SEM.

Application of a static magnetic field using a standard fixed magnet (K&J magnetics Pipersville, PA) resulted in significantly increased intracellular calcium in HEK cells transfected with αGFP-TRPV1/GFPferritin. The cumulative change in relative fluorescence over 180 s of imaging (ΔF/F(AUC(0-180 s)) for αGFP-TRPV1/GFP-ferritin transfected cells was 255±8.6 and for control cells it was 159±0.6, $p<0.05$ (FIG. 5A). One-hour treatment with an intermittent magnetic field (5 s every 2 min for 1 h) also resulted in significantly greater proinsulin release from HEK cells transfected with αGFP-TRPV1/GFP-ferritin and calcium-dependent insulin vs. that of control cells not exposed to the magnet ($p<0.001$) (FIG. 5B).

Figure 5C:
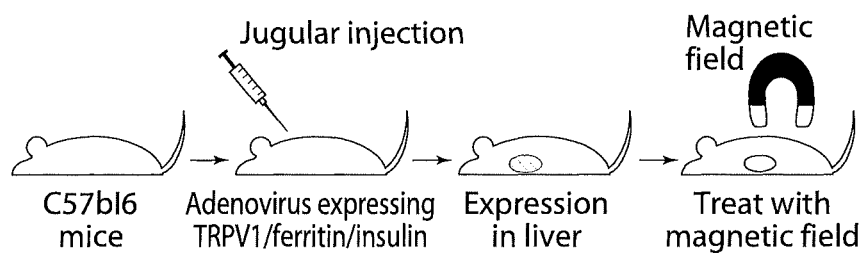
FIG. 5C is a schema for delivery and assessment of effects of magnet treatment on blood glucose in C57Bl6 mice injected with replication deficient adenovirus expressing αGFP-TRPV1/GFP-ferritin and calcium dependent human insulin.
Figure 5D:
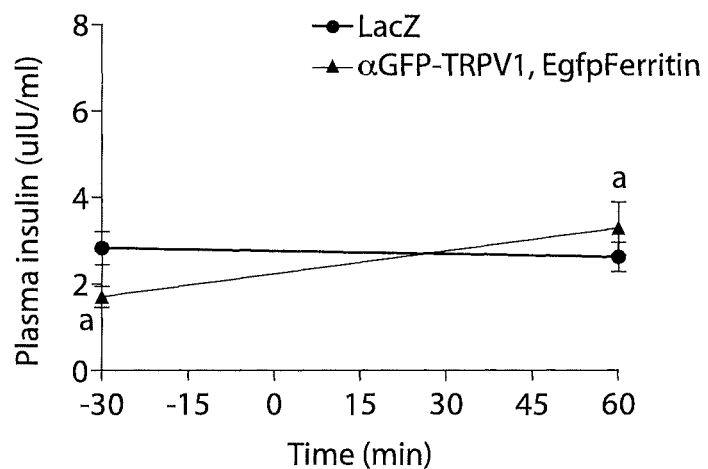
FIG. 5D is a graph showing that plasma insulin is significantly decreased in mice expressing αGFP-TRPV1/GFP-ferritin and calcium dependent human insulin treated with an intermittent magnetic field compared to no magnet treatment. Asterisks indicate p<0.05.
Figure 5E:
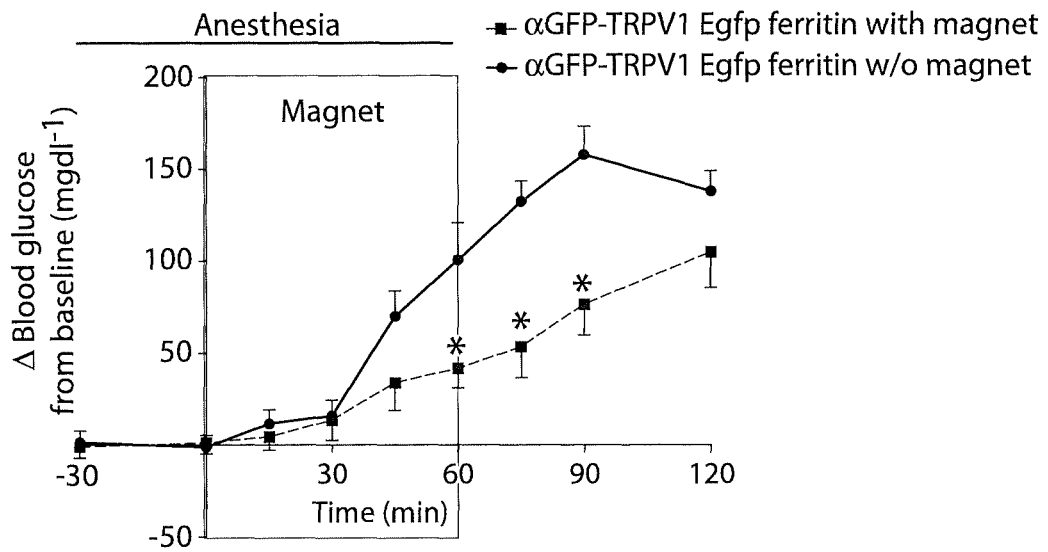
FIG. 5E is a graph showing that magnet treatment significantly reduces blood glucose over the course of the study in mice expressing αGFP-TRPV1/GFP-ferritin compared to no magnet treatment. Error bars indicate SEM.
Figure 5F:
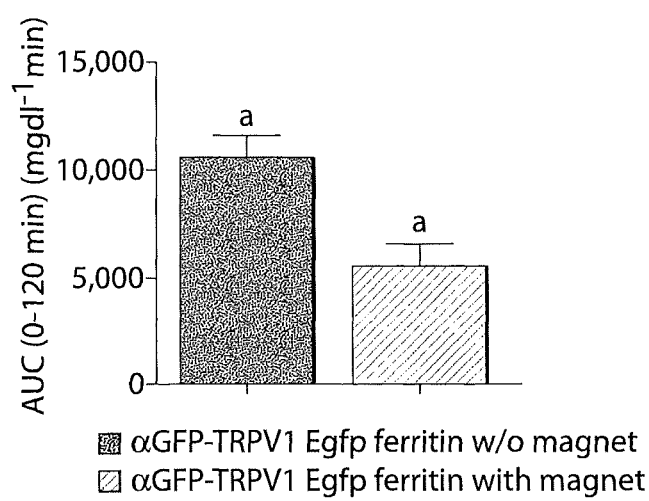
FIG. 5F is a graph showing that magnet treatment significantly reduces cumulative blood glucose over the course of the study in mice expressing αGFP-TRPV1/GFP-ferritin compared to no magnet treatment. Same letter indicates p<0.05. Error bars indicate SEM.

We next assessed the effects of magnetic activation on gene expression in vivo in a standard cross-over study (FIG. 5C). STZ-treated C57B16 mice injected with adenovirus expressing αGFP-TRPV1/GFP-ferritin and calcium dependent insulin were treated with an intermittent magnetic field (or no magnet) for 1 h. Blood glucose was significantly lower in magnet-treated mice expressing αGFP-TRPV1/GFP-ferritin adenovirus compared to control mice treated for the same period ($p<0.05$) (FIG. 5D). Cumulative blood glucose over the course of the study (AUC (0-120 min)) was significantly reduced with magnet treatment of αGFP-TRPV1/GFP-ferritin expressing mice vs. control mice ($p<0.05$) (FIG. 5E) (AUC(0-120 min). These data show that RF or a magnetic field can be used to gate a ferritin-tethered TRPV1 channel in vitro and in vivo.

Results and Discussion

Here we report the development of a genetically encoded system for regulating gene expression in vivo using either radiowaves or a magnetic field. In previous studies, we showed that functionalized, externally delivered nanoparticles can bind epitope-tagged TRPV1 channels and transduce a remote RF signal into calcium entry and gene expression in vivo. However, using this system the regulated gene expression can only be achieved in local cell populations, and repeated nanoparticle administration is needed for eliciting serial responses as a result of particle internalization. The use of a genetically encoded ferritin-tethered TRPV1 system is superior insofar as it enables remote, robust and repeated temporal control of gene expression in vivo using either non-invasive low frequency RF fields or intermittent magnetic fields to activate TRPV1 bound by a monomeric binding protein to GFP-tagged ferritin enclosing iron oxide nanoparticles. We validate this genetically encoded system by showing that it can effectively and repeatedly regulate blood glucose by controlling insulin gene expression and release in vivo. We also show that this method can be used in implanted stem cells, potentially enabling regulated expression of key proteins in engineered stem cells.

Ferritin is a heteromultimer comprised of light and heavy chains, which creates a 5-12 nm iron oxide core[20] with a complex crystalline and magnetic structure[18]. The iron oxide core heats in response to RF treatment[21] to activate TRPV1. We tested the efficiency of three ferritin locations in converting an RF field into channel activation and gene expression: cytoplasmic, membrane-tethered and channel associated.

We found GFP-tagged ferritin associated with αGFP-TRPV1 to most robustly stimulate insulin gene expression in vitro and in vivo. The amount of heat transfer from a particle decreases at $1/r^2$ with distance. The observation that the efficiency of TRPV1 activation is highest when the ferritin is directly tethered via an antibody-antigen interaction suggests that the amount of heat transferred to the particle could be limiting and channel opening decreases when the particle is at a distance (in the cytoplasm or elsewhere in the plasma membrane). Alternatively, the greater efficiency of the tethered channel could suggest that gating of the channel is a result of mechanotransduction. We tested this possibility by exposing the ferritin tethered TRPV1 to a magnetic field which will exert a mechanical force without heating. Ferritin nanoparticles are paramagnetic, which enables them to align with an external magnetic field. The core resembles a single crystal of ferric oxyhydroxide, which is superparamagnetic with an antiferromagnetic spin arrangement[18], and recent work has shown cells over-expressing ferritin are able to interact with externally applied magnetic fields[22]. Such studies suggest that tethered ferritin in a magnetic field could exert a mechanical force. Moreover, TRPV1 is a tetramer with four tethered ferritin particles that could exert a mechanical force as their orientation relative to the magnetic field either pulls them together or pushes them apart[19]. Our data thus suggest that TRPV1 can respond to a mechanical force. These data also raise the question of whether an oscillating magnetic field, such as that generated by RF activates the channel by local heating or by mechanical torque as well. Further studies will be necessary to determine the mechanism by which RF gates TRPV1 channels decorated with ferritin.

Remote systems for controlled transgene expression have great potential for numerous basic, biomanufacturing and therapeutic purposes. Investigation of the roles of gene products in defined developmental phases requires temporally controlled gene expression that can be regulated non-invasively. In the case of drug induced gene expression, estrogens[23] and tetracyclines[24] can result in embryonic toxicity. Both RF and magnetic fields penetrate tissue freely and may be useful in controlling transgene expression in fetal development. Similarly, biomanufacturing processes requiring strictly regulated gene expression would benefit from remote rather than chemically regulated gene expression[25]. Finally, gene therapies for certain disorders require tight regulation[26] or the ability to titrate transgene expression to biological response[27]. Here, non-invasive tools to regulate gene expression would be preferable and we have shown this system to be effective in regulating transgene expression in stem cell implants and in tissue with virally mediated transgene delivery. Both RF and magnetic fields have been used in clinical practice, the former for setting pacemakers[8] and the latter for the treatment of depression[28]. Finally, because TRPV1 gates $Ca^{2+}$, the data further indicate that this system can be adapted to regulate the activity of neurons and other cell types. Consistent with this idea, TRPV1 activation has previously been shown to modulate neural activity in response to specific chemical ligands[29]. The use of this genetically encoded ferritin-tethered TRPV1 can be used to non-invasively activate localized or dispersed cells in vivo using RF or a magnetic field. In summary, we have developed and validated a fully genetically encoded system for non-invasive regulation of gene expression in vivo. These studies show TRPV1 channel activation may be achieved by mechanical stimulation and show the utility of endogenously expressed nanoparticles in vivo in transducing both radiowaves and magnetic fields for non-invasive control of transgene expression.

Example 2 Bidirectional Electromagnetic Control of Hypothalamic Neurons Regulates Blood Glucose and Feeding Methods Radiofrequency Field and Static Magnetic Field A 465 kHz sinusoidal signal was provided by a signal generator and applied through an amplifier (both Ultraflex, Ronkonkoma, NY) to a 2-turn solenoid coil with a radius of 2.5 cm to produce an electromagnetic field. The field strengths tested were 31 mT, 27 mT and 23 mT. Samples were placed within the solenoid.

A static magnetic field for imaging experiments was produced using a neodymium-iron-boron permanent magnet (0.25×1 inch, axially magnetized, K&J magnetics Pipersville, PA). This was able to produce a magnetic flux density of over 5 kiloGauss at the magnet surface. Field strengths of 280 mT and 130 mT were generated by increasing the distance from the cells to the magnet surface (2 mm and 5 mm respectively). A N52 grade neodymium magnet (0.06× 0.25 inch, axially magnetized, K&J magnetics Pipersville, PA) was used for electrophysiological studies. The magnetic field for in vivo studies was generated by the superconducting electromagnetic MRI field from a GE 3.0 Tesla Excite HDx MRI Scanner (GE Healthcare; Milwaukee, WI). The field strength was measured and regions with strengths of 0.5-1 T or 0.2-0.5 T were used for in vivo studies.

Plasmids

Anti-GFP nanobody-TRPV1-2A-GFP ferritin in pEGFPN1 and MSCV-hygro were generated as previously described[30]. Mutation of residue 1679 to K in rat TRPV1 was performed by site-directed mutagenesis using QuikChange XL Site-Directed Mutagenesis Kit (Agilent, Santa Clara, CA). These sequences were cloned into pVQ Ad CMV KNpA for generation of replication deficient adenovirus. To construct Cre-activated recombinant adenovirus vectors, a DNA construct with two pairs of incompatible lox sites, loxN and lox2722, was synthesized and Anti-GFP nanobody-TRPV1-2A-GFP ferritin was cloned between the two pairs in the antisense orientation. The floxed inverted Anti-GFP nanobody-TRPV1-2A-GFP ferritin cassette was then cloned into pVQ Ad CMV KNpA for generation of replication deficient adenovirus. The fidelity of PCR products and cloning was confirmed by DNA sequencing.

Viruses

The recombinant adenoviruses (Ad-CMV-GFP, Ad-CMV-αGFP-TRPV1/GFP-ferritin, Ad-FLEX-αGFP-TRPV1/GFP-ferritin and Ad-FLEX-αGFP-TRPV1$^{Mutant}$/GFP-ferritin were packaged by Viraquest (Iowa). The final titer was $4\times10^{10}$ plaque forming units (pfu)/ml. AAV-EFla-DIO-hChR2(H134R)-EYFP was purchased from UNC Viral Core.

Cell Culture and In Vitro Studies

Human embryonic kidney cells (HEK 293T, (ATCC® CRL-3216™), mycoplasma testing and STR profiling performed by ATCC) were cultured in Dulbecco's modified eagle medium with 10% fetal bovine serum (Gibco, Carlsbad, CA) at 37° C. and 5% $CO_2$. Phoenix ecotropic packaging cells (Stanford University) were grown in Dulbecco's modified eagle medium with 10% fetal bovine serum (Gibco) at 37° C. and 5% $CO_2$. Embryonic mouse hypothalamic N38 cells (Cellutions Biosystems Inc) were grown in Dulbecco's modified eagle medium with 10% fetal bovine serum at 37° C. and 5% $CO_2$.

Stable cell lines were produced by retroviral infection of N38 cells using the Phoenix system. Briefly, Phoenix eco cells ($2\times10^6$ cells per 6-cm dish) were transfected with MSCV-hygro αGFP-TRPV1/GFP-ferritin or MSCV-hygro αGFP-TRPV1$^{Mutant}$/GFP-ferritin. After 24 hours, the medium was replaced and the cells placed at 32° C. Medium was aspirated after a further 24 h and spun to remove cell debris. The Phoenix cell supernatant was added to N38 cells (plated at $1\times10^6$ cells per 6-cm dish) using a 1:2 dilution in DMEM/10% FBS with polybrene (4 µg/ml, Sigma-Aldrich, St Louis, MO). Cells were incubated at 32° C. for a further 24 h before replacing the medium with DMEM/10% FBS. Selection medium was added 48 h after infection. Stably transfected N38 cells were maintained at 32° C.

For immunocytochemistry, electrophysiology, RF and magnet studies, stably transfected N38 cells or HEK cells were cultured on 12-mm cover glass (Fisher Scientific, Pittsburgh, PA) coated with fibronectin (10 mg/ml, Sigma). HEK cells were transfected with appropriate constructs 24 h after plating using lipofectamine 2000 (Invitrogen, Carlsbad, CA). Culture medium was replaced 18 h after transfection and holotransferrin (2 mg/ml, Sigma) was added to the cells. Cells were studied 72-96 hrs after transfection or subculture.

Effect of RF or magnet on pCREB and cFos: 24 h prior to the study, cells were placed in 1% FBS medium at 32° C. to ensure minimal activation of TRPV1 and calcium dependent pathways. On the day of study, cells were incubated in 500 µl of calcium imaging buffer at room temperature (control) or in a RF field (31 mT) at room temperature. For magnet treatment, cells were treated with a static magnetic field (280 mT) for 5 seconds every 2 minutes for 1 hour at room temperature. After 60 min, the cells were placed on ice, the supernatant removed and cells lysed with RIPA buffer (40 µl, pCREB) or lysis buffer (100 µl Agilent Absolutely RNA microprep kit) and frozen at −80° C. until assay or RNA purification. Each study was repeated on 3 occasions each with 4 replicates. Control studies with N38 cells alone were performed on 2 occasions with 4 replicates.

Calcium Imaging

TRPV1 is a non-selective cation channel with relatively high permeability to divalent cations, particularly calcium (Ca2+>Mg2+>Na+K+Cs+)[55]. For studies examining the effects of RF (31 mT) or magnet (280 mT) with and without Ruthenium red, stably transfected cells were washed three times in PBS then loaded with Fluo-4 3 µM (Invitrogen) in the presence of sulfinpyrazone 500 µM (Sigma) for 45-60 min at room temperature. Cells were washed again in PBS then incubated for 15-30 min in sulfinpyrazone in PBS. Cells were washed and then imaged in calcium imaging buffer. Imaging was performed using a Deltavision personal DV imaging system (Applied Precision, Issawaq, WA) equipped with a custom-made ceramic lens. Images were acquired every 3 seconds for 3 minutes. Cells were imaged without treatment (8 occasions), before and during RF treatment (9 occasions), before and during application of a neodymium magnet (for 45 sec, 3 occasions) or before and after treatment with 200 µM 2-aminoethoxydiphenyl borate (2-APB, 2 occasions). Imaging was repeated in the presence of Ruthenium red (100 µM) (2 occasions for each condition). Images were analyzed using Image J software.

For studies to examine the effects of increasing RF or magnet field strength, to assess the effects of short RF treatment (10s) on calcium responses and to examine the kinetics of the calcium response, cells were loaded with FluoForte 20 µM (Enzo Life Sciences, Lorrach, Germany) in the presence of Pluronic F-127 (0.02% vol/vol) and sulfinpyrazone 500 µM. Cells were washed and then imaged in calcium imaging buffer. Imaging was performed as above with images acquired every second for 1 minute. Cells were imaged without treatment (4 occasions), before and during RF treatment at 31, 27 and 23 mT (4 occasions each), before and during application of a neodymium magnet at 280 or 130 mT (magnet 2 mm or 5 mm from the cells respectively, 4 occasions each) and before, during and after 10 second treatment with RF (31 mT) (4 occasions). Images were analyzed using Image J software.

Multiphoton Chloride Imaging

Stably transfected cells were washed with Krebs-HEPES buffer 3 times then loaded with MQAE (N-(Ethoxycarbonylmethyl)-6-Methoxyquinolinium Bromide, 5 mM, Invitrogen) for 60 min at room temperature. The cells were washed with Krebs-HEPES buffer and then incubated in buffer for 15 min before imaging. Imaging was performed using LSM 510 NLO inverted multiphoton and confocal system (Zeiss) using a 40× objective with two photon excitation at 750 nm. Cells were imaged without treatment (4 occasions), before and during application of a neodymium magnet (280 mT) for 20 sec (on 6 occasions), before and after treatment with 200 µM 2-aminoethoxydiphenyl borate (2-APB, 2 occasions). Imaging was repeated in the presence of Ruthenium red (100 µM) (2 occasions for each condition). Images were analyzed using Image J software.

Immunocytochemistry and Immunohistochemistry

Immunocytochemistry (ICC) and immunohistochemistry (IHC) were used to detect expression of TRPV1, GFP and FLAG-tagged ferritin, to localize c-fos expression and to quantify apoptosis in cells and tissue. Cells were washed twice in PBS and then fixed for 15 min in 2% paraformaldehyde (Electron Microscopy Services, Hatfield, PA). Tissue was fixed in 10% formalin (Sigma) at 4° C. overnight and 40 nm sections cut on a vibrating microtome. Fixed cells or tissue sections were washed then incubated for 1 h in blocking buffer (3% BSA (Sigma) and 2% goat serum (Sigma) in PBS with 0.1% Triton-X (Sigma)). Cells and tissues were then incubated in primary antibody (rabbit anti-TRPV1 1:500 (AB95541, Chemicon), mouse anti-FLAG 1:1000 (FLAG-tag Mouse mAb #8146P, Cell signaling), chicken anti-GFP 1:1000 (ab139703, Abcam), rabbit anti-activated caspase 3 1:250 (G7481, Promega4)) or rabbit anti-cFos 1: (PC38, Calbiochem) diluted in blocking buffer overnight at 4 degrees. Cells or tissue were washed three times in PBS/0.1% Triton-X before incubation in secondary antibody (goat anti-rabbit 594 (A1012) or goat anti-rabbit 488 (A11008), goat anti-chicken 488 (A11039), goat anti-mouse 350 (A11045), all 1:1000) diluted in blocking buffer for 2 h. The cells or tissue were washed a further three times in PBS/0.1% Triton-X before mounting using Fluoromount (Southern Biotech, Birmingham, AL).

Images were acquired using confocal microscopy (LSM 510 laser scanning confocal microscope; Carl Zeiss Micro-Imaging, Inc.). Confocal fluorescence images were acquired on a scanning laser microscope using a 20×/0.70NA objective. To quantify GFP positive and activated caspase-3 positive cells, a 1280 m section of the brain with the injection site taken as the center was imaged by taking tiled, serial stack images covering a depth of 40 μm every 320 μm. Quantification of GFP and active caspase-3 immunostaining was performed by an investigator blinded to the treatment group using Imaris 3D quantification software (Zurich, Switzerland). The image analysis software calculated the number of GFP or activated caspase-3 positive cells per volume by thresholding immunoreactivity above background levels. Confocal images to examine co-localization of TRPV1, GFP and FLAG-tagged ferritin were acquired with a 40× objective.

ImmunoEM

Mouse brain was perfused by 4% PFA and sectioned at 50 μm by vibratome (Leica VT 100S). The sections were blocked by 4% BSA and 0.15% saponin in 20 mM Tris buffer (pH 7.4) for 2 hr at room temperature, then incubated with anti-GFP (1:1000) (Aves Lab Inc.) overnight at 4° C., followed by biotinylated anti-chicken incubation (1:1000, Vector Laboratories, Inc.), with Nanogold streptavidin (1:100, Nanoprobes, Yaphank, NY), a treated with Gold-Ehance EM (#2114 Nanoprobes). Negative control was done with the same procedure, except for omitting the primary antibody incubation. The tissue sections underwent fixation with 2% glutaraldehyde in sodium cacodylate buffer, light osmication (0.5% osmium tetroxide) for 15 min and en block staining with 1% uranium acetate for 30 min. Subsequently tissues were dehydrated through an ethanol series followed by incubation with Eponate12 (Ted Pella Inc.) The samples were embedded in the resin and polymerized at 60 degrees C. for 48 hr. Ultrathin (70 nm) sections were cut and examined under a JEOL JEM 100CX transmission electron microscope in the electron microscopy center in The Rockefeller University.

Electrophysiology

Cell Culture

Whole cell voltage clamp recordings were made at room temperature at −60 mV from cultured HEK cells and N38 cells expressing αGFP-TRPV1/GFP-ferritin or αGFP-TRPV1Mutant/GFP-ferritin construct. Neurons expressing GFP were visualized using epifluorescence on an upright Zeiss Axioskop 2FS Plus microscope equipped with a Hamamatsu CCD camera. External solution contained (in mM): 140 NaCl, 2.8KCl, 2CaC2, 1 $MgCl_2$, 1HEPES, 10 glucose, pH 7.4. Patch pipettes pulled from borosilicate glass (World Precision Instruments) had tip resistances of 5-10 MΩ and were filled with K-gluconate internal containing (in mM): 135 potassium gluconate, 4 KCl, 0.05 EGTA, 10 Hepes, 4 MgATP, 10 Na—.

Phosphocreatine, pH adjusted to 7.3 with KOH, 290 OSM unless otherwise stated, in which case a CsCl internal solution was used containing (in mM):125 CsCl, 10 HEPES, 10 EGTA, 4 MgATP, 0.5 $CaCl_2$ 2APB (200 μM) was prepared from a 10 mM DMSO stock and was perfused though the bath when stated. I-V relationships were obtained by measuring current responses to increasing 5 mV steps in the presence of 200 μM 2APB. Cells were held at −60 mV. Magnetic activation was applied by bringing a permanent magnet within 500 microns of the recorded cell for 5 seconds with a micromanipulator. Recordings were acquired with an Axopatch 200B amplifier, filtered to 2 kHz and digitized at 10 kHz (pClamp software, Molecular Devices). Data were analyzed using IGOR Pro (Wavemetrics) and NeuroMatic. (neuromatic.thinkrandom.com). Series resistance was monitored and not compensated for. If there was more than a 20% change in series resistance the recording was excluded.

Slice Electrophysiology

Glucokinase-cre Rosa-TdTomato, injected with Ad-αGFP-TRPV1/GFP-ferritin or Ad-αGFP7 TRPV1Mutant/GFP-ferritin in the VMH were deeply anesthetized with isoflurane prior to decapitation and removal of the entire brain to be immediately submerged in ice-cold 'slicing' solution containing (in mM): 85 NaCl, 2.5 KCl, 0.5 $CaCl_2$, 4 $MgCl_2$, 25 $NaHCO_3$, 1.25 $NaH_2PO_4$, 64 sucrose, 25 glucose and 0.02 D-2-amino-5-phosphonopentanoic acid (D-AP5, Tocris Bioscience). This was bubbled with 95% $O_2$ and 5% $CO_2$, pH 7.4. Coronal hypothalamic slices (200 μm) were made with a moving blade microtome (VT1000S, Leica). The slices were kept at 32° C. for 40 min in recording solution containing (in mM) 125 NaCl, 2.5 KCl, 1.25 $NaH_2PO_4$, 26 $NaHCO_3$, 10 glucose, 2 $CaCl_2$) and 1 $MgCl_2$, pH 7.4 when bubbled with 95% $O_2$ and 5% $CO_2$. Whole-cell current clamp patch-clamp recordings were made at room temperature from neurons in the VMH expressing both td-tomato and GFP indicating expression of the αGFP-TRPV1/GFP-ferritin or αGFP-TRPV1Mutant/GFP-ferritin construct. Neurons were visualized and recorded from as described above. In order to observe neuronal activation, neurons were hyperpolarized to below threshold.

Baseline characteristic for hypothalamic neurons are as follows. Mean series resistance for neurons expressing the construct was 18.4±1.1MΩ (n=37) and did not differ significantly from hypothalamic neurons that did not express the construct (18.0±1 n=7). The mean capacitance was 5.1±0.55 pF and did not differ significantly from neurons not expressing the channel (6.7±0.8) The mean resting membrane potential in naïve hypothalamic neurons was −48.21±4.7 mV (n=15) and in cells expressing the construct before manipulation was −52 mV±1.9 mV n=37 p>0.5. Input resistances did not significantly differ in hypothalamic neurons; control neuron (without construct expression) =703±128 MΩ (n=13), wildtype channel neuron=555±110 MΩ (n=7), mutant neuron=866±220 MQ+(n=14).

Animals and In Vivo Studies

C57B16 mice (8-9 weeks, Jackson laboratories, Bar Harbor, MA), Nestin cre (8-9 weeks, Jackson Labs) and glucokinase cre (8-16 weeks) were used and housed under controlled light conditions (12 h light/12 h dark) and temperature (22° C.), single-caged, and fed ad libitum on standard mouse chow. Animal care and experimental procedures were performed with the approval of the Animal Care and Use Committee of Rockefeller University (protocols 12561 and 14712) under established guidelines. In all cases, mice were randomized according to body weight. The investigator was not blinded to the treatment group.

The sample size required was estimated to be n=8-10 per group on the basis of previous studies examining the effects of RF treatment on gene expression and protein release. All surgeries were performed under aseptic conditions. Mice were anaesthetized using 1.5% isoflurane and the top of the head was shaved then cleaned with 70% ethanol. An incision was made in the midline and small craniotomies were made using a dental drill.

Study 1: Wildtype mice underwent stereotacic injection into the striatum (co-ordinates: +1 AP, 2.3 ML, −3.3 DV) with Ad-CMV-GFP or Ad-CMV-αGFP-TRPV1/GFP-ferritin ($4\times10^8$ pfu/injection) over 10 minutes. The needle remained in position for a further 5 minutes before being withdrawn. Mice also received a lateral ventricle injection of iron dextran (4 ul, co-ordinates: −0.46 AP, 1.2 ML, −2.0 DV).

After 1 week or 4 weeks, mice injected with Ad-CMV-αGFP-TRPV1/GFP-ferritin were randomized to RF or no RF treatment (n=4 per time point and per treatment group). All mice treated with Ad-CMV2 GFP were treated with RF (n=4/time point) Mice were anesthetized with tribromoethanol (200 mg/kg) and after 15 min, mice were treated with RF (Ad-GFP and Ad-CMV-αGFP-TRPV1/GFP-ferritin, RF treated group) for 30 min by placing in the RF solenoid. Ad-CMV-αGFP-TRPV1/GFP-ferritin, untreated group were anesthesized and 15 min after the induction of anesthesia were placed in the RF solenoid without power for 30 min. One hour after the being placed in the solenoid, mice were perfused, brains removed and tissue processed for GFP and activated caspase-3 immunostaining as described above.

Unilateral striatal injections were used to test our construct primarily because we thought that either basal activity in the absence of RF or significant toxicity and apoptosis would result in motor changes that are readily detectable. In addition, striatum does not express TRPV1 and we wanted to ensure any effect was the result of expressing our construct rather than a result of an effect of endogenous TRPV1.

Finally, for RF treatment the mice needed to anesthetized and in pilot studies we found that anesthetics often led to high levels of c-fos activation in many CNS regions but not in the striatum. Thus, to minimize the possibility that the anesthetic was contributing to either toxicity or non-specific staining, we used striatal injections in addition to assessing the VMH.

Study 2: Nestin cre or wildtype mice were received striatal injections of Ad-FLEX-αGFP-TRPV1/GFP-ferritin ($4\times10^8$ pfu/injection) and ICV iron dextran as described above. After 1 week, mice were anesthetized, treated with RF for 30 min and perfused after 1 hour as described above. Tissue was processed for GFP and cFos immunostaining as described above.

Study 3: Glucokinase cre or wildtype mice were anesthetized with isofluorane and underwent stereotactic injection of iron dextran into the lateral ventricle (as above) and Ad-FLEX-αGFP23 TRPV1/GFP-ferritin ($4\times10^8$ pfu/injection) into the ventromedial hypothalamus (co-ordinates:−0.9 AP, 0.32 ML and −5.48 DV). After 1 week, half the mice in each group were studied using RF stimulation (31 mT) and half remained untreated. One week later, the previously treated mice were assessed without RF treatment and the previously untreated mice were treated with RF (n=13 GK-cre and n=10 WT). Tail vein samples for blood glucose were taken at −5, 0, 5, 10, 20, 30, 45, 60 and 90 min after the onset of RF treatment. After an additional week, mice were treated as described above but at 60 mins after the onset of RF treatment, mice were sacrificed and blood taken by cardiac puncture for hormone assessment and hepatic tissue was harvested and snap frozen in liquid nitrogen for later assessment of gluconeogenic enzyme expression. Brains were fixed, sectioned and stained with GFP to check injection placement. Mice with injection sites outside the VMH were excluded from the analysis.

Study 4: GK-cre mice (n=4) were anesthetized and injected with AAV-EF1a-DIO-hChR2(H134R)-EYFP (1 ul) into the VMH using the co-ordinates above. An optic fiber was then placed 200 nm above the injection site and fixed with adhesive cement followed by dental cement then the scalp was sealed back using tissue adhesive. After 4 weeks, half the mice were treated with 473 nm laser stimulation (5 Hz, 15 ms pulse width) for 30 min and half were attached to the optical cable but without light stimulation. One week later, the previously treated mice were assessed without light treatment and the previously untreated mice were treated with light. Tail vein samples for blood glucose were taken at −5, 0, 5, 10, 20, 30, 45, 60 and 90 min after the onset of light treatment. Brains were fixed, sectioned and stained with GFP to check injection placement. Mice with injection sites outside the VMH were excluded from the analysis.

Study 5: Glucokinase cre or wildtype mice were anesthetized with isofluorane and underwent stereotactic injection of iron dextran into the lateral ventricle (as above) and Ad-FLEX-αGFP TRPV1Mutant/GFP-ferritin ($4\times10^8$ pfu/injection) into the VMH. After 1 week, half the mice in each group were studied using RF stimulation (31 mT) and half remained untreated. One week later, the previously treated mice were assessed without RF treatment and the previously untreated mice were treated with RF (n=13 GK-cre and n=8 WT). Tail vein samples for blood glucose were taken at −5, 0, 5, 10, 20, 30, 45, 60 and 90 min after the onset of RF treatment. After a further 3 days, mice were anesthetized and at time 0 were treated with 2-deoxyglucose (400 mg/kg, ip) then treated with RF for 45 mins. Tail vein samples for blood glucose were taken at −5, 0, 5, 10, 20, 30, 45, 60 and 90 min after the onset of RF treatment. One week later, mice were anesthetized and RF treated (31 mT) and at 60 min after the onset of RF treatment, they were sacrificed and blood taken by cardiac puncture for hormone assessment and hepatic tissue was harvested and snap frozen in liquid nitrogen for later assessment of gluconeogenic enzyme expression. Brains were fixed, sectioned and stained with GFP to check injection placement. Mice with injection sites outside the VMH were excluded from the analysis.

Study 6: Glucokinase cre or wildtype mice were anesthetized with isofluorane and underwent stereotactic injection of iron dextran into the lateral ventricle and Ad-FLEX-αGFP-TRPV1/GFP-ferritin ($4\times10^8$ pfu/injection) into the ventromedial hypothalamus (as above) (n=6). After 1 week, mice were placed in a plastic chamber in a low strength magnetic field (<0.005 T) for a 15 min acclimation period, then half the mice were moved to a high-strength magnetic field (>0.5 T) for 30 min and half remained in the low strength field. After 30 min, all mice were placed in a low strength field for a further 30 min.

Tail vein samples for blood glucose were taken at −5, 0, 15, 30, 45 and 60 min after the acclimation period. One week later, groups were crossed so the mice previously treated with high strength magnetic field were treated with low strength field and mice previously treated with low strength field were treated with high strength magnetic field. At the end of the study, mice were sacrificed and perfused.

Brains were fixed, sectioned and stained with GFP to check injection placement. Mice with injection sites outside the VMH were excluded from the analysis.

Study 7: Glucokinase cre or wildtype mice were injected and recovered as 1 study 6 (n=6). After 1 week, the effect of magnetic field stimulation on food intake was examined. Mice were acclimated to their chamber for 20 mins then food intake was assessed after 20 min at low strength magnetic field. Food intake was then measured for 20 min with half the mice in high strength magnetic field (0.5-1 T) and half at low strength magnetic field. Food intake was measure for a final 20 min period at low strength magnetic field. One week later, the groups were crossed so mice previously treated with high strength magnetic field were treated with low strength field and mice previously treated with low strength field were treated with high strength magnetic field. At the end of the study, mice were sacrificed and perfused. Brains were fixed, sectioned and stained with GFP to check injection placement. Mice with injection sites outside the VMH were excluded from the analysis.

Study 8: Glucokinase cre mice (n=6) underwent stereotactic injection as described in study 3. After 1 week, mice were anesthetized and 15 min after the induction of anesthesia were placed in the RF solenoid without power for 30 min (no RF treatment). After 3 days, the mice were divided into 2 equal groups, one group was treated with a field strength of 27 mT for 30 minutes and the other group with a field strength of 23 mT for 30 minutes. After a further 4 days, the treatment groups were reversed. A week later, the first group of mice were treated with RF (31 mT) for 20 minutes and the second group of mice with RF (31 mT) for 10 minutes. After a further 3 days, the treatment groups were reversed. Tail vein samples for blood glucose were taken at −5, 0, 5, 10, 20, 30, 45, 60 and 90 min after the onset of RF treatment for all studies. After an additional week, half the mice were treated with RF (31 mT) for 20 minutes and half the mice remained untreated. At 60 mins after the onset of RF treatment, mice were sacrificed and brains were fixed, sectioned and stained for GFP and activated caspase 3 to assess apoptosis in the VMH.

Study 9: Glucokinase cre mice (n=6) underwent stereotactic injection as described in study 3. After 2 weeks, the effects of lower magnetic strength (0.2-0.5 mT) on food intake were assessed. Mice were acclimated to their chamber for 20 minutes and then food intake was assessed after 20 min at low strength magnetic field followed by food intake measurement after 20 min treatment with a 0.2-0.5T magnetic field. Food intake was measure for a final 20 min period at low strength magnetic field. At the end of the study, mice were sacrificed and perfused. Brains were fixed, sectioned and stained with GFP to check injection placement.

Study 10: Glucokinase cre mice (n=4) underwent stereotactic injection as described in study 5 but with bilateral injection of Ad-FLEX-αGFP-TRPV1Mutant/GFP-ferritin into the VMH. After a week, food intake was assessed in response to low magnetic field treatment. Mice were acclimated to their chamber for 20 minutes and then food intake was measured for 3 periods of 20 minutes at low field strength. One week later, the study was repeated with a 20 minute acclimation period then food intake was measured for mice were treated with high strength magnetic field (0.5-1 T) for 20 minutes. Food intake was measured for a further two 20 minute periods at low magnetic field strength. At the end of the study, mice were sacrificed and perfused. Brains were fixed, sectioned and stained with GFP to check injection placement.

Study 11: Glucokinase cre/Rosa Td-tomato mice (n=4) underwent stereotactic surgery as described in study 3. After 1 week, 3 mice were anesthetized and 15 min after the induction of anesthesia were treated with RF (31 mT) for 30 minutes. At 60 mins after the onset of RF treatment, mice were sacrificed. Brains from three mice were fixed, sectioned and stained for GFP and c-fos. The fourth mouse was perfused without RF treatment and the brain was used for immunoEM.

Assays

Blood glucose was determined using a Breeze 2 glucometer (Bayer; Leverkusen, Germany). Blood was spun for 10 min and plasma was collected. Plasma levels of insulin (Mercodia, Winston Salem, NC) and glucagon, (Mercodia) were determined by ELISA.

Western Blot

Protein was isolated by lysis in RIPA buffer and centrifugation at 16000 rpm, 4° C. for 5 min before addition of 4× Laemelli buffer. Samples were denatured for 5 mins at 95° C. and frozen at −20° C. before assay. Samples (15 ul) were run on a 4-15% gel then transferred to PVDF membrane. Membranes were blocked (3% dried milk in TBST buffer) for 1 hour at room temperature then incubated in primary antibody (Phospho-CREB (Ser133) (87G3) Rabbit mAb (1:1000) or beta Actin Rabbit Ab (1:1000), Cell Signaling) in TBST overnight at 4 degrees. Membranes were washed 3 times in TBST then incubated in secondary antibody (goat anti-rabbit IgG-HRP, 1:5000, Santa Cruz) in block for 2 hour at room temperature. The membrane was washed a further 5 times then developed in substrate for 5 min (Supersignal West Femto maximum sensitivity substrate, Life Technologies) and imaged (C-DiGit blot scanner, Licor). The pCREB density signal was corrected for any variation in protein loading by dividing by the density signal for the housekeeping gene, actin.

Real-Time PCR

Total RNA was isolated by homogenizing tissue in TRIzol reagent (Invitrogen) or cells in buffer RLT and purifying the RNA using Absolutely RNA microprep kit (Agilent). Complimentary DNA was synthesized using QIAGEN omniscript RT kit. Real-time PCR was performed using the TaqMan system (Applied Biosystems; Foster City, CA) according to the manufacturer's protocol.

Statistics

Data over 2 SD outside the mean were excluded from further analysis as determined prior to the studies. All data were tested for Gaussian distribution and variance. Data with normal distribution and similar variance were analyzed for statistical significance using two-tailed, unpaired Student t-test unless otherwise indicated. Data with normal variation and unequal variance were analyzed by two-tailed Welch's t-test. Paired data were analyzed by paired t-test. Data with more than two groups were analyzed by one-way ANOVA with post-hoc Tukey's analysis for parametric data. Data which were not normally distributed were analyzed by two-tailed Mann-Whitney test or Kruskal-Wallis with post-hoc Dunn's correction. P values are as indicated. Time course data were analyzed by 2 way Anova with Sidak's multiple comparisons or repeated measures 2 way Anova with Sidak's multiple comparisons for paired data. Data is shown as mean±SEM unless otherwise stated.

Results and Discussion

We describe a system for non-invasive, temporal control of neuronal activity in vivo and its use to study central nervous system (CNS) control of glucose homeostasis. Neuronal activation was achieved remotely with radio waves (RF) or magnetic fields via targeted expression of a GFP-ferritin fusion protein (GFP-ferritin) tethered to the cation-conducting transient receptor potential vanilloid 1 by a camelid anti-GFP antibody (αGFP-TRPV1)1. Neuronal inhibition via the same stimuli was achieved by mutating the TRPV1 pore, rendering the channel chloride-permeable. Activation of glucose-sensing neurons in the ventromedial hypothalamus (VMH) using this system increased plasma glucose and glucagon, lowered insulin and stimulated feeding, while inhibiting these neurons reduced blood glucose, raised plasma insulin and suppressed feeding. These results show that glucose-sensing neurons in the VMH can control glucose homeostasis via effects on insulin and glucagon secretion suggesting that pancreatic hormones function as an effector mechanism of CNS circuits controlling blood glucose and behavior. The method we employed also obviates the need for permanent implants and could potentially be applied to study other neural processes or used to regulate other, even dispersed cell types.

Figure 6A:
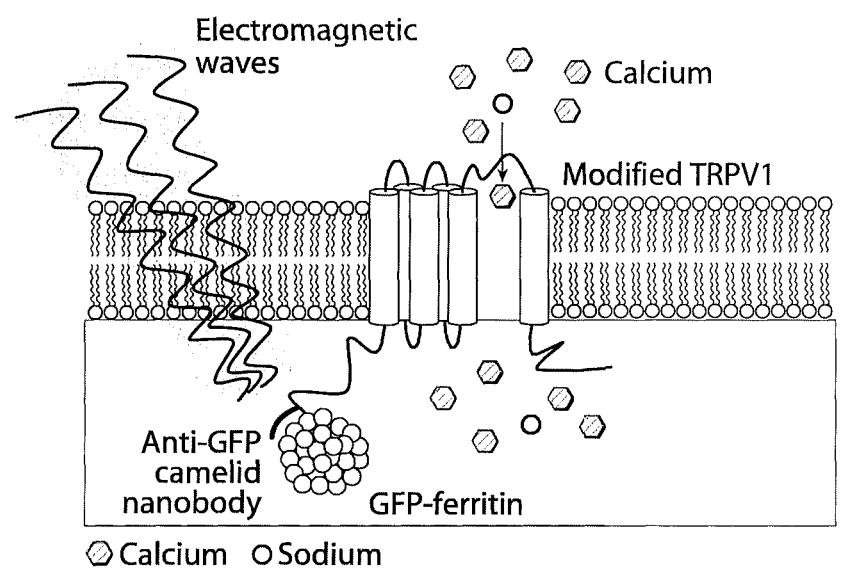
FIG. 6A is a schema of neural activation system with GFP-tagged ferritin chimera tethered to N-terminal anti-GFP TRPV1 fusion protein.

Numerous studies have established CNS regulation of peripheral metabolism2,3. While the VMH has been suggested to play an important role in controlling food intake and body weight4, electrode stimulation and lesioning studies did not distinguish between effects on local cells or fibers of passage[31,34-36] or define the contributing cell types[37]. Previously we showed that $Ca^{2+}$ entry and gene expression could be controlled using radiowaves or a magnetic field by tethering ferritin nanoparticles to the temperature sensitive TRPV1 channel[30]. However, these previous studies did not test the efficiency of this approach for controlling neural activity (FIG. 6A). We thus tested our approach in studies of the roles of specific glucose-sensing neurons in the VMH to control blood glucose in vivo.

Figure 6B:
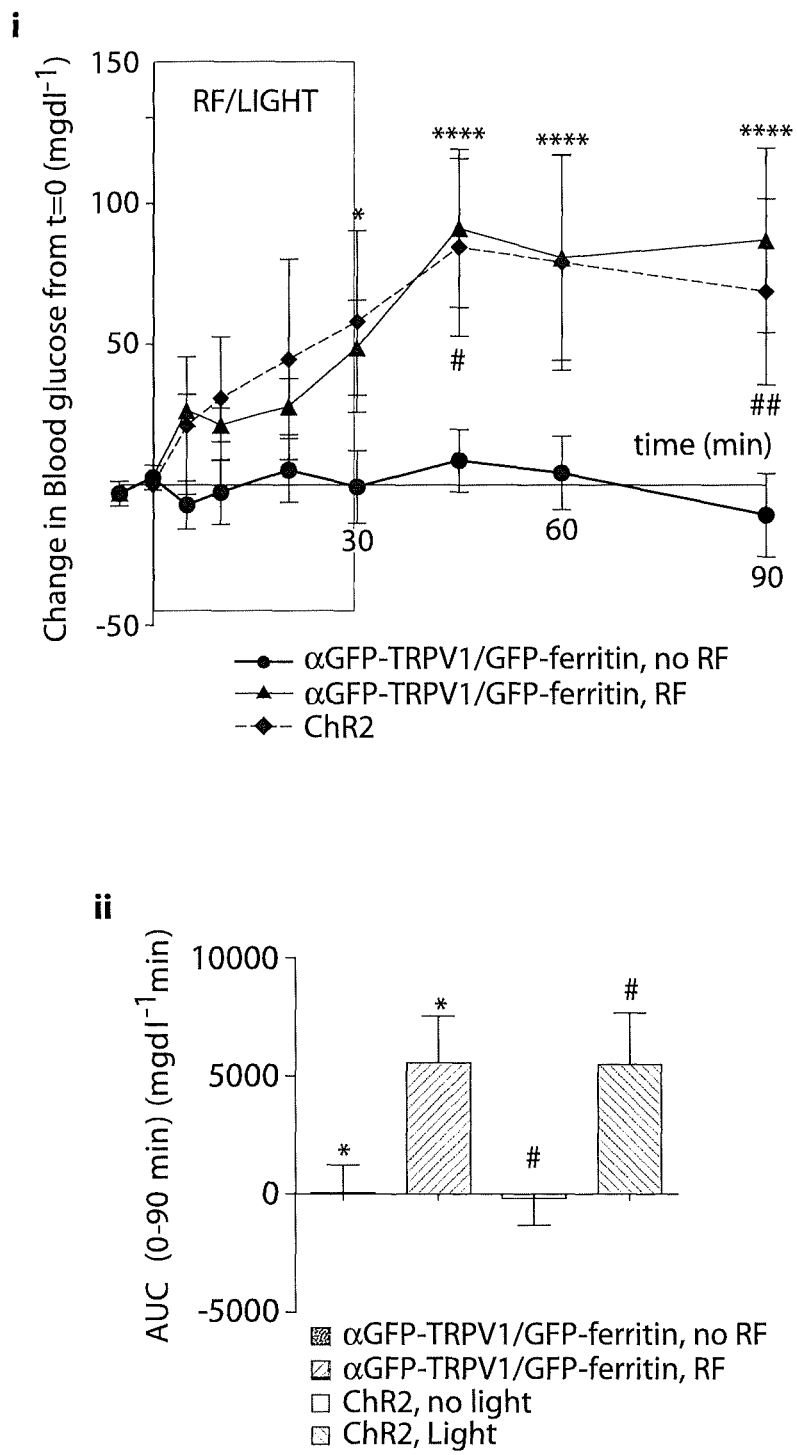
FIG. 6B presents graphs showing that RF treatment of GK-cre mice with VMH expression of αGFP-TRPV1/GFP-ferritin (n=13) i) significantly increases blood glucose and ii) cumulative change in blood glucose compared to no RF treatment and is similar to the effect of blue light stimulation in GK-cre mice with VMH expression of ChR2 (n=4). Data shown as mean and SEM. Data were analyzed by two way ANOVA with Sidak's multiple comparison test. * and # indicate P<0.05, ## indicates P<0.01 and **** indicates P<0.0001 between RF-treated and untreated groups.
Figure 6C:
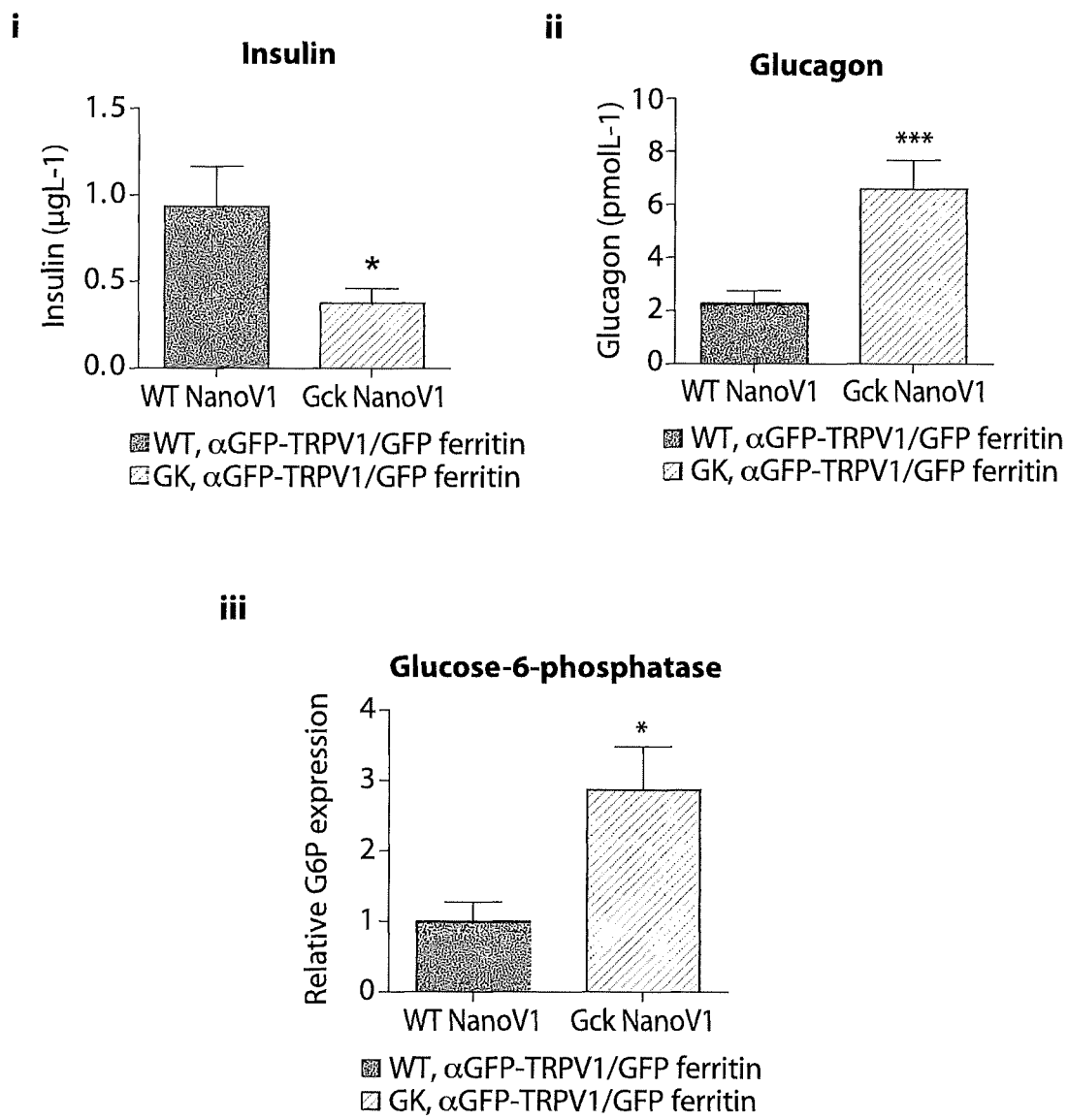
FIG. 6C presents graphs showing that RF treatment of GK-cre mice with VMH injection of Ad-FLEX-αGFP-TRPV1/GFP-ferritin (n=8-10) significantly i) decreased plasma insulin ii) increased plasma glucagon and iii) significantly increased hepatic expression of glucose-6-phosphatase compared to WT mice (n=9-12). Columns represent mean and error bars indicate SEM. Data were analyzed by two-tailed unpaired Student's t-test or Mann-Whitney test. * indicates P<0.05, *** indicates P<0.005.
Figure 9A:
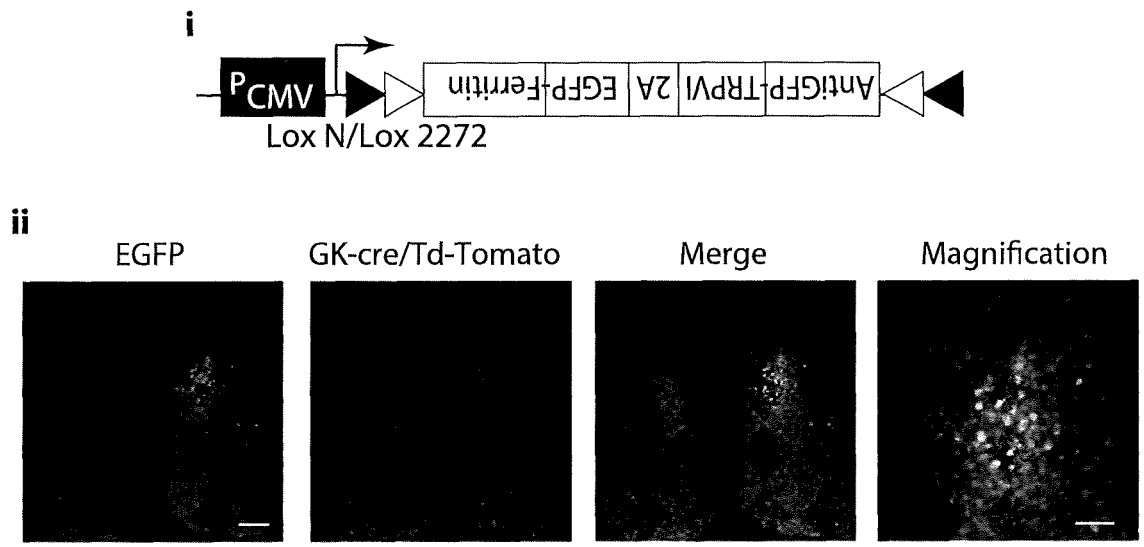
FIG. 9A illustrates i) Construct design for Ad-FLEX-αGFP-TRPV1/GFP-ferritin. CMV-cytomegalovirus promoter, loxN and lox2272 are orthogonal recombination sites; and ii) immunostaining for EGFP in GK-cre/Td-tomato mice demonstrating expression of the GFP in glucokinase neurons after VMH injection of Ad-FLEX-αGFP-TRPV1/GFP-ferritin. Scale bar 100 μm and 50 um in magnification panel.

Replication deficient adenovirus with cre-dependent expression of αGFP-TRPV1/GFP-ferritin (Ad-FLEX-αGFP-TRPV1/GFP-ferritin) was injected into the VMH of glucokinase-cre (GK-cre) mice which express cre in glucose-sensing neurons[38] (FIG. 9A). RF treatment of GK-cre mice with VMH αGFP-1 TRPV1/GFP-ferritin expression significantly increased blood glucose (Δ Blood glucose at 30 min: RF treated 48.9±16.9 mgdl$^{-1}$, vs. untreated −0.7±12.9 mgdl$^{-1}$, p<0.05. At 45 min: RF treated 91.3±28.2 mgdl$^{-1}$ vs. untreated 8.7±11.1 mgdl$^{-1}$, p<0.05) and the cumulative change in blood glucose (AUC (0-90 min): RF treated 5562±1977 mg dl$^{-1}$ min vs. untreated 62±1184 mg dl$^{-1}$ min, p<0.05) (FIG. 6B). The time-course and extent of RF activation were almost superimposable on that seen with optogenetic activation of VMH glucose sensing neurons (FIG. 6B). RF treatment of GK-cre mice with VMH expression of αGFP-TRPV1/GFP-ferritin halved plasma insulin, increased plasma glucagon 3 fold and significantly induced expression of the hepatic gluconeogenic enzyme10, glucose-6-phosphatase (G6P) (FIG. 6C). Thus, remote activation of VMH glucose-sensing neurons increases blood glucose by inducing changes in pancreatic hormones.

Figure 9B:
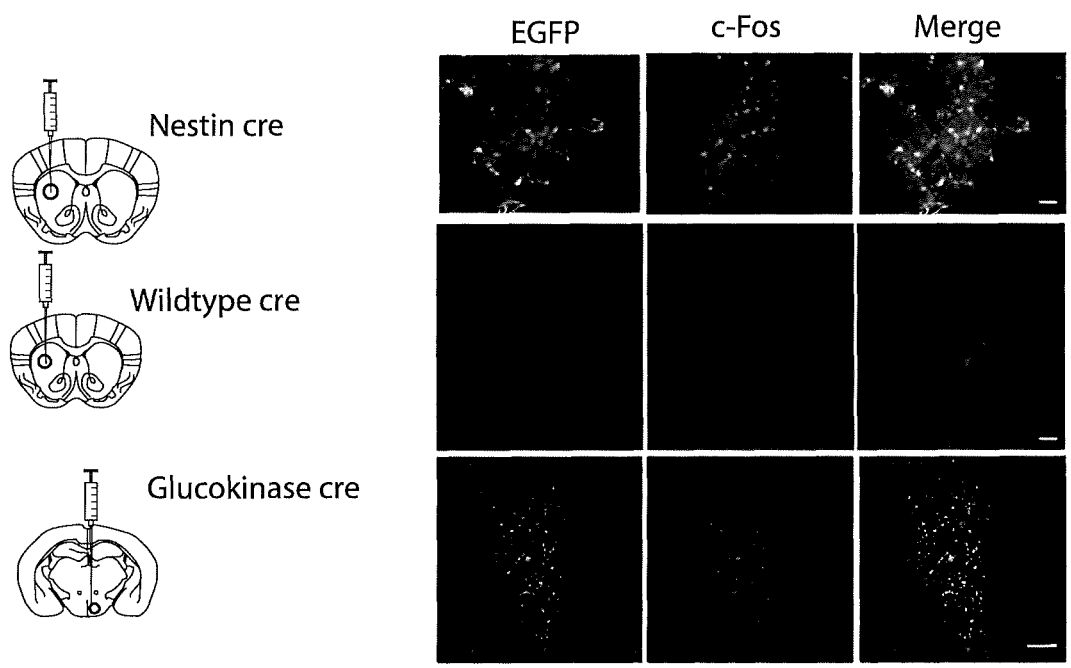
FIG. 9B illustrates colocalization between EGFP and c-Fos after RF treatment of Nestin-cre (upper panels) or wildtype (middle panels) mice injected with Ad-FLEX-αGFP-TRPV1/GFP-ferritin into the striatum (Scale bar 80 μm) and of GK-cre mice injected with Ad-FLEX-αGFP-TRPV1/GFP-ferritin into the VMH (lower panels). Scale bar 100 μm.
Figure 9C:
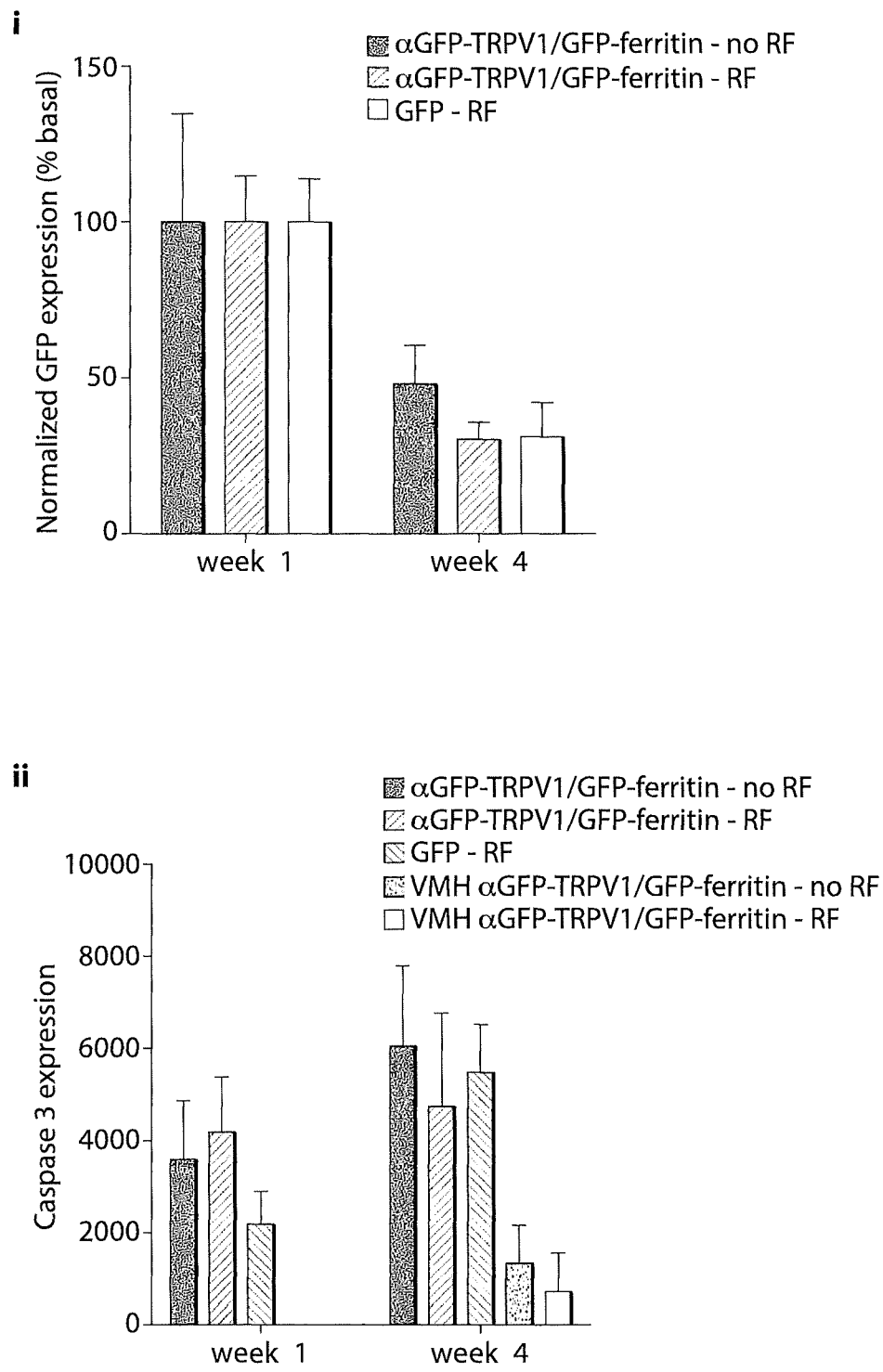
FIG. 9C presents graphs showing quantification of i) GFP and ii) activated caspase 3 immunostaining in mice following injection of Ad-αGFP-TRPV1/GFP-ferritin or Ad-GFP (1 μl) into the striatum of wildtype mice (WT) or injection of Ad-FLEX-αGFP-TRPV1/GFP-ferritin into the VMH of GK-cre mice. In all cases, columns represent mean and error bars indicate SEM. Data were analyzed by Kruskal-Wallis test with post-hoc Dunn's correction. n=4 mice per group.
Figure 10A:
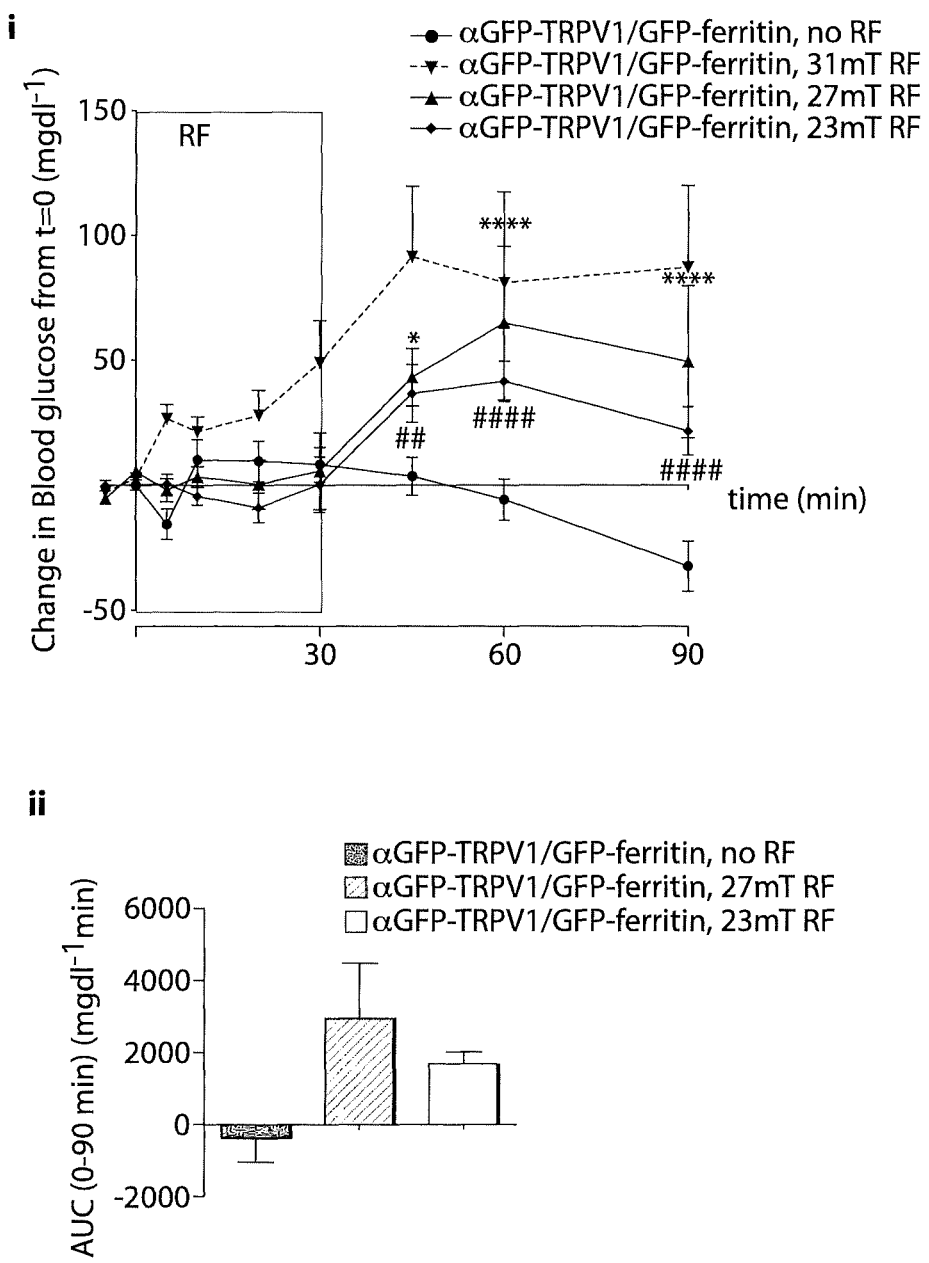
FIG. 10A presents graphs showing the effect of increasing RF field strength on (i) the change in blood glucose and (ii) the cumulative change in blood glucose in GK-cre mice with VMH injection of Ad-FLEX-αGFP-TRPV1/GFP-ferritin. Data is shown as mean and error bars indicate SEM. Data were analyzed by 2 way Anova with Sidak's multiple comparisons. * or # indicates P<0.05,  or ## indicates P<0.01, * or ### indicates P<0.001, **** or #### indicates P<0.0001 between treated and untreated groups.
Figure 10B:
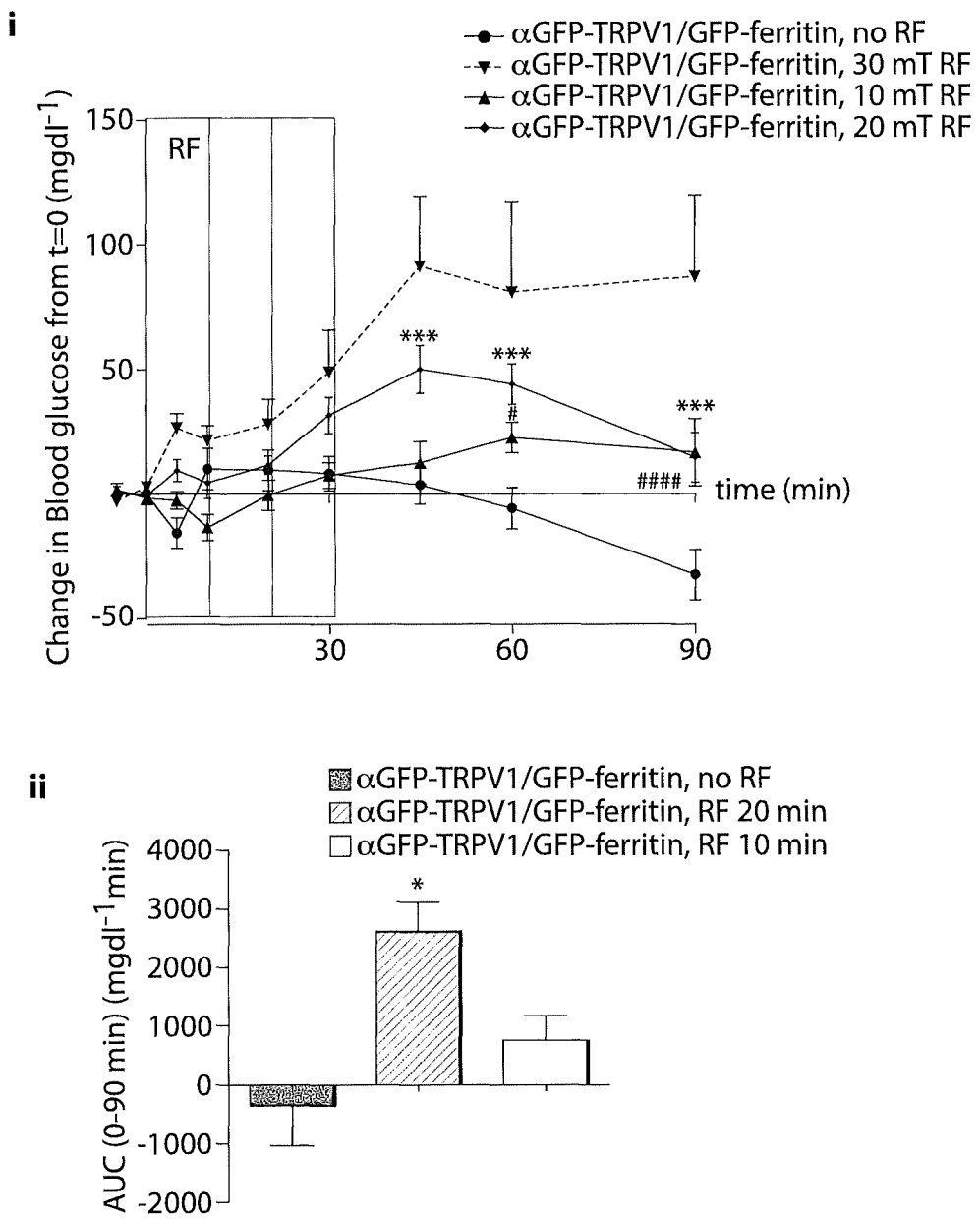
FIG. 10B presents graphs showing the effect of increasing RF treatment duration on (i) the change in blood glucose and (ii) the cumulative change in blood glucose in GK-cre mice with VMH injection of Ad-FLEX-αGFP-TRPV1/GFP-ferritin. Data is shown as mean and error bars indicate SEM.

Rise in blood glucose was dependent on RF field strength and length of treatment (FIGS. 10A and 10B). RF treatment of WT mice with VMH injection of Ad-FLEX-αGFP-TRPV1/GFP-ferritin did not alter blood glucose (FIGS. 11B to 11D). RF treatment induced c-fos expression only in GFP expressing neurons and not in RF-treated wildtype (WT) mice and expression of αGFP-TRPV1/GFP ferritin, with or without RF, does not alter apoptotic cell count compared to control virus expressing GFP (FIGS. 9B and 9C).

Consistent with these in vivo data, radio waves also remotely stimulated $Ca^{2+}$ entry in N38 cells in vitro (FIG. 12A). This enabled us to test the kinetics of activation. In clonal hypothalamic cells (N38) stably expressing these constructs, RF treatment (465 KHz) significantly increased the number of cells with raised intracellular calcium, presumably through TRPV1 channel mediated depolarization leading to opening of voltage-gated calcium channels. These effects were blocked by the TRP channel inhibitor, ruthenium red. The mode response time was 11-15 sec after RF onset (FIG. 12A(iii)). Calcium responses were proportional to RF field strength and a 10 sec RF pulse was sufficient to significantly increase intracellular calcium (FIG. 12B). RF treatment of N38 cells expressing αGFP-TRPV1/GFP-ferritin also significantly increased phospho cAMP-responsive element binding protein (pCREB) levels, a canonical target of calcium signaling[40] and expression of the calcium and activity responsive proto-oncogene, c-fos and these effects were blocked by ruthenium red (FIG. 12C). A small increase in c-fos and no increase in pCREB were seen with RF treatment of N38 cells without αGFP-TRPV1/GFP-ferritin (FIGS. 13A and 13B). Immunohistochemistry and immuno-EM of brain sections further confirmed their co-expression in neurons in vivo (FIGS. 12D and 12E).

A method for non-invasive neural inhibition would allow a further analysis of the physiological role of specific neural populations and potentially provide an alternative to deep brain stimulation which is thought to act by local neural inhibition. We thus modified our technology to enable remote neural silencing. An amino acid substitution, from isoleucine to lysine in the S6 pore region of the TRP family channels, M2 and M8 has been shown to change ionic selectivity from cations to chloride ions[42]. We introduced and tested the effect of an analogous mutation in the S6 region of TRPV1 (I679K) (FIG. 18) to create a TRPV1$^{Mutant}$ channel by imaging for chloride entry using MQAE. In N38 cells stably transfected with αGFP-TRPV1$^{Mutant}$/GFP-ferritin, the TRP agonist 2APB significantly increased level of intracellular chloride measured by MQAE quenching. This effect was blocked by ruthenium red (FIG. 7B and FIG. 15E(ii)). In contrast to the wild type TRPV1, RF treatment of N38 cells expressing αGFP-TRPV1$^{Mutant}$/GFP-ferritin significantly reduced pCREB levels and failed to increase c-fos expression (FIG. 14A).

Figure 7A:
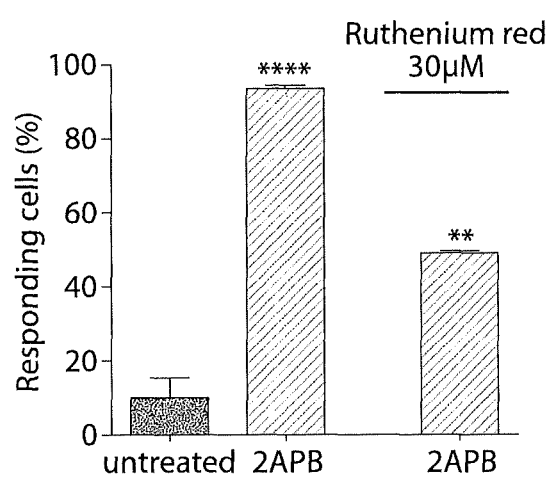
FIG. 7A is a graph showing that treatment of N38 cells expressing αGFP-TRPV1$^{Mutant}$/GFP-ferritin with 2APB (n=4 occasions) significantly increased the percentage of responding cells (>10% decrease in chloride indicator, MQAE, fluorescence) compared to untreated cells (n=4 occasions) and was reduced by Ruthenium red (n=2 occasions for each treatment condition). Columns represent mean and error bars indicate SEM. Data were analyzed by Kruskal Wallis test with Dunn's multiple comparison test.  indicates P<0.01 and ** indicates P<0.001 vs. untreated.
Figure 7B:
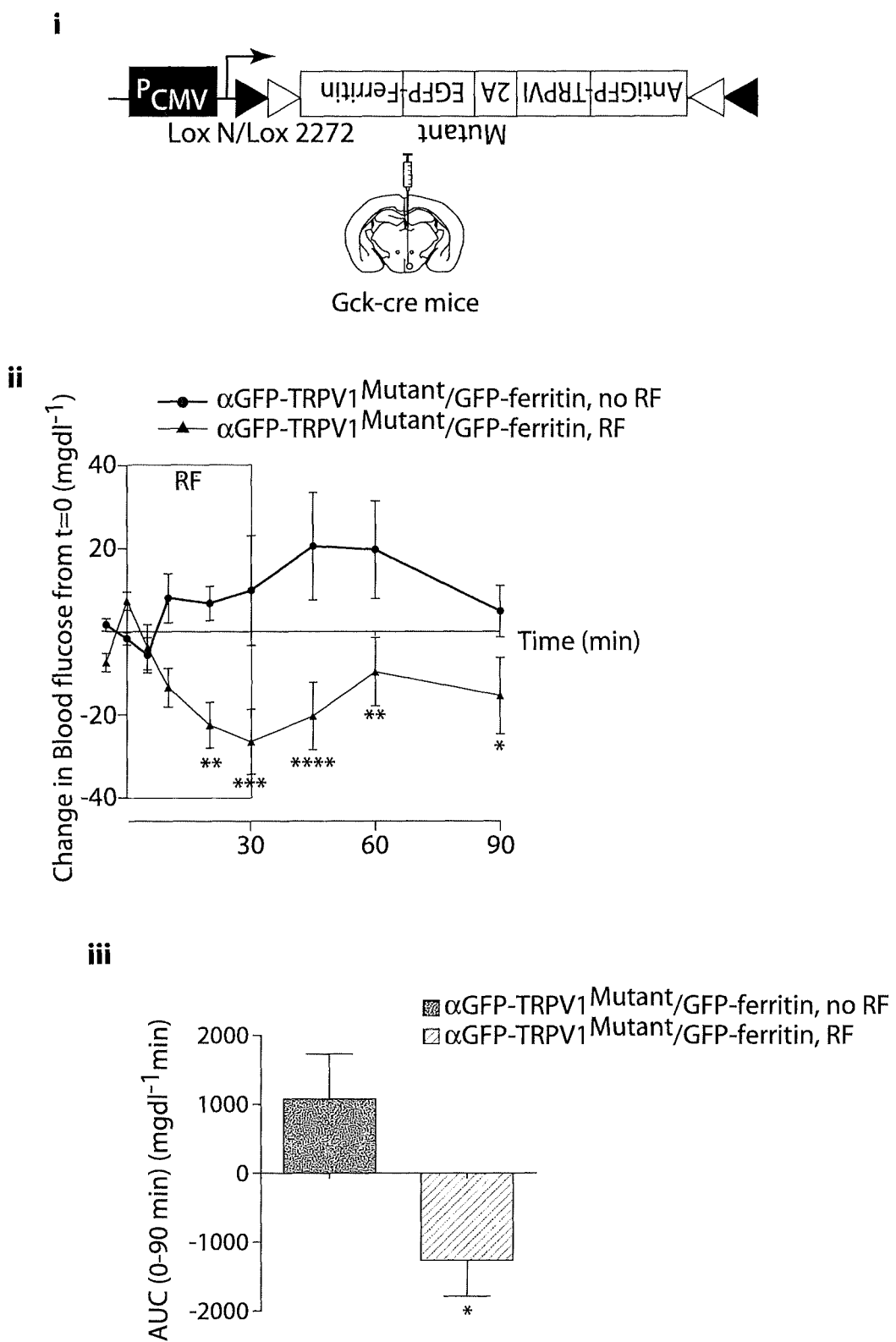
FIG. 7B illustrates (i) Construct design and injection site for FLEX-αGFP-TRPV1$^{Mutant}$/GFP-ferritin. CMV—cytomegalovirus promoter, loxN and lox2272 are orthogonal recombination sites; and presents graphs showing that RF treatment of GK31 cre mice with VMH expression of αGFP-TRPV1$^{Mutant}$/GFP-ferritin ii) significantly decreases blood glucose and iii) significantly decreases cumulative change in blood glucose over the course of the study compared to no RF treatment (n=13). Data indicate mean and error bars indicate SEM. Data were analyzed by two way ANOVA with Sidak's multiple comparison test and two-tailed, Student's t-test. * indicates P<0.05,  indicates P<0.01, * indicates P<0.001 and**** indicates P<0.0001 between RF-treated and untreated groups.
Figure 7C:
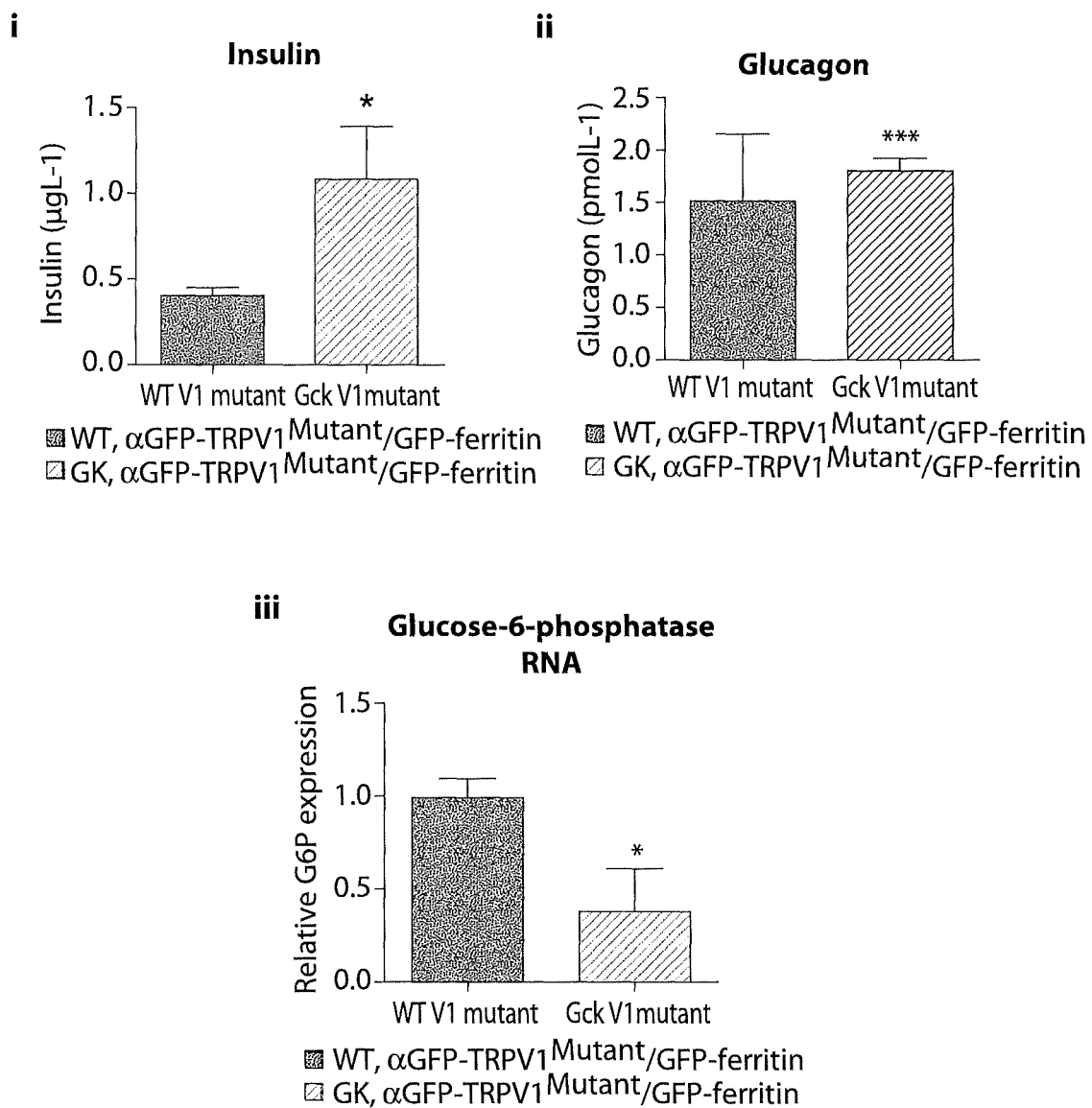
FIG. 7C presents graphs showing that RF treatment i) significantly increased plasma insulin (GK-cre=9, WT=9), ii) did not significantly alter plasma glucagon (GK-cre=5, WT=9) and iii) significantly decreased hepatic expression of glucose-6-phosphatase in GK-cre mice (n=4) compared to WT mice with VMH injection of Ad-FLEX-αGFP-TRPV1$^{Mutant}$/GFP-ferritin (n=8). Columns represent mean and error bars indicate SEM. Data were analyzed by two-tailed, unpaired Student's t-test. * indicates P<0.05.
Figure 7D:
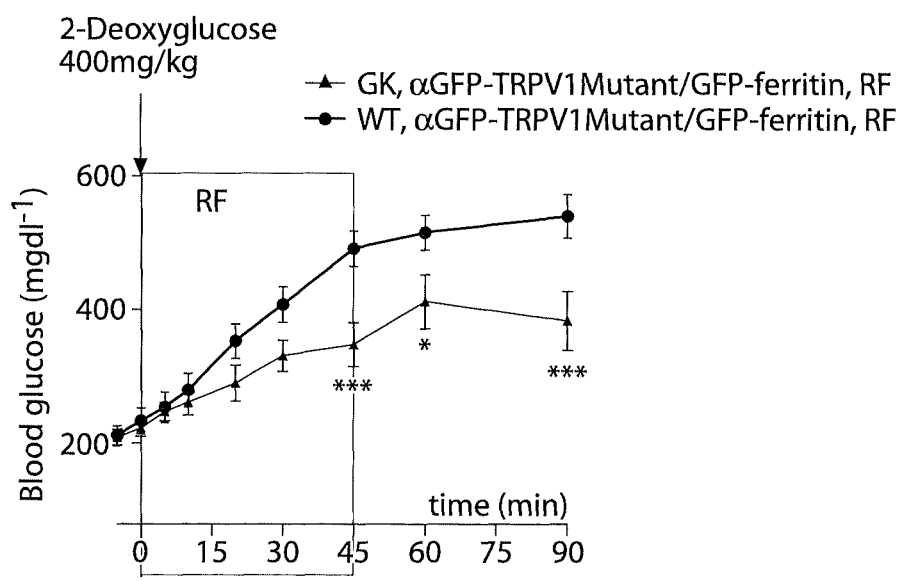
FIG. 7D is a graph showing that RF treatment significantly decreases blood glucose over the course of the study in GK-cre mice with VMH expression of αGFP-TRPV1$^{Mutant}$/GFP-ferritin (n=6) compared to WT mice with VMH injection of Ad-FLEX-αGFP-TRPV1$^{Mutant}$/GFP-ferritin (n=9) after administration of 2-Deoxyglucose to mimic hypoglycemia. Data is shown as mean and error bars indicate SEM. Data were analyzed by two way ANOVA with Sidak's multiple comparison test. * indicates P<0.05 and *** indicates P<0.001.

We next tested whether remote inhibition of VMH glucose-sensing neurons could alter glucose metabolism in vivo. RF treatment of fasted GK-cre mice following VMH injection of adenovirus with cre-dependent expression of αGFP-TRPV1$^{Mutant}$/GFP-ferritin (Ad-FLEX-αGFP-TRPV1$^{Mutant}$/GFP ferritin) significantly reduced blood glucose (Δ Blood glucose at 20 min: RF treated −22.5±5.5 mgdl$^{-1}$ vs. untreated 6.8±4.1 mgdl$^{-1}$, p<0.01. At 30 min: RF treated −26.5±7.8 mgdl$^{-1}$ vs. untreated 9.9±13.1 mgdl$^{-1}$, p<0.001. At 45 min: RF treated −20.3±8.2 mgdl$^{-1}$ vs. untreated 20.6±12.9 mgdl$^{-1}$, p<0.0001) as well as the cumulative change in blood glucose (FIG. 7C). RF treatment of GK-cre mice with VMH expression of αGFP-TRPV1$^{Muatmt}$/GFP-ferritin significantly increased insulin without a compensatory rise in glucagon and significantly reduced expression of hepatic G6P (FIG. 7D). There was no effect of RF treatment on WT mice following VMH injection of Ad-FLEX-αGFP-TRPV1$^{Mutant}$/GFP-ferritin (FIG. 14D). In addition, remote RF inhibition of VMH glucose-sensing neurons blunted the response to hypoglycemia elicited by 2-deoxyglucose, a non-metabolizable form of glucose that inhibits intracellular glycolysis (FIG. 7E and FIG. 14C). Taken together, these results suggest that VMH glucose-sensing neurons are necessary for the complete counter-regulatory responses to hypoglycemia and also to maintain normal levels of blood glucose after an overnight fast.

We previously showed that, owing to the fact that ferritin is superparamagnetic, ferritin-tethered TRPV1 could activate gene expression in a magnetic field[22,30]. We thus tested whether application of a permanent magnet could also modulate neural activity by making whole-cell voltage and current clamp recordings. Note, we were unable to make electrophysiological recordings using radiowaves because they heated the electrode and caused other recording artifacts not seen when using a magnet. Exposure of HEK or N38 cells expressing αGFP-TRPV1/GFP-ferritin to a magnetic field using a static magnet (5s) induced a significant inward current. In contrast, magnet treatment (5s) induced an outward current in HEK or N38 cells expressing TRPV1$^{Mutant}$/GFP-ferritin (FIGS. 15A and 15B). Peak magnet-induced current displayed a rise time of $0.62\pm0.4$s and a 37% decay time of $1.1\pm0.74$ for the activating channel and $2.29\pm1.8$s and $11.7\pm4.9$s respectively for the mutant channel. The I-V relationship of the mutant channel with different intracellular anions (FIG. 15C) was consistent with the analogous pore loop mutation in TRPM2 and TRPM813. Magnet treatment of N38 cells expressing αGFP2 TRPV1/GFP-ferritin increased intracellular calcium in a field-dependent fashion while magnet treatment of N38 cells expressing αGFP-TRPV1$^{Mutant}$/GFP-ferritin increased intracellular chloride and these effects were blocked by ruthenium red (FIGS. 15D and 15E).

Figure 8A:
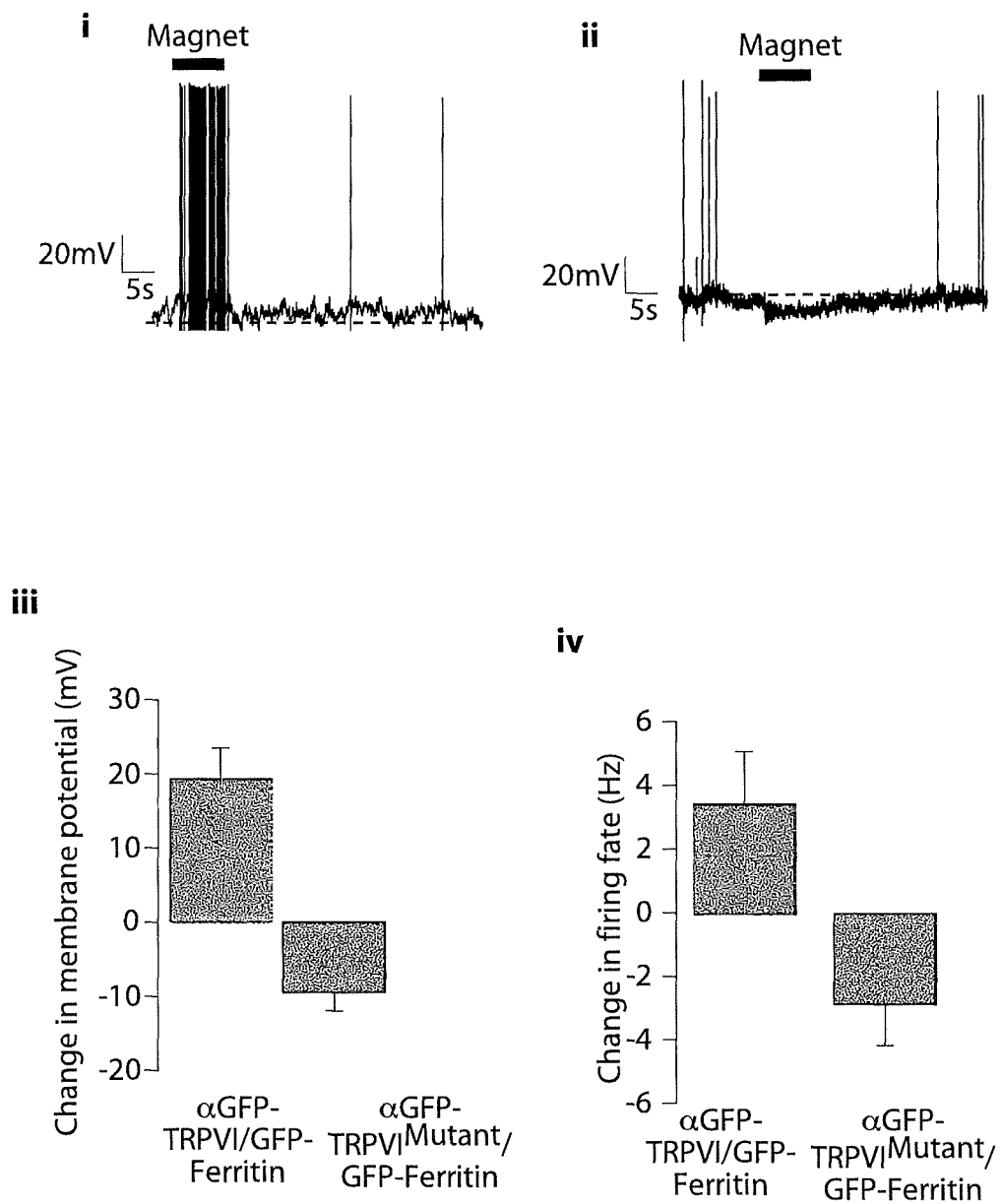
FIG. 8A presents (i) Whole-cell current-clamp trace from GK VMH neurons expressing αGFP-TRPV/GFP-ferritin showing depolarization and increased firing rate with magnet (5s) in a hyperpolarized neuron; (ii) Whole-cell current-clamp trace from GK VMH neurons expressing αGFP-TRPV1$^{Mutant}$/GFP-ferritin showing hyperpolarization with magnet (5s) in a neuron; (iii) Bar chart summary of change in membrane potential with magnet activation in VMH neurons expressing αGFP-TRPV1/GFP-ferritin and αGFP-TRPV1$^{Mutant}$/GFP-ferritin and (iv) Bar chart summary of change in firing rate with magnet activation in VMH neurons expressing αGFP TRPV1/GFP-ferritin and αGFP-TRPV1$^{Mutant}$/GFP-ferritin and αGFP-TRPV1$^{Mutant}$/GFP-ferritin. For VMH neurons expressing αGFP-TRPV1/GFP-ferritin mean membrane potential significantly increased from −70.20±7.246 mV to −53.81±5.349 mV (n=14, p<0.0001 paired t-test). Mean firing rate significantly increased from 0.7084±0.2311 to 3.063±0.5632 (n=16 p<0.002 paired t-test. Includes data from 2 cell-attached recordings). For VMH neurons expressing αGFP-TRPV1$^{Mutant}$/GFP-ferritin mean membrane potential significantly decreased from −51.2±5.519 mV to −55.93±5.636 mV (n=6, p=0.03 Wilcoxon matched pairs). Mean firing rate significantly decreased from 2.868±1.177 to 0.3167±0.2685 (n=6 p=0.03 Wilcoxon matched pairs).

We next tested the effects of magnet treatment on neural activity in hypothalamic slices. Glucokinase-cre (GK-cre) mice were crossed to the reporter strain Rosa-TdTomato to label GK neurons and then received injections of the Ad-αGFP-TRPV1/GFP-ferritin or Ad-αGFP-TRPV1$^{Mutant}$/GFP-ferritin into the VMH. In mice injected with Ad-αGFP-TRPV1/GFP-ferritin, magnet treatment (5 sec) of slices depolarized neurons expressing td-tomato and GFP leading to a significant increase in membrane potential $15.7\pm2.8$ mV ($P<0.001$, $n=16$) and firing rate of $2.60\pm0.8$ Hz ($P<0.001$, $n=12$) in 76% of neurons (FIG. 8A(i, iii and iv)). In mice injected with Ad-αGFP-TRPV1$^{Mutant}$/GFP-ferritin, magnet treatment (5s) of slices led to a significant hyperpolarization in membrane potential of $-9.5\pm2.6$ mV ($P<0.05$, $n=6$ Wilcoxon matched pairs) and decrease in firing rate $-2.90\pm1.70$ ($p<0.05$, $n=6$ Wilcoxon matched pairs) in 71% of neurons (FIG. 8A(ii, iii and iv)). Peak magnet-induced current displayed a rise time of $0.62\pm0.4$s and a 37% decay time of $1.1\pm0.74$ for the activating channel and $2.29\pm1.8$s and $11.7\pm4.9$s respectively for the mutant channel. Baseline characteristics in hypothalamic cells expressing the constructs were unaffected (see methods).

Figure 8B:
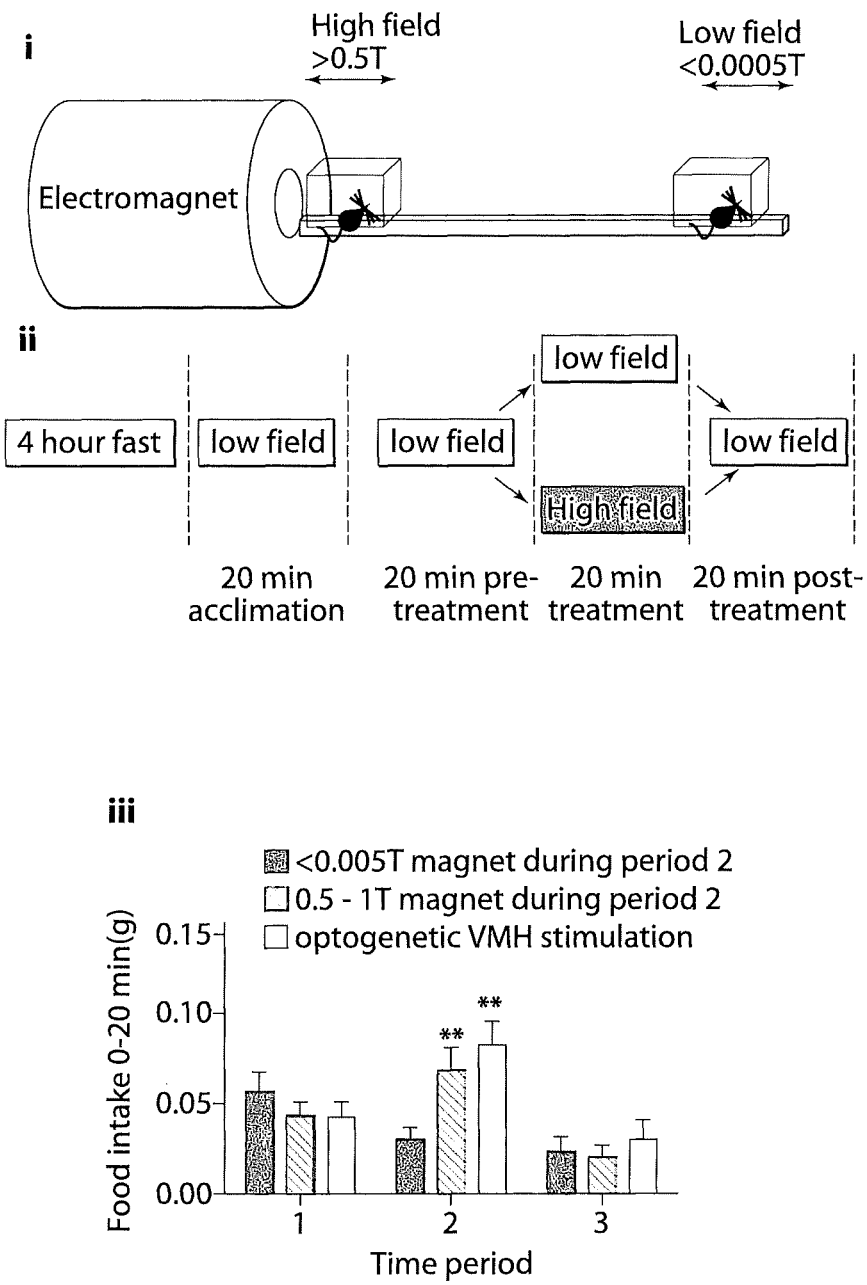
FIG. 8B presents (i) a schema of delivery system for low and high strength magnetic field in vivo using a 3T electromagnet; (ii) a schema of the protocol used to examine the effect of neural activation with a static magnetic field on food intake; (iii) a graph showing the effect of increasing magnetic field strength on food intake in GK-cre mice expressing αGFP-TRPV1/GFP-ferritin in the VMH. Magnetic field treatment of GK-cre mice with VMH expression of αGFP-TRPV1/GFP-ferritin significantly increases food intake in period 2 compared to low field strength magnet treatment (n=6). The increase in food intake is similar to that seen with blue light stimulation of GK-cre mice with VMH expression of ChR2 (n=4). Data points indicate mean and error bars indicate SEM. Data were analyzed by 2 way Anova with Sidak's multiple comparisons. ** indicates P<0.01 between treated and untreated groups.
Figure 8C:
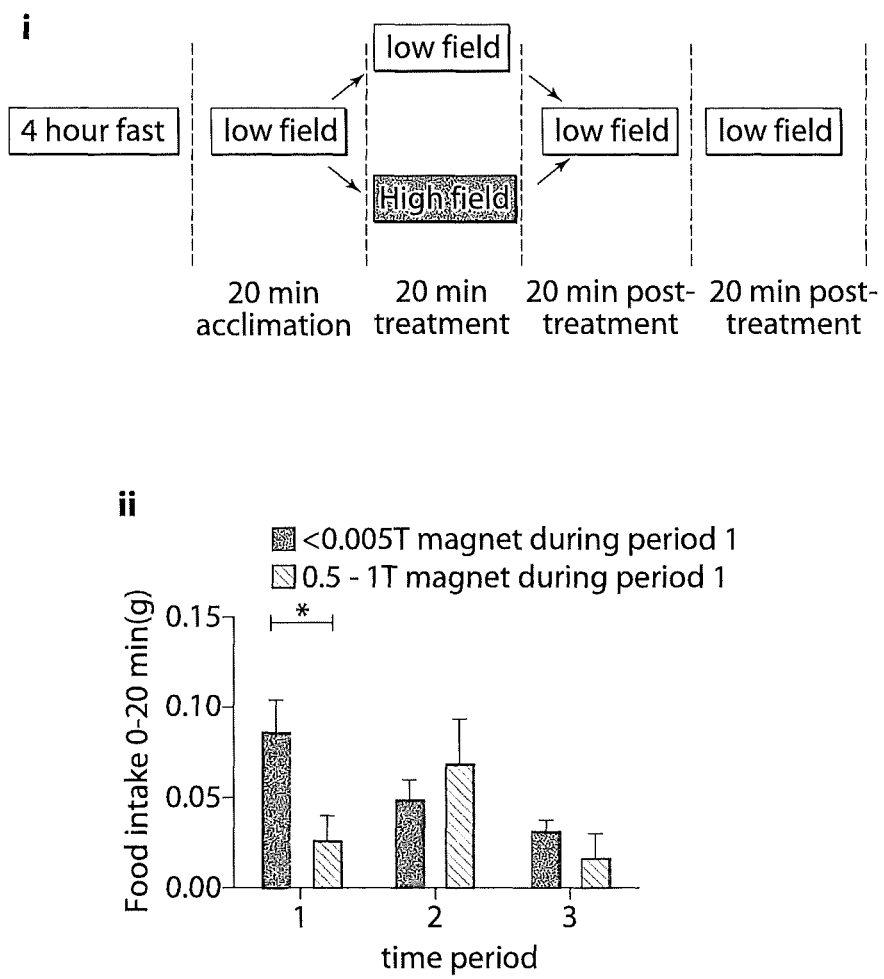
FIG. 8C presents (i) a schema of the protocol used to examine the effect of neural inhibition with a static magnetic field on food intake; and (ii) a graph showing that magnetic field treatment of GK-cre mice with VMH expression of αGFP23 TRPV1$^{Mutant}$/GFP-ferritin significantly reduces food intake in period 1 compared to low field strength magnet treatment. Data points indicate mean and error bars indicate SEM. Data were analyzed by 2 way Anova with Sidak's multiple comparisons. * indicates P<0.05 between treated and untreated groups.

We next tested whether an external magnetic field generated by the electromagnetic coil of a standard MRI machine could remotely modulate neurons in vivo to control behavior (FIG. 8B(i)). Since hypoglycemia triggers potent behavioral responses, we reasoned that activation of glucokinase neurons in the VIH, which evokes the same endocrine response as does hypoglycemia, might increase food intake. To evaluate whether VMH glucose-sensing neurons contribute to the glucoprivic feeding response, we treated animals with a magnetic field (adjacent to an MRI machine) during three 20 minute intervals after a fast[44]. Magnet activation of VMH GK neurons expressing αGFP-TRPV1/GFP-ferritin not only increased blood glucose (FIG. 16B) but also significantly increased food intake (FIG. 8B(iii)). The feeding response was similar to that seen with optogenetic activation of VMH GK-cre neurons. We next tested whether inhibition of these neurons could decrease food intake by injecting Ad-αGFP-TRPV1$^{Mutant}$/GFP-ferritin into the VMH of Gk-cre mice. In contrast to neural excitation, inhibition of these neurons in a magnetic field caused a highly significant decrease of feeding immediately after a fast (FIG. 8C). These data show that inhibition of VMH neurons both lowers blood glucose and decreases feeding, effects that would be beneficial for the treatment of metabolic disease. For both the activating and inhibitory constructs, there was no effect of construct expression on baseline blood glucose or food intake without treatment (FIG. 17) and no effect of the magnetic field on either blood glucose or feeding was seen in WT mice after VMH injection of either Ad-αGFP-TRPV1/GFP-ferritin (FIG. 16C).

In this report, we show that remote modulation of VMH glucose-sensing neurons can change blood glucose in either direction likely by regulating the levels of the pancreatic hormones, glucagon and insulin, and that neural activation increases feeding while inhibition decreases it. The finding that VMH activation can increase food intake was surprising since this nucleus has traditionally been thought of as a satiety center[45,46]. The finding that inhibition of these neurons lowers glucose and decreases feeding after a four hour fast further suggests that these cells also play a role to maintain food intake during the course of a day and that inhibition of these neurons could have beneficial effects in a setting of metabolic disease. Because activation of VMH GK neurons mimics the responses to low glucose, and inhibiting them blunts this response we hypothesize that we targeted glucose-inhibited neurons. The mechanism by which glucose inhibits neurons is unclear and several mechanisms have been suggested[47,48]. While it is possible that local heating of the particles could have had independent effects via mitochondrial UCP2 or other mechanisms, we consider this unlikely because of the dissipation of heat with distance and the finding that wild type and mutant TRPV1 had opposite effects[49].

Employing radiowaves or magnetic fields to control neural activity provides a new means for neural modulation with useful features relative to optogenetics or DREADDs. Unlike optogenetics, the approach does not require a permanent implant and could prove suitable in sites where an implant may interfere with function or cannot be secured. Further, both optogenetics and other methods using exogenous nanoparticles[9,50] target local populations whereas our genetically encoded system could potentially modulate dispersed populations and/or multiple different sites in a circuit simultaneously without the need for multiple implants or injections. Indeed, incorporation of the TRPV1 and ferritin constructs into transgenic mice could obviate the need for injections altogether (other than at most a single injection of iron). The system described here also enables more rapid responses than DREADDs[51] which can be slow[52,53] potentially limiting their utility for acutely controlling behavior. Since calcium and/or chloride currents regulate the activity of many cell types, our method can also be applied to regulate the activity of many other, even dispersed, populations such as immune, epithelial and endocrine cells (and others).

While this invention has been particularly shown and described with references to preferred embodiments thereof, it will be understood by those skilled in the art that various changes in form and details may be made therein without departing from the scope of the invention encompassed by the appended claims.

REFERENCE LIST

1. Davidson, B. L. & Breakefield, X. O. Viral vectors for gene delivery to the nervous system. *Nat. Rev Neurosci.* 4, 353-364 (2003).

2. Ando, H., Furuta, T., Tsien, R. Y., & Okamoto, H. Photo-mediated gene activation using caged RNA/DNA in zebrafish embryos. *Nat. Genet.* 28, 317-325 (2001).
3. Cambridge, S. B., Davis, R. L., & Minden, J. S. *Drosophila* mitotic domain boundaries as cell fate boundaries. *Science* 277, 825-828 (1997).
4. Wang, X., Chen, X., & Yang, Y. Spatiotemporal control of gene expression by a lightswitchable transgene system. *Nat. Methods* 9, 266-269 (2012).
5. Gossen, M. et al. Transcriptional activation by tetracyclines in mammalian cells. *Science* 268, 1766-1769 (1995).
6. Danielian, P. S., Muccino, D., Rowitch, D. H., Michael, S. K., & McMahon, A. P. Modification of gene activity in mouse embryos in utero by a tamoxifen-inducible form of Cre recombinase. *Curr. Biol* 8, 1323-1326 (1998).
7. Bocker, R., Estler, C. J., Maywald, M., & Weber, D. Comparison of distribution of doxycycline in mice after oral and intravenous application measured by a high-performance liquid chromatographic method. *Arzneimittelforschung.* 31, 2116-2117 (1981).
8. Peters, R. W., Shafton, E., Frank, S., Thomas, A. N., & Scheinman, M. M. Radiofrequency triggered pacemakers: uses and limitations. A long-term study. *Ann. Intern. Med* 88, 17-22 (1978).
9. Stanley, S. A. et al. Radiowave heating of iron oxide nanoparticles can regulate plasma glucose in mice. *Science* 336, 604-607 (2012).
10. Huang, H., Delikanli, S., Zeng, H., Ferkey, D. M., & Pralle, A. Remote control of ion channels and neurons through magnetic-field heating of nanoparticles. *Nat. Nanotechnol.* 5, 602-606(2010).
11. Knight, L. C. et al. Binding and Internalization of Iron Oxide Nanoparticles Targeted to Nuclear Oncoprotein. *J Mol. Biomark. Diagn.* 1, (2010).
12. Iordanova, B., Robison, C. S., & Ahrens, E. T. Design and characterization of a chimeric ferritin with enhanced iron loading and transverse NMR relaxation rate. *J Biol. Inorg. Chem.* 15, (2010).
13. Kirchhofer, A. et al. Modulation of protein properties in living cells using nanobodies. *Nat. Struct. Mol. Biol* 17, 133-138 (2010).
14. Hong, L., Peptan, I. A., Colpan, A., & Daw, J. L. Adipose tissue engineering by human adipose-derived stromal cells. *Cells Tissues. Organs* 183, 133-140 (2006).
15. Durand, J. L., Hosinking, W., & Jelicks, L. A. Time course of effects of inhalation anesthesia on blood glucose level in male and female C57BL/6 mice. *Horm. Metab Res* 41, 339-341 (2009).
16. Fortin, J. P. et al. Size-sorted anionic iron oxide nanomagnets as colloidal mediators for magnetic hyperthermia. *J Am. Chem. Soc.* 129, 2628-2635 (2007).
17. Liedtke, W. et al. Vanilloid receptor-related osmotically activated channel (VR-OAC), a candidate vertebrate osmoreceptor. *Cell* 103, 525-535 (2000).
18. Gilles, C. et al. Magnetic hysteresis and superantiferromagnetism in ferritin nanoparticles. *Journal of Magnetism and Magnetic Materials* 241, 430-440 (2002).
19. Johnsen, S. & Lohmann, K. J. The physics and neurobiology of magnetoreception. *Nat. Rev Neurosci.* 6, 703-712 (2005).
20. Arosio, P., Ingrassia, R., & Cavadini, P. Ferritins: A family of molecules for iron storage, antioxidation and more. *Biochim. Biophys. Acta* 1790, 589-599 (2008).
21. Fortin, J. P., Gazeau, F., & Wilhelm, C. Intracellular heating of living cells through Neel relaxation of magnetic nanoparticles. *Biophysics Letter* 37, 223-228 (2008).
22. Kim, T., Moore, D., & Fussenegger, M. Genetically programmed superparamagnetic behavior of mammalian cells. *J Biotechnol.* 162, 237-245 (2012).
23. Beyer, B. K., Stark, K. L., Fantel, A. G., & Juchau, M. R. Biotransformation, estrogenicity, and steroid structure as determinants of dysmorphogenic and generalized embryotoxic effects of steroidal and nonsteroidal estrogens. *Toxicol. Appl. Pharmacol.* 98, 113-127(1989).
24. Saxen, L. Drug-induced teratogenesis in vitro: inhibition of calcification by different tetracyclines. *Science* 153, 1384-1387 (1966).
25. Fussenegger, M., Schlatter, S., Datwyler, D., Mazur, X., & Bailey, J. E. Controlled proliferation by multigene metabolic engineering enhances the productivity of Chinese hamster ovary cells. *Nat. Biotechnol.* 16, 468-472 (1998).
26. Gadalla, K. K., Bailey, M. E., & Cobb, S. R. MeCP2 and Rett syndrome: reversibility and potential avenues for therapy. *Biochem. J* 439, 1-14 (2011).
27. Samaranayake, H., Wirth, T., Schenkwein, D., Raty, J. K., & Yla-Herttuala, S. Challenges in monoclonal antibody-based therapies. *Ann. Med* 41, 322-331 (2009).
28. Aleman, A. Use of Repetitive Transcranial Magnetic Stimulation for Treatment in Psychiatry. *Clin. Psychopharmacol. Neurosci.* 11, 53-59 (2013).
29. Arenkiel, B. R., Klein, M. E., Davison, I. G., Katz, L. C., & Ehlers, M. D. Genetic control of neuronal activity in mice conditionally expressing TRPV1. *Nat. Methods* 5, 299-302 (2008).
30. Stanley, S. A., Sauer, J., Kane, R. S., Dordick, J. S. & Friedman, J. M. Remote regulation of glucose homeostasis in mice using genetically encoded nanoparticles. *Nature medicine* 21, 92-98, doi:10.1038/nm.3730 (2015).
31. Goto, Y., Carpenter, R. G., Berelowitz, M. & Frohman, L. A. Effect of ventromedial hypothalamic lesions on the secretion of somatostatin, insulin, and glucagon by the perfused rat pancreas. *Metabolism* 29, 986-990 (1980).
32. McCrimmon, R. J. et al. Key role for AMP-activated protein kinase in the ventromedial hypothalamus in regulating counterregulatory hormone responses to acute hypoglycemia. *Diabetes* 57, 444-450, doi:10.2337/db07-0837 (2008).
33. Davies, R., Nakajima, S. & White, N. Enhancement of feeding produced by stimulation of the ventromedial hypothalamus. *Journal of comparative and physiological psychology* 86, 414-419 (1974).
34. Penicaud, L., Rohner-Jeanrenaud, F. & Jeanrenaud, B. In vivo metabolic changes as studied longitudinally after ventromedial hypothalamic lesions. *Am J Physiol* 250, E662-668 (1986).
35. Shimazu, T., Fukuda, A. & Ban, T. Reciprocal influences of the ventromedial and lateral hypothalamic nuclei on blood glucose level and liver glycogen content. *Nature* 210, 1178-1179 (1966).
36. Schwartz, M. W. et al. Cooperation between brain and islet in glucose homeostasis and diabetes. *Nature* 503, 59-66, doi:10.1038/nature12709 (2013).
37. Kang, L., Routh, V. H., Kuzhikandathil, E. V., Gaspers, L. D. & Levin, B. E. Physiological and molecular characteristics of rat hypothalamic ventromedial nucleus glucosensing neurons. *Diabetes* 53, 549-559 (2004).
38. Stanley, S. et al. Profiling of Glucose-Sensing Neurons Reveals that GHRH Neurons Are Activated by Hypoglycemia. *Cell Metab* 18, 596-607, doi:10.1016/j.cmet.2013.09.002 (2013).

39. Nordlie, R. C., Foster, J. D. & Lange, A. J. Regulation of glucose production by the liver. *Annual review of nutrition* 19, 379-406, doi:10.1146/annurev.nutr.19.1.379 (1999).
40. Bito, H., Deisseroth, K. & Tsien, R. W. CREB phosphorylation and dephosphorylation: a Ca(2+)- and stimulus duration-dependent switch for hippocampal gene expression. *Cell* 87, 1203-1214 (1996).
41. Ghosh, A., Ginty, D. D., Bading, H. & Greenberg, M. E. Calcium regulation of gene expression in neuronal cells. *Journal of neurobiology* 25, 294-303, doi:10.1002/neu.480250309 (1994).
42. Kuhn, F. J., Knop, G. & Luckhoff, A. The transmembrane segment S6 determines cation versus anion selectivity of TRPM2 and TRPM8. *The Journal of biological chemistry* 282, 27598-27609, doi:10.1074/jbc.M702247200 (2007).
43. Landau, B. R. & Lubs, H. A. Animal responses to 2-deoxy-D-glucose administration. *Proceedings of the Society for Experimental Biology and Medicine. Society for Experimental Biology and Medicine* 99, 124-127 (1958).
44. Rowland, N. E., Bellush, L. L. & Carlton, J. Metabolic and neurochemical correlates of glucoprivic feeding. *Brain research bulletin* 14, 617-624 (1985).
45. Ruffin, M. & Nicolaidis, S. Electrical stimulation of the ventromedial hypothalamus enhances both fat utilization and metabolic rate that precede and parallel the inhibition of feeding behavior. *Brain Res* 846, 23-29 (1999).
46. King, B. M. The rise, fall, and resurrection of the ventromedial hypothalamus in the regulation of feeding behavior and body weight. *Physiology & behavior* 87, 221-244, doi:10.1016/j.physbeh.2005.10.007 (2006).
47. Evans, M. L. et al. Hypothalamic ATP-sensitive K+channels play a key role in sensing hypoglycemia and triggering counterregulatory epinephrine and glucagon responses. *Diabetes* 53, 2542-2551 (2004).
48. Murphy, B. A., Fakira, K. A., Song, Z., Beuve, A. & Routh, V. H. AMP-activated protein kinase and nitric oxide regulate the glucose sensitivity of ventromedial hypothalamic glucose-inhibited neurons. *American journal of physiology. Cell physiology* 297, C750-758, doi:10.1152/ajpcell.00127.2009 (2009).
49. Horvath, T. L. et al. Brain uncoupling protein 2: uncoupled neuronal mitochondria predict thermal synapses in homeostatic centers. *J Neurosci* 19, 10417-10427 (1999).
50. Chen, R., Romero, G., Christiansen, M. G., Mohr, A. & Anikeeva, P. Wireless magnetothermal deep brain stimulation. *Science* 347, 1477-1480, doi:10.1126/science.1261821 (2015).
51. Agulhon, C. et al. Modulation of the autonomic nervous system and behaviour by acute glial cell Gq protein-coupled receptor activation in vivo. *J Physiol* 591, 5599-5609, doi:10.1113/jphysiol.2013.261289 (2013).
52. Alexander, G. M. et al. Remote control of neuronal activity in transgenic mice expressing evolved G protein-coupled receptors. *Neuron* 63, 27-39, doi:10.1016/j.neuron.2009.06.014 (2009).
53. Nawaratne, V. et al. New insights into the function of M4 muscarinic acetylcholine receptors gained using a novel allosteric modulator and a DREADD (designer receptor exclusively activated by a designer drug). *Mol. Pharmacol.* 74, 1119-1131 (2008).
54. Falowski, S. M., Ooi, Y. C. & Bakay, R. A. Long-Term Evaluation of Changes in Operative Technique and Hardware-Related Complications With Deep Brain Stimulation. *Neuromodulation: journal of the International Neuromodulation Society*, doi:10.1111/ner.12335 (2015).
55. Caterina, M. J. et al. The capsaicin receptor: a heat-activated ion channel in the pain pathway. *Nature* 389, 816-824, doi:10.1038/39807 (1997).

We claim:

1. A method of modulating the activity of a population of cells, comprising the steps of:
    (a) providing a population of recombinant cells, said cells comprising a genetic construct comprising a nucleotide sequence which encodes an iron-binding protein fused to a first polypeptide and a nucleotide sequence which encodes a TRPV1$^{Mutant}$ ion channel fused to a second polypeptide, wherein the first polypeptide is a binding partner of the second polypeptide, and
    (b) exposing the cells to a static magnetic field, thereby activating the ion channel and modulating the activity of the cells.

2. The method of claim 1, wherein the method inhibits cell activity.

3. The method of claim 1, wherein the method increases cell activity.

4. The method of claim 1, wherein the metal binding protein is selected from the group consisting of ferritin, ferritin variants, and bacterioferritin.

5. The method of claim 1, wherein the modulated cell activity is cell proliferation and/or differentiation, apoptosis, one or more signal transduction pathways, neuronal activation, or development of long-term potentiation and/or regulation of gene expression.

* * * * *

SEQUENCE LISTING

```
<160> NUMBER OF SEQ ID NOS: 1

<210> SEQ ID NO 1
<211> LENGTH: 838
<212> TYPE: PRT
<213> ORGANISM: Rattus sp.

<400> SEQUENCE: 1

Met Glu Gln Arg Ala Ser Leu Asp Ser Glu Glu Ser Glu Ser Pro Pro
1               5                   10                  15

Gln Glu Asn Ser Cys Leu Asp Pro Pro Arg Asp Pro Asn Cys Lys
            20                  25                  30

Pro Pro Pro Val Lys Pro His Ile Phe Thr Thr Arg Ser Arg Thr Arg
            35                  40                  45

Leu Phe Gly Lys Gly Asp Ser Glu Glu Ala Ser Pro Leu Asp Cys Pro
    50                  55                  60

Tyr Glu Glu Gly Gly Leu Ala Ser Cys Pro Ile Ile Thr Val Ser Ser
65                  70                  75                  80

Val Leu Thr Ile Gln Arg Pro Gly Asp Gly Pro Ala Ser Val Arg Pro
                85                  90                  95

Ser Ser Gln Asp Ser Val Ser Ala Gly Glu Lys Pro Pro Arg Leu Tyr
            100                 105                 110

Asp Arg Arg Ser Ile Phe Asp Ala Val Ala Gln Ser Asn Cys Gln Glu
            115                 120                 125
```

```
Leu Glu Ser Leu Leu Pro Phe Leu Gln Arg Ser Lys Lys Arg Leu Thr
            130                 135                 140

Asp Ser Glu Phe Lys Asp Pro Glu Thr Gly Lys Thr Cys Leu Leu Lys
145                 150                 155                 160

Ala Met Leu Asn Leu His Asn Gly Gln Asn Asp Thr Ile Ala Leu Leu
                165                 170                 175

Leu Asp Val Ala Arg Lys Thr Asp Ser Leu Lys Gln Phe Val Asn Ala
            180                 185                 190

Ser Tyr Thr Asp Ser Tyr Tyr Lys Gly Gln Thr Ala Leu His Ile Ala
            195                 200                 205

Ile Glu Arg Arg Asn Met Thr Leu Val Thr Leu Leu Val Glu Asn Gly
210                 215                 220

Ala Asp Val Gln Ala Ala Asn Gly Asp Phe Phe Lys Lys Thr Lys
225                 230                 235                 240

Gly Arg Pro Gly Phe Tyr Phe Gly Glu Leu Pro Leu Ser Leu Ala Ala
                245                 250                 255

Cys Thr Asn Gln Leu Ala Ile Val Lys Phe Leu Leu Gln Asn Ser Trp
            260                 265                 270

Gln Pro Ala Asp Ile Ser Ala Arg Asp Ser Val Gly Asn Thr Val Leu
            275                 280                 285

His Ala Leu Val Glu Val Ala Asp Asn Thr Val Asp Asn Thr Lys Phe
290                 295                 300

Val Thr Ser Met Tyr Asn Glu Ile Leu Ile Leu Gly Ala Lys Leu His
305                 310                 315                 320

Pro Thr Leu Lys Leu Glu Glu Ile Thr Asn Arg Lys Gly Leu Thr Pro
                325                 330                 335

Leu Ala Leu Ala Ala Ser Ser Gly Lys Ile Gly Val Leu Ala Tyr Ile
            340                 345                 350

Leu Gln Arg Glu Ile His Glu Pro Glu Cys Arg His Leu Ser Arg Lys
            355                 360                 365

Phe Thr Glu Trp Ala Tyr Gly Pro Val His Ser Ser Leu Tyr Asp Leu
370                 375                 380

Ser Cys Ile Asp Thr Cys Glu Lys Asn Ser Val Leu Glu Val Ile Ala
385                 390                 395                 400

Tyr Ser Ser Ser Glu Thr Pro Asn Arg His Asp Met Leu Leu Val Glu
                405                 410                 415

Pro Leu Asn Arg Leu Leu Gln Asp Lys Trp Asp Arg Phe Val Lys Arg
            420                 425                 430

Ile Phe Tyr Phe Asn Phe Phe Val Tyr Cys Leu Tyr Met Ile Ile Phe
            435                 440                 445

Thr Ala Ala Ala Tyr Tyr Arg Pro Val Glu Gly Leu Pro Pro Tyr Lys
450                 455                 460

Leu Lys Asn Thr Val Gly Asp Tyr Phe Arg Val Thr Gly Glu Ile Leu
465                 470                 475                 480

Ser Val Ser Gly Gly Val Tyr Phe Phe Phe Arg Gly Ile Gln Tyr Phe
                485                 490                 495

Leu Gln Arg Arg Pro Ser Leu Lys Ser Leu Phe Val Asp Ser Tyr Ser
            500                 505                 510

Glu Ile Leu Phe Phe Val Gln Ser Leu Phe Met Leu Val Ser Val Val
            515                 520                 525

Leu Tyr Phe Ser Gln Arg Lys Glu Tyr Val Ala Ser Met Val Phe Ser
530                 535                 540
```

```
Leu Ala Met Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
                565                 570                 575

Leu Cys Arg Phe Met Phe Val Tyr Leu Val Phe Leu Phe Gly Phe Ser
                580                 585                 590

Thr Ala Val Val Thr Leu Ile Glu Asp Gly Lys Asn Asn Ser Leu Pro
            595                 600                 605

Met Glu Ser Thr Pro His Lys Cys Arg Gly Ser Ala Cys Lys Pro Gly
            610                 615                 620

Asn Ser Tyr Asn Ser Leu Tyr Ser Thr Cys Leu Glu Leu Phe Lys Phe
625                 630                 635                 640

Thr Ile Gly Met Gly Asp Leu Glu Phe Thr Glu Asn Tyr Asp Phe Lys
                645                 650                 655

Ala Val Phe Ile Ile Leu Leu Leu Ala Tyr Val Ile Leu Thr Tyr Ile
                660                 665                 670

Leu Leu Leu Asn Met Leu Lys Ala Leu Met Gly Glu Thr Val Asn Lys
            675                 680                 685

Ile Ala Gln Glu Ser Lys Asn Ile Trp Lys Leu Gln Arg Ala Ile Thr
690                 695                 700

Ile Leu Asp Thr Glu Lys Ser Phe Leu Lys Cys Met Arg Lys Ala Phe
705                 710                 715                 720

Arg Ser Gly Lys Leu Leu Gln Val Gly Phe Thr Pro Asp Gly Lys Asp
                725                 730                 735

Asp Tyr Arg Trp Cys Phe Arg Val Asp Glu Val Asn Trp Thr Thr Trp
            740                 745                 750

Asn Thr Asn Val Gly Ile Ile Asn Glu Asp Pro Gly Asn Cys Glu Gly
            755                 760                 765

Val Lys Arg Thr Leu Ser Phe Ser Leu Arg Ser Gly Arg Val Ser Gly
            770                 775                 780

Arg Asn Trp Lys Asn Phe Ala Leu Val Pro Leu Leu Arg Asp Ala Ser
785                 790                 795                 800

Thr Arg Asp Arg His Ala Thr Gln Gln Glu Glu Val Gln Leu Lys His
                805                 810                 815

Tyr Thr Gly Ser Leu Lys Pro Glu Asp Ala Glu Val Phe Lys Asp Ser
            820                 825                 830

Met Val Pro Gly Glu Lys
            835
```